US006797271B2

(12) United States Patent
Sleeman et al.

(10) Patent No.: US 6,797,271 B2
(45) Date of Patent: Sep. 28, 2004

(54) METHODS FOR ENHANCING IMMUNE RESPONSES BY FIBROBLAST GROWTH FACTOR RECEPTOR 5 POLYPEPTIDES

(75) Inventors: Matthew Sleeman, Royston (GB); Nevin Abernethy, Auckland (NZ); James Greg Murison, Auckland (NZ)

(73) Assignee: Genesis Research & Development Corporation Limited, Auckland (NZ)

( * ) Notice: Subject to any disclaimer, the term of this patent is extended or adjusted under 35 U.S.C. 154(b) by 0 days.

(21) Appl. No.: 09/823,038

(22) Filed: Mar. 28, 2001

(65) Prior Publication Data

US 2002/0058335 A1 May 16, 2002

Related U.S. Application Data

(63) Continuation-in-part of application No. 09/383,586, filed on Aug. 26, 1999, now Pat. No. 6,242,419, which is a continuation-in-part of application No. 09/276,268, filed on May 25, 1999, now abandoned.
(60) Provisional application No. 60/221,216, filed on Jul. 25, 2000.

(51) Int. Cl.[7] .................... A61K 38/00; A61K 38/16; C07K 14/00

(52) U.S. Cl. ................. 424/185.1; 424/198.1; 514/12; 530/350

(58) Field of Search ............... 424/185.1, 198.1; 514/2, 8, 12; 530/350

(56) References Cited

U.S. PATENT DOCUMENTS

| | | | |
|---|---|---|---|
| 5,942,420 A | * | 8/1999 | Holtzman ............ 435/69.1 |
| 2001/0016335 A1 | | 8/2001 | Young et al. |
| 2002/0009776 A1 | | 1/2002 | Saris et al. |
| 2002/0037557 A1 | | 3/2002 | Jing et al. |
| 2002/0103125 A1 | | 8/2002 | Ashkenazi et al. |

FOREIGN PATENT DOCUMENTS

| | | | |
|---|---|---|---|
| WO | WO9849302 A1 | * 11/1998 | |
| WO | WO9910364 A1 | * 11/1998 | |
| WO | 9963088 | 12/1999 | ............ C12N/15/12 |
| WO | 0024756 | 5/2000 | ............ C07H/21/04 |
| WO | WO-0149715 A2 | 7/2001 | |

OTHER PUBLICATIONS

Yaspo et al. Genomics 49:133–136, Apr. 1998.*
Mariage–Sampson et al. Genome Res. 6:492–503, 1996.*
Pietu et al Biochem J 335(Pt. 3): 549–556, Nov. 24, 1998.*
Maher, Pamela "p[38] Mitogen–activated Protein Kinase Activation Is Required for Fibroblast Growth Factor–2–stimulated Cell Proliferation but Not Differentiation", *The Journal of Biological Chemistry*, vol. 274, No. 25, pp. 17491–17498 (Jun. 18, 199).

Gruss, Hans–Jürgen and Dower, Stephen K., "Tumor Necrosis Factor Ligand Superfamily: Involvement in the Pathology of Malignant Lymphomas", *Blood*, vol. 85, No. 12, pp. 3378–3404 (Jun. 15, 1995).
Banner, David W., et al., "Crystal Sructure of the Soluble Human 55 kd TNF Receptor–Human TNFβ Complex: Implications for TNF Receptor Activation", *Cell*, vol. 73, pp. 431–445 (May 7, 1993).
Marra, M. et al., The WashU–HHMI Mouse EST Project, Accession No. AI119658, dated Sep. 2, 1998.
Marra, M. et al., The WashU–HHMI Mouse EST Project, Accession No. AA231415, dated Feb. 26, 1997.
Marra, M. et al., The WashU–HHMI Mouse EST Project, Accession No. AA498840, dated Jul. 1, 1997.
Marra, M. et al., The WashU–HHMI Mouse EST Project, Accession No. AA636311, dated Oct. 22, 1997.
Marra, M. et al., The WashU–HHMI Mouse EST Project, Accession No. AI050489, dated Jul. 9, 1998.
Marra, M. et al., The WashU–HHMI Mouse EST Project, Accession No. AA921460, dated Apr. 20, 1998.
Marra, M. et al., The WashU–HHMI Mouse EST Project, Accession No. AI466595, dated Mar. 9, 1999.
Marra, M. et al., The WashU–HHMI Mouse EST Project, Accession No. AI287088, dated Nov. 24, 1998.
Marra, M. et al., The WashU–HHMI Mouse EST Project, Accession No. W77540, dated Jun. 20, 1996.
Marra, M. et al., The WashU–HHMI Mouse EST Project, Accession No. AA646983, dated Oct. 28, 1997.
Marra, M. et al., The WashU–HHMI Mouse EST Project, Accession No. AI116725, dated Feb. 13, 1997.
Marra, M. et al., The WashU–HHMI Mouse EST Project, Accession No. AA475668, dated Jun. 18, 1997.
Marra, M. et al., The WashU–HHMI Mouse EST Project, Accession No. AI287088, dated Nov. 24, 1998.
Ko, M.S.H. et al., Systematic analyses of genes expressed in fertilized mouse eggs (The ERATO/Doi Project at Wayne State University), Accession No. C86502, dated Mar. 11, 1998.
Hattori, M. et al., GenPept Accession No. CAB90552, submitted May 5, 2000.
Pietu, G. et al., GenPept Accession No. AAC78827, submitted 1996.
Hayette, S. et al., GenPept Accession No. AAC64321, submitted 1998.
Bauer, H. et al., GenPept Accession No. AAD09175, submitted 1998.
Hemmati–Brivanlou, A. et al., GenPept Accession No. AAB30638, submitted 1994.

(List continued on next page.)

*Primary Examiner*—Lorraine Spector
*Assistant Examiner*—Ruixiang Li
(74) *Attorney, Agent, or Firm*—Ann W. Speckman; Janet Sleath

(57) ABSTRACT

Isolated polynucleotides and polypeptides derived from mammalian fsn -/-lymph node stromal cells are provided, together with expression vectors and host cells comprising such isolated polynucleotides. Methods for the use of such polynucleotides and polypeptides are also provided.

15 Claims, 9 Drawing Sheets

OTHER PUBLICATIONS

Shi, D., GenPept Accession No. CAA53271, submitted Nov. 3, 1993.

Givol, D., GenPept Accession No. CAA41209, submitted Feb. 20, 1991.

Katoh, O. et al., GenPept Accession No. AAB25535, submitted 1993.

Bachner, D. et al., GenPept Accession No. CAB65272, submitted 1999.

Xu, J. et al., GenPept Accession No. AAF03400, submitted 1999.

Cabibbo, A. et al., GenPept Accession No. AAF20364, submitted 2000.

Isogai, T. et al., GenPept Accession No. BAA91786, submitted Feb. 16, 2000.

Wilson, R. et al., GenPept Accession No. AAB42225, submitted 1994.

Riboldi Tunnicliffe, G.R. et al., GenPept Accession No. AAC15584, submitted Sep. 1997.

Bouchon, A. et al., GenPept Accession No. AAF69825, submitted 2000.

Shibata, T., GenPept Accession No. BAA 18909, submitted Apr. 8, 1994.

Jang, W. et al., GenPept Accession No. AAC83205, submitted 1999.

Poutska, A. et al., GenPept Accession No. CAB55955, submitted Sep. 1999.

Dear, T.N. et al., Swiss–Prot Accession No. P1730, submitted 1988.

Coglievina, M. et al., Swiss–Prot Accession No. P53104, submitted 1997.

Weterman, M.A.J. et al., Swiss–Prot Accession No. Q14956, submitted 1995.

Nagpal S. et al., Swiss–Prot Accession No. Q99969, submitted 1997.

Poutska, A. et al., PIR Accession No. T17265, submitted Oct. 15, 1999.

Shi, D.L. et al., PIR Accession No. S38579, submitted Nov. 1993.

Marra, M. et al., The WashU–HHMI Mouse EST Project, Accession No. AA184346, dated Feb. 17, 1997.

* cited by examiner

Fig. 1

```
Signal peptide                                              IgG1 domain
MTRSPALLLLLLGALPSAEAAR / GPPRMADKVVPRQVARLGRTVRLQCPVEGDPPPLTMWTKDGRTIHSGWS
1                    20                        40

RFRVLPQGLKVKEVEAEDAGVYVCKATNGFGSLSVNYTLIIM / DDISPGKESPGPGGSSGGQEDPASQQWAR
                                   102
                                                      IgG2 domain
PRFTQPSKMRRRVIARPVGSSVRLKCVASGHPRPDIMWMKDDQTLTHLEASEHRKKKWTLSLKNLKPEDSG
               161

KYTCRVSNKAGAINATYKVDVIQRTRSKPVLTGTHPVNTTVDFGGTTSFQCKVRSDVKPVIQWLKRVEYGS
           224                              258

EGRHNSTIDVGGQKFVVLPTGDVWSRPDGSYLNKLLISRARQDDAGMYICLGANTMGYSFRSAFLTVLPDP
                                                                    341
             Transmembrane domain
KPPGPPMASSSSSTSLPWPVVIGIPAGAVFILGTVLLWLCQTKKKPCAPASTLPVPGHRPPGTSRERSGDK
          374                     394

DLPSLAVGICEEHGSAMAPQHILASGSTAGPKLYPKLYTDVHTHTHTHTCTHTLSCGGQGSSTPACPLSVL

NTANLQALCPEVGIWGPRQQVGRIENNGGRVS
                              529
```

Underlined: Signal peptide, IgG1 domain, IgG2 domain, Transmembrane domain

Bold, Italics, underlined: Four putative glycosylation sites

Bold, underlined: putative SHP-2 binding site:

/........../ : Splice sites for FGFRγ

Fig. 9
FGFR5β-treated PBMC
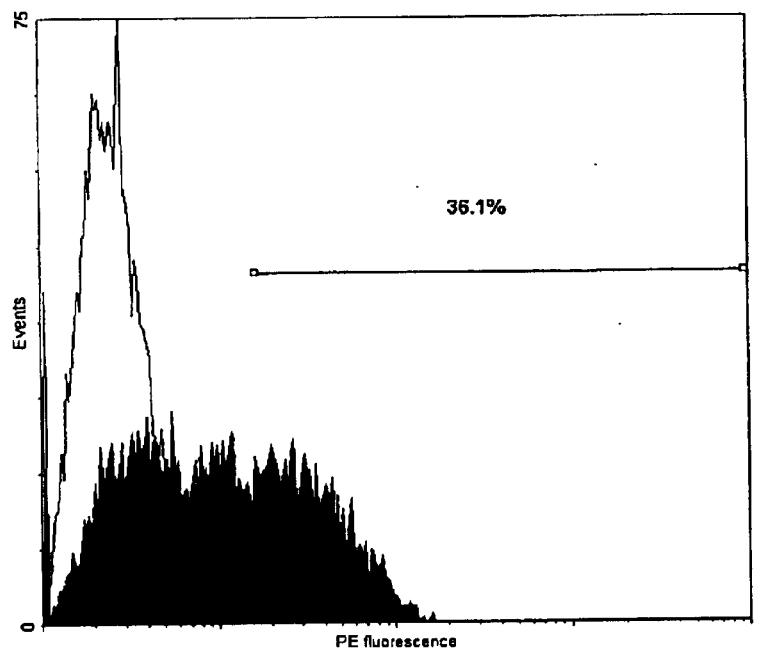
FGFR5γ-treated PBMC
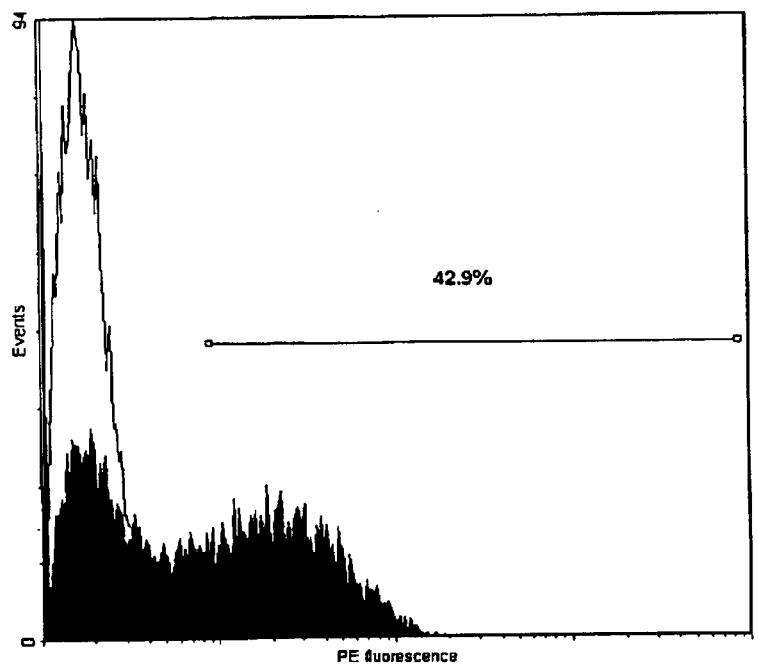

SEQUENCE LISTING

<160> NUMBER OF SEQ ID NOS: 61

<210> SEQ ID NO 1
<211> LENGTH: 803
<212> TYPE: DNA
<213> ORGANISM: Mouse

<400> SEQUENCE: 1

| | | | | | | |
|---|---|---|---|---|---|---|
| gttctgaatg | ggagcatcag | ccctctctgg | gctgttgccc | cgacattaca | ggtcctgtct | 60 |
| ctcagggacg | tgggccttgg | ttctggcgct | gcagagatgg | acttctctgc | gtttgggaat | 120 |
| ctgcgggcgt | tggatctgtc | gggaaactcc | ctgaccagct | tccaaaagtt | caagggcagt | 180 |
| ttggcccttc | ggactctcga | cctccgcaga | aactctctca | cggccctccc | tcagagggtt | 240 |
| gtgtccgagc | agcctctgag | gggtctgcag | accatctacc | tcagccagaa | cccttatgac | 300 |
| tgctgtgggg | tggaaggatg | gggggccctg | cagcagcact | tcaagactgt | tgcggacttg | 360 |
| tccatggtca | cttgcaacct | ctcttccaag | atcgtccgtg | tggtggagct | gcccgaaggc | 420 |
| ctgcctcagg | gctgtaagtg | ggaacaggtg | gacactggtc | tcttctacct | cgtgctcatc | 480 |
| ctgcccagct | gcctcaccct | gctggtggcc | tgtactgtcg | tcttcctcac | ttttaagaag | 540 |
| cctttgcttc | aggtcatcaa | gagccgctgc | cactggtcct | ccatatactg | acccgtgtgc | 600 |
| caaggctaga | gacttggttt | ttcctcgagg | atgcgtctct | ccgctggatc | tttacttttg | 660 |
| caggggtcga | gtgtgatgca | ttgaaggtta | aaactgaaat | ttgaaagagt | tccatcctca | 720 |
| gtcccattaa | cttctcctcc | catccgtgtg | atttatcctc | attgtcctgg | tgaaatattt | 780 |
| attaaacgac | attctgtgag | att | | | | 803 |

<210> SEQ ID NO 2
<211> LENGTH: 689
<212> TYPE: DNA
<213> ORGANISM: Mouse

<400> SEQUENCE: 2

| | | | | | | |
|---|---|---|---|---|---|---|
| gtcgcctgag | gtccccgccg | acgacgcact | caccatggcg | cctgctaacc | ttgggctgac | 60 |
| gccgcactgg | gtgatgctcc | tcggtgccgt | gctgctgttg | cttctgtccg | gagcctccgc | 120 |
| gcaggaacct | ccgagagtgg | gttgctctga | gtacacaaac | agatcctgtg | aagagtgcct | 180 |
| caggaatgtc | tcctgtctgt | ggtgcaatga | gaacaaggcg | tgtatggact | acccagtgag | 240 |
| gaaaatcttg | ccccctgctt | ctctctgtaa | attgagttcc | gctcgctggg | gcgtatgctg | 300 |
| ggtgaacttc | gaggccttga | tcatcaccat | gtcggtcctg | gggggctctg | tgctcctggg | 360 |
| catcactgtg | tgctgctgct | actgctgccg | ccggaagaag | agccggaagc | cagacaagag | 420 |
| cgatgagcgg | gccatgagag | agcaggagga | gaggagagtg | cggcaggagg | aaaggagggc | 480 |
| ggaaatgaag | tcaagacatg | atgaaatcag | gaaaaaatac | ggtctgttta | agaacaaaa | 540 |
| cccgtatgag | aagttctaag | gtggctggca | cacacttgtg | gtggatcgtg | cagttccaga | 600 |
| gtttcctggg | aatgcactcc | ccagcagagc | ctgcagagac | ctcaccacca | tggccaccct | 660 |
| tgacctgggt | gatccctcag | cctctactg | | | | 689 |

<210> SEQ ID NO 3
<211> LENGTH: 619
<212> TYPE: DNA
<213> ORGANISM: Mouse

<400> SEQUENCE: 3

-continued

```
ggcaccaggg aagccctgcc gcggcctgtc ccacagaacc tgcatcctca gatgccgccc      60
tatgcctttg ttcacccacc cttccccctg ccacctgtgc ggcccgtgtt caacaacttc     120
cccatcaaca tgggtcctgt gcccgctccc tatgtccccc ctctgcccaa cgtgcgtgtc     180
aactatgact ttggccacat gcacgtgccc ctggagcaca acctgcccat gcactttggc     240
ccccaaccac ggcatcgctt ctgacaccca aagccctgtc agccgtgccg agtctgtagg     300
agggcccagt ctcatcttct gagtagggt gaaggcctcc attccctctc gaaagtggac      360
gcgtgtcctc ctgctcttac ctttgcaagg tccatgctcc ttcaggtctg atgccctctg     420
ggtgctgatt gtcactgggc aattataggg gcagctccct agtctgccat cttagcagcc     480
aatccagtgg ccctgaccat gaagcaaggc ctctaatcgt ttgccatact tcctccccag     540
cagcccaatg aaagcccagg gggaaatggc ctaccatccc taagccaggg ctctctcctt     600
gttgcccaag gcccactta                                                  619
```

<210> SEQ ID NO 4
<211> LENGTH: 1630
<212> TYPE: DNA
<213> ORGANISM: Mouse

<400> SEQUENCE: 4

```
ggcgcgtgag cctcaggatg aaccctgtgt ttcctagcgg gctgtatggc tctcggtttt      60
tctcaacgct cccgtatggt ggccgcgggt gccggggtga cccggctgct agtgctcttg     120
ctgatggtag ccgcggctcc tagcagagcc cgaggcagcg gctgccgggt cggggcctcc     180
gcgcgtggga ccggggccga tggccgtgaa gctgagggct gtggcaccgt ggctttgctg     240
ctggagcatt catttgagct cggtgatgga gccaacttcc agaagcgagg cttgctgctc     300
tggaaccagc aggatggcac cctgtcggca acacagcgac agctcagtga ggaggagcgt     360
ggccgactcc gggatgtggc tgctgtcaat ggcctctaca gggtccgggt cccgaggcgg     420
cctgggacac ttgatggttc agaagctggc ggccatgtgt cttccttcgt cccagcgtgc     480
tccctggtgg agtcgcacct ttcggaccag ctgaccttgc acgtggatgt ggctggcaac     540
gtggtgggcc tgtctgtggt ggtgtaccct ggggctgcc ggggctccga ggtggaagat      600
gaggacctgg agctgttcaa tacatctgtg cagctgcggc ctcccagcac tgctccaggc     660
cccgagactg cagccttcat tgagcgcctg gagatggagc aggcccagaa ggccaagaac     720
ccacaggagc agaagtcttt ctttgccaaa tactggatgt acatcattcc agttgtgctg     780
ttcctcatga tgtcgggagc gccggacgct gggggccagg gcggcggtgg gggcgggggc     840
agcagccggt gagcagctgt gccacctaga gcccccccca gagccagccc aagaaggagt     900
tcctgacccc acatttccct attgcatgaa tatggaaggc tgtcccttca gtgagccctc     960
tggccttcct gtaagcccct cttttctgtcc ctgagcctct ctctcatcct gttgactgag    1020
agcttgggtg gacctccctg tagccagctc actgcaactg tgtcccacca tgtggcactg    1080
tgctcctctg tctgctaaac acccaccagc ctgccccacc ccaccccacc atacactttg    1140
ggaacttgcc aagctctctc cagcctctgt gcctttgccc tgcaggcccc gtgcgcccct    1200
cactgtcact ctccagccct ttgccaagga tctgtggccc agaggcctct gctcttagtg    1260
gctaggtcag cctccagccc actgtccagg tggcatgctg tcttctttgc cccctctct     1320 ggtgccccag aataccatgg tgacctacca ctatcctttc tgcctttgga tgtcatagcc    1380
tggatctgtc accaggagag gattgtgggc ctccacgtta gtctgtgaat gcacacttcg    1440
```

-continued

```
agtgacttgt gtgcaggttt tgagagccgg ttttgcacta gctgctcgac agctgctggc    1500
atggccgtgc tcttgcacat gcgccgctgt gggcatgggg attgctgtgc agcctcagct    1560
gtgttgtgtg gctgctgatt aaactgtccc ctaaacagca aaaaaaaaaa aaaaaaaaa     1620 aaaaaaaaaa                                                           1630

<210> SEQ ID NO 5
<211> LENGTH: 1197
<212> TYPE: DNA
<213> ORGANISM: Mouse

<400> SEQUENCE: 5
ggcaccagac gactggggcc ctaccccatg tggacaacct caccatgcgt ctggaccccg     60
gtgtgggcgc ctcagtgata ggcgtagtga cagtgacagt gacagctaga gggatgatag    120
acccccaaac tagtggactt tgaagttttc ttcccagccg gttccagcct cctggaacaa    180
ccatgtcgcc agttttgcgc gtgccaaatt cacggcgctg cccaagcgga gctgctatct    240
gaattctcct tggatgtggc aaagggaaat gaacgcaaaa ggtgccgctg aagtgtccg     300 acctagagaa atatgtagac cggagccctg ttaccttcct ccagcatgga cttcctggtt    360
ctcttcttgt tctacttggc cttcttattg atttgtgttg tcctgatctg catcttcaca    420
aaaagccagc gtttgaaggc cgtggtcctt ggaggagcac aggtagcact ggtccttggg    480
tactgcccgg atgtgaatac tgtgttaggt gctagtctgg aaggctcaca agacaagggg    540
atgtgagtct tgtctttaat cctggcactt gggaggctga ggcttcgggg ccagttgggg    600
ctacatcgca agagcctgtg tccaaacaaa caaaacgttg tcttttttgct ttgagatagg    660 tcgaataggt cgaattttca aggttggctt tttaaacagt gtgtaatgtc tgtatttggt    720
tgtgactcct gtttgcctag acatgcttgt agcaggtgtg aactcaggag gacacaagtg    780
accagaaagc tgagcatcta gctgtcaatc ttcccttcac attgtcccat ctgtcttccc    840
ttgggggtca agcaaagtg gggcaagta gccacgaagg ggttgacttg ggaggaccct     900
ggggatctgg aggccaatct tgagcatgga gcagacctga gggttaggga agcccacgtc    960
cacagcagcc tctgcacacc ccctttcccc acagactcca acagacacat tctgtgcagt    1020
caaggtagaa atggaggtgt tctctacacc tcctaaatcc tagcacttag gaagctgagg    1080
caggattatg aattccaggc tagctcgggt tatgtaatga gactgtttca aacacagagc    1140
ggagccgagg agatggctgg gcagtcacag agctgccgtg caaccagaac tggaggg       1197

<210> SEQ ID NO 6
<211> LENGTH: 1435
<212> TYPE: DNA
<213> ORGANISM: Mouse
<220> FEATURE:
<221> NAME/KEY: misc_feature
<222> LOCATION: (1)...(1435)
<223> OTHER INFORMATION: n = A,T,C or G

<400> SEQUENCE: 6
catgggcgcc gtctggtcag ccctgctggt cggcggggt ctagctggag cgctcatcct      60
gtggctgctg cggggagact ctggggcccc ggggaaagac ggggttgcgg agccgccgca    120
gaagggcgca cctcctgggg aggctgcggc ccgggagac ggtccgggtg gtggtggcag    180 tgcggcctg agccctgaac cttccgatcg ggagctggtc tccaaagcag agcatcttcg    240
agaaagcaac ggcacatttga tttctgagag caaagatctt ggtaacctgc cggaagcaca    300
gcggctgcag aatgttggag cagactgggt caatgccaga gagtttgttc ctgttgggaa    360
```

-continued

```
gattccagac acacactcca gggccgactc tgaagcggca agaaatcaaa gcccaggatc      420
tcatggagga gaatggagac tccccaaagg acaagaaaca gctgtcaaag tagctggcag      480
tgtggccgca aagctggcct ccagcagcct gcttgtggac agagctaaag cagtcagtca      540
ggaccaggca ggccacgagg actgggaagt ggtgtctagg cactcatctt ggggagtgt       600 tggtttgggt ggcagtcttg aggcttctag gttaagtcta aatcagagaa tggacgacag      660
cacaaacagt cttgtgggag aagaggctg ggaagtagat gggaaagtgg catctctgaa       720
acctcaacag gtcagcatcc agttccaggt gcactacacc acaaacaccg atgtgcagtt      780
cattgcagtg actggagacc atgagagcct gggagatgg aacacataca tcccactcca       840
ctactgcaaa gacgggctct ggtctcattc tgtcttcctg cctgcagaca cagtggtgga      900
gtggaagttc gtgttggtag agaataagga agttactcgt tgggaagaat gcagcaatag      960
attcctgcag actggccatg aggataaagt ggttcatggg tggtggggga ttcactgact     1020
cagttttcag agcatccaag aggctgcagc agaatgtgga caaggctaag gctttagagc     1080
gcactgcata gcttaaagta aaggcggtgt gattccaatt gtagccatca gggctctttc     1140
agatttgcta gtgtggcttt tgtccaaaat gtaggaagat gtatgcctgc agataatgct     1200
tcctgtaanc tggcacttgt cccttattgt attgactggt tgtgctgac acatcaggac      1260 ttgaggaatt gatcatcctg ggtagttgca tcttgggtag tacacctgag gtatggacta     1320
catatgggca aggagcaact aagcaactgc acgggtacaa ggtagagcgc ccttagcagc     1380
tcttagacta gaaagactac aataagcccc atcaaacaca gctaaagcaa cactg          1435

<210> SEQ ID NO 7
<211> LENGTH: 1131
<212> TYPE: DNA
<213> ORGANISM: Mouse

<400> SEQUENCE: 7
ggcaccagcc cggcttctgt gctccgctca gtctccagcg atccctccct acctccgccc       60
tccatggcgt cgctcctgtg ctgtgggcct aagctggccg cctgtggcat cgtcctcagc      120
gcctggggag tgatcatgtt gataatgctc gggatatttt caatgtccaa ttctgctgtg      180
ttaattgagg acgttccctt cacagagaaa gattttgaga acgtcctca gaacatatac       240 aacctgtacg agcaagtcag ctacaactgt ttcatcgccg cgggcctcta cctcctcctc      300
ggaggcttct ccttctgcca agttcgtctc aacaagcgca aggaatacat ggtgcgctag      360
agcgcggtcc gcctctcct ccccagcccc cttctctatt taaagactcc gcagactccg      420
tcccactcat ctggcgtcct ttgggacttg tgaccctagc gagacgtcat ccctggccct      480
gcaaaactgc gcccagcctc tggaggagac cgagggtgac cgcgcccgt tctgaactac       540 aataaaaaga agcggttccc cctaagcttg ctgtctgtgc tttcagggag gggcgggccc      600
gggctggaag gggctgagac cggcctcatc gaggagtccg gaccctccga cggaagtgga     660
atgaagctag ccggaagtga agcaacgtct tccacctcgt cttcctccgc gcggcgaggc      720 ccttgagtg actggggaga ggtcgggtct cggccaatca gctgcaggga gggcgggact      780
ttctgcgcgg gagcccgagc ggccggctgc cgggctctcc gtggtttcca gctcgcgtgg      840
tggtggtggc ggcggagcgt ctccgtgagg aggtgcgcgg ggccatgacg tcagcgtcca      900
ccaaggttgg agagatcttc tccgcggccg gcgccgcctt cacgaagctc ggggagttga     960
cgatgcagct gcatccagtc tcggactctt cccctgccgg tgccaagtgg acggagacgg    1020
```

-continued

| | |
|---|---|
| agatagagat gctgagggct gctgtgaagc gctttgggga cgatcttaat cacatcagct | 1080 |
| gtgtcatcaa ggaacggaca gtggctcaga taaagaccac tgtgaagcga a | 1131 |

<210> SEQ ID NO 8
<211> LENGTH: 1357
<212> TYPE: DNA
<213> ORGANISM: Mouse

<400> SEQUENCE: 8

| | |
|---|---|
| gggagggcct ggaggccgag gcgggcaggc accagccaga gcagctggcg gcagacggca | 60 |
| ggcagacagt cagaccgtct agcgggcctg gcttgcctac ctggcagctg cacccggtcc | 120 |
| ttcacccaga gctggttcca tagctcaaca tggtcccctg gttcctcctg tctctgctgc | 180 |
| tacttgcgag gcctgtgcct ggggtggcct actctgtgtc actcccggcc tccttcctgg | 240 |
| aggatgtagc cggcagcggg gaagctgagg gttcttcagc ctcttcccg agcctgccgc | 300 |
| cgcctgggac tccagccttc agtcccacac cggagagacc ccagcccaca gctctggacg | 360 |
| gccccgtgcc acccaccaac ctcctggaag ggatcatgga tttcttccgg cagtacgtga | 420 |
| tgctcatcgc ggtggtgggc tcgctgacct tcctcatcat gttcatagtc tgcgccgccc | 480 |
| tcatcacgcg ccagaagcac aaggccacag cctactaccc atcctcgttc cctgaaaaga | 540 |
| agtatgtgga ccagagagac cgggctgggg gaccccgtac cttcagcgag gtccctgaca | 600 |
| gggcacctga cagccggcat gaagaaggcc tggacacctc ccatcagctc caggctgaca | 660 |
| ttctggctgc tacccagaac ctccggtctc cagctagagc cctgccaggc aatggggagg | 720 |
| gagcaaagcc tgtgaagggt gggtcggagg aggaggagga agaggtgctc agcggtcagg | 780 |
| aggaggccca ggaagcccca gtatgtgggg tcactgaaga gaagctgggg gtcccagagg | 840 |
| agtcggtctc agcagaggct gaaggggttc ctgccaccag tgagggccaa ggggaagcag | 900 |
| aagggtcttt ctccttagcc caggaatccc agggagcaac tggtcctcct gaaagtccct | 960 |
| gtgcctgcaa cagagtctcc cccagtgtct aacaggcccc agaactgctg ggacccgaat | 1020 |
| gttgggtcct tgagggtcac ctctttggtc aagaaaggca ttcagctcta actgctcctt | 1080 |
| gataccacgt ggcttggcca ttgctggtgc caaggctgac cccgaactgg cagagccgat | 1140 |
| gccctctggt gcaccccagg aaacatctcc ccaagttcca gcgcccttaa tgactcttgc | 1200 |
| caccctgggg gcttcaccct aacgcaccac ttctctggaa ggggaaggcc agacacatgc | 1260 |
| cagttgggc tgcatgaggc agtcctcaga gcagaagggg accaggccag aggccacctg | 1320 |
| tgacgggca aactgcatct cggctgtgga gaccaga | 1357 |

<210> SEQ ID NO 9
<211> LENGTH: 815
<212> TYPE: DNA
<213> ORGANISM: Mouse

<400> SEQUENCE: 9

| | |
|---|---|
| aggtcgacac tagtggatcc aaagaattcg gcacgagggg acgcggagcg gtcgcgtgcg | 60 |
| cggagagcag ctctgggcgc cggcggttg ctgcgggcgc tcaggggccc tgggaacaat | 120 |
| ggcgctgtgc gcgcgggccg cgctgctgct gggcgtgctg caggtgctgg cgctgctagg | 180 |
| ggcggcgcag gaccccgaccg acgctcaggg ctctgcaagt ggaaaccact cagtgctgac | 240 |
| ctccaatatt aacataacag agaataccaa ccagaccatg agtgtggttt ccaaccagac | 300 |
| cagtgaaatg cagagcaccg cgaagccttc cgtactgcca aaaactacca cacttatcac | 360 |
| tgtgaaacct gcaactattg ttaaaatatc aaccccagga gtcttaccac atgtgacgcc | 420 |

```
tactgcctca aagtctacac ccaatgcaag tgcttctcca aactctaccc acacgtcagc      480
atccatgaca accccagccc acagtagttt attgacaact gtaacggttt cagcaactac      540
tcatcccacc aaaggcaaag gatccaagtt tgatgccggc agctttgttg gtggtatagg      600
tgttaacact gggagtttta tctattctct acattggatg caaaatgtat tattcaagaa      660
gaggcattcg gtaccgaagc attgacgaac atgatgccat catttaaagt acttcagtgg      720
tcaaggaaag aagaaagact gcagccttat caattatttt ggtttatatt agtttaaact      780
attattttct tggaagtagt ataaacaagt catgc                                 815

<210> SEQ ID NO 10
<211> LENGTH: 1129
<212> TYPE: DNA
<213> ORGANISM: Mouse

<400> SEQUENCE: 10
ccaacactcg ccatgcgttc tggggcactg tggccgctgc tttggggagc cctggtctgg       60
acagtgggat ccgtgggcgc cgtgatgggc tccgaggatt ctgtgcccgg tggcgtgtgc      120
tggctccagc agggcagaga ggccacctgc agtctggtgc tgaagactcg tgtcagccgg      180
gaggagtgct gtgcttccgg caacatcaac accgcctggt ccaacttcac ccacccaggc      240
aataaaatca gcctgctagg gttcctgggc ctcgtccact gcctcccctg caaagattcc      300
tgcgacggag tggagtgcgg ccccggcaag gcgtgccgca atgctggggg ggcgtccaac      360
aactgcgagt gcgtgcccaa ctgcgagggg tttcccgcgg gcttccaggt ctgcggctct      420
gatggcgcca cctaccggga cgaatgcgaa ctgcgcaccg cgcgctgtcg cggacaccca      480
gacttgcgcg tcatgtaccg cggccgctgt caaaagtctt gcgctcaggt agtgtgcccg      540
cgtccccagt cgtgccttgt ggatcagacc ggcagcgcac actgcgtggt gtgtcgcgct      600
gcgccctgcc cagtaccttc caaccccggc caagaactct gtggcaacaa caacgttacc      660
tacatctcgt cgtgtcacct gcgccaggcc acttgcttcc tgggccgctc cattgggggtt      720 cggcacccag gcatctgcac aggtggcccc aagttcctga gtctggcga tgctgccatt      780 gttgatatgg tccctggcaa gcccatgtgt gttgagagct ctctgactac ccctccactt      840
ggtcgctttg ctgttcgtga catgaggcag acagttgctg tgggtgtcat caaagctgtg      900
gacaagaagg ctgctggagc tggcaaagtc accaagtctg cccagaaagc tcagaaggct      960
aaatgaatat taccccctaac acctgccacc ccagtcttaa tcagtggtgg aagaacggtc     1020
tcagaactgt ttgtctcaat tggccattta agtttaatag taaaagactg gttaatgata     1080
acaatgcatc gtaaaacctt cagaaggaaa gaatgttgtg gaccatttt                  1129

<210> SEQ ID NO 11
<211> LENGTH: 196
<212> TYPE: PRT
<213> ORGANISM: Mouse

<400> SEQUENCE: 11

Val Leu Asn Gly Ser Ile Ser Pro Leu Trp Ala Val Ala Pro Thr Leu
  1               5                  10                  15

Gln Val Leu Ser Leu Arg Asp Val Gly Leu Gly Ser Gly Ala Ala Glu
                 20                  25                  30

Met Asp Phe Ser Ala Phe Gly Asn Leu Arg Ala Leu Asp Leu Ser Gly
             35                  40                  45

Asn Ser Leu Thr Ser Phe Gln Lys Phe Lys Gly Ser Leu Ala Leu Arg
```

```
                50                  55                  60
Thr Leu Asp Leu Arg Arg Asn Ser Leu Thr Ala Leu Pro Gln Arg Val
 65                  70                  75                  80

Val Ser Glu Gln Pro Leu Arg Gly Leu Gln Thr Ile Tyr Leu Ser Gln
                 85                  90                  95

Asn Pro Tyr Asp Cys Cys Gly Val Glu Gly Trp Gly Ala Leu Gln Gln
                100                 105                 110

His Phe Lys Thr Val Ala Asp Leu Ser Met Val Thr Cys Asn Leu Ser
            115                 120                 125

Ser Lys Ile Val Arg Val Glu Leu Pro Glu Gly Leu Pro Gln Gly
130                 135                 140

Cys Lys Trp Glu Gln Val Asp Thr Gly Leu Phe Tyr Leu Val Leu Ile
145                 150                 155                 160

Leu Pro Ser Cys Leu Thr Leu Val Ala Cys Thr Val Val Phe Leu
                165                 170                 175

Thr Phe Lys Lys Pro Leu Leu Gln Val Ile Lys Ser Arg Cys His Trp
            180                 185                 190

Ser Ser Ile Tyr
            195

<210> SEQ ID NO 12
<211> LENGTH: 174
<212> TYPE: PRT
<213> ORGANISM: Mouse

<400> SEQUENCE: 12

Met Ala Pro Ala Asn Leu Gly Leu Thr Pro His Trp Val Met Leu Leu
 1               5                  10                  15

Gly Ala Val Leu Leu Leu Leu Ser Gly Ala Ser Ala Gln Glu Pro
                 20                  25                  30

Pro Arg Val Gly Cys Ser Glu Tyr Thr Asn Arg Ser Cys Glu Glu Cys
             35                  40                  45

Leu Arg Asn Val Ser Cys Leu Trp Cys Asn Glu Asn Lys Ala Cys Met
 50                  55                  60

Asp Tyr Pro Val Arg Lys Ile Leu Pro Pro Ala Ser Leu Cys Lys Leu
 65                  70                  75                  80

Ser Ser Ala Arg Trp Gly Val Cys Trp Val Asn Phe Glu Ala Leu Ile
                 85                  90                  95

Ile Thr Met Ser Val Leu Gly Gly Ser Val Leu Leu Gly Ile Thr Val
                100                 105                 110

Cys Cys Cys Tyr Cys Cys Arg Arg Lys Lys Ser Arg Lys Pro Asp Lys
            115                 120                 125

Ser Asp Glu Arg Ala Met Arg Glu Gln Glu Arg Arg Val Arg Gln
130                 135                 140

Glu Glu Arg Arg Ala Glu Met Lys Ser Arg His Asp Glu Ile Arg Lys
145                 150                 155                 160

Lys Tyr Gly Leu Phe Lys Glu Gln Asn Pro Tyr Glu Lys Phe
                165                 170

<210> SEQ ID NO 13
<211> LENGTH: 106
<212> TYPE: PRT
<213> ORGANISM: Mouse

<400> SEQUENCE: 13

Ala Pro Gly Lys Pro Cys Arg Gly Leu Ser His Arg Thr Cys Ile Leu
```

```
            1               5                   10                  15
Arg Cys Arg Pro Met Pro Leu Phe Thr His Pro Ser Pro Cys His Leu
                20                  25                  30

Cys Gly Pro Cys Ser Thr Thr Ser Pro Ser Thr Trp Val Leu Cys Pro
                35                  40                  45

Leu Pro Met Ser Pro Leu Cys Pro Thr Cys Val Ser Thr Met Thr Leu
            50                  55                  60

Ala Thr Cys Thr Cys Pro Trp Ser Thr Thr Cys Pro Cys Thr Leu Ala
65                  70                  75                  80

Pro Asn His Gly Ile Ala Ser Asp Thr Gln Ser Pro Val Ser Arg Ala
                85                  90                  95

Glu Ser Val Gly Gly Pro Ser Leu Ile Phe
                100                 105

<210> SEQ ID NO 14
<211> LENGTH: 268
<212> TYPE: PRT
<213> ORGANISM: Mouse

<400> SEQUENCE: 14

Met Ala Leu Gly Phe Ser Gln Arg Ser Arg Met Val Ala Ala Gly Ala
1               5                   10                  15

Gly Val Thr Arg Leu Leu Val Leu Leu Leu Met Val Ala Ala Ala Pro
                20                  25                  30

Ser Arg Ala Arg Gly Ser Gly Cys Arg Val Gly Ala Ser Ala Arg Gly
            35                  40                  45

Thr Gly Ala Asp Gly Arg Glu Ala Glu Gly Cys Gly Thr Val Ala Leu
        50                  55                  60

Leu Leu Glu His Ser Phe Glu Leu Gly Asp Gly Ala Asn Phe Gln Lys
65                  70                  75                  80

Arg Gly Leu Leu Leu Trp Asn Gln Gln Asp Gly Thr Leu Ser Ala Thr
                85                  90                  95

Gln Arg Gln Leu Ser Glu Glu Arg Gly Arg Leu Arg Asp Val Ala
            100                 105                 110

Ala Val Asn Gly Leu Tyr Arg Val Arg Val Pro Arg Arg Pro Gly Thr
        115                 120                 125

Leu Asp Gly Ser Glu Ala Gly Gly His Val Ser Phe Val Pro Ala
    130                 135                 140

Cys Ser Leu Val Glu Ser His Leu Ser Asp Gln Leu Thr Leu His Val
145                 150                 155                 160

Asp Val Ala Gly Asn Val Val Gly Leu Ser Val Val Tyr Pro Gly
                165                 170                 175

Gly Cys Arg Gly Ser Glu Val Glu Asp Glu Asp Leu Glu Leu Phe Asn
            180                 185                 190

Thr Ser Val Gln Leu Arg Pro Pro Ser Thr Ala Pro Gly Pro Glu Thr
        195                 200                 205

Ala Ala Phe Ile Glu Arg Leu Glu Met Glu Gln Ala Gln Lys Ala Lys
    210                 215                 220

Asn Pro Gln Glu Gln Lys Ser Phe Phe Ala Lys Tyr Trp Met Tyr Ile
225                 230                 235                 240

Ile Pro Val Val Leu Phe Leu Met Met Ser Gly Ala Pro Asp Ala Gly
                245                 250                 255

Gly Gln Gly Gly Gly Gly Gly Gly Ser Ser Arg
            260                 265
```

-continued

```
<210> SEQ ID NO 15
<211> LENGTH: 66
<212> TYPE: PRT
<213> ORGANISM: Mouse

<400> SEQUENCE: 15
```

| Met | Asp | Phe | Leu | Val | Leu | Phe | Leu | Phe | Tyr | Leu | Ala | Phe | Leu | Leu | Ile |
|---|---|---|---|---|---|---|---|---|---|---|---|---|---|---|---|
| 1 | | | | 5 | | | | | 10 | | | | | 15 | |

| Cys | Val | Val | Leu | Ile | Cys | Ile | Phe | Thr | Lys | Ser | Gln | Arg | Leu | Lys | Ala |
|---|---|---|---|---|---|---|---|---|---|---|---|---|---|---|---|
| | | | 20 | | | | | 25 | | | | | 30 | | |

| Val | Val | Leu | Gly | Gly | Ala | Gln | Val | Ala | Leu | Val | Leu | Gly | Tyr | Cys | Pro |
|---|---|---|---|---|---|---|---|---|---|---|---|---|---|---|---|
| | | 35 | | | | | 40 | | | | | 45 | | | |

| Asp | Val | Asn | Thr | Val | Leu | Gly | Ala | Ser | Leu | Glu | Gly | Ser | Gln | Asp | Lys |
|---|---|---|---|---|---|---|---|---|---|---|---|---|---|---|---|
| | 50 | | | | | 55 | | | | | 60 | | | | |

| Gly | Met |
|---|---|
| 65 | |

```
<210> SEQ ID NO 16
<211> LENGTH: 338
<212> TYPE: PRT
<213> ORGANISM: Mouse

<400> SEQUENCE: 16
```

| Met | Gly | Ala | Val | Trp | Ser | Ala | Leu | Leu | Val | Gly | Gly | Leu | Ala | Gly |
|---|---|---|---|---|---|---|---|---|---|---|---|---|---|---|
| 1 | | | | 5 | | | | | 10 | | | | | 15 |

| Ala | Leu | Ile | Leu | Trp | Leu | Leu | Arg | Gly | Asp | Ser | Gly | Ala | Pro | Gly | Lys |
|---|---|---|---|---|---|---|---|---|---|---|---|---|---|---|---|
| | | | 20 | | | | | 25 | | | | | 30 | | |

| Asp | Gly | Val | Ala | Glu | Pro | Pro | Gln | Lys | Gly | Ala | Pro | Gly | Glu | Ala |
|---|---|---|---|---|---|---|---|---|---|---|---|---|---|---|
| | | 35 | | | | | 40 | | | | | 45 | | | |

| Ala | Ala | Pro | Gly | Asp | Gly | Pro | Gly | Gly | Gly | Ser | Gly | Gly | Leu | Ser |
|---|---|---|---|---|---|---|---|---|---|---|---|---|---|---|
| | 50 | | | | | 55 | | | | | 60 | | | | |

| Pro | Glu | Pro | Ser | Asp | Arg | Glu | Leu | Val | Ser | Lys | Ala | Glu | His | Leu | Arg |
|---|---|---|---|---|---|---|---|---|---|---|---|---|---|---|---|
| 65 | | | | | 70 | | | | | 75 | | | | | 80 |

| Glu | Ser | Asn | Gly | His | Leu | Ile | Ser | Glu | Ser | Lys | Asp | Leu | Gly | Asn | Leu |
|---|---|---|---|---|---|---|---|---|---|---|---|---|---|---|---|
| | | | | 85 | | | | | 90 | | | | | 95 | |

| Pro | Glu | Ala | Gln | Arg | Leu | Gln | Asn | Val | Gly | Ala | Asp | Trp | Val | Asn | Ala |
|---|---|---|---|---|---|---|---|---|---|---|---|---|---|---|---|
| | | | 100 | | | | | 105 | | | | | 110 | | |

| Arg | Glu | Phe | Val | Pro | Val | Gly | Lys | Ile | Pro | Asp | Thr | His | Ser | Arg | Ala |
|---|---|---|---|---|---|---|---|---|---|---|---|---|---|---|---|
| | | 115 | | | | | 120 | | | | | 125 | | | |

| Asp | Ser | Glu | Ala | Ala | Arg | Asn | Gln | Ser | Pro | Gly | Ser | His | Gly | Gly | Glu |
|---|---|---|---|---|---|---|---|---|---|---|---|---|---|---|---|
| | 130 | | | | | 135 | | | | | 140 | | | | |

| Trp | Arg | Leu | Pro | Lys | Gly | Gln | Glu | Thr | Ala | Val | Lys | Val | Ala | Gly | Ser |
|---|---|---|---|---|---|---|---|---|---|---|---|---|---|---|---|
| 145 | | | | | 150 | | | | | 155 | | | | | 160 |

| Val | Ala | Ala | Lys | Leu | Ala | Ser | Ser | Ser | Leu | Leu | Val | Asp | Arg | Ala | Lys |
|---|---|---|---|---|---|---|---|---|---|---|---|---|---|---|---|
| | | | | 165 | | | | | 170 | | | | | 175 | |

| Ala | Val | Ser | Gln | Asp | Gln | Ala | Gly | His | Glu | Asp | Trp | Glu | Val | Val | Ser |
|---|---|---|---|---|---|---|---|---|---|---|---|---|---|---|---|
| | | | 180 | | | | | 185 | | | | | 190 | | |

| Arg | His | Ser | Ser | Trp | Gly | Ser | Val | Gly | Leu | Gly | Gly | Ser | Leu | Glu | Ala |
|---|---|---|---|---|---|---|---|---|---|---|---|---|---|---|---|
| | | 195 | | | | | 200 | | | | | 205 | | | |

| Ser | Arg | Leu | Ser | Leu | Asn | Gln | Arg | Met | Asp | Asp | Ser | Thr | Asn | Ser | Leu |
|---|---|---|---|---|---|---|---|---|---|---|---|---|---|---|---|
| | 210 | | | | | 215 | | | | | 220 | | | | |

| Val | Gly | Gly | Arg | Gly | Trp | Glu | Val | Asp | Gly | Lys | Val | Ala | Ser | Leu | Lys |
|---|---|---|---|---|---|---|---|---|---|---|---|---|---|---|---|
| 225 | | | | | 230 | | | | | 235 | | | | | 240 |

| Pro | Gln | Gln | Val | Ser | Ile | Gln | Phe | Gln | Val | His | Tyr | Thr | Thr | Asn | Thr |
|---|---|---|---|---|---|---|---|---|---|---|---|---|---|---|---|
| | | | | 245 | | | | | 250 | | | | | 255 | |

-continued

```
Asp Val Gln Phe Ile Ala Val Thr Gly Asp His Glu Ser Leu Gly Arg
            260                 265                 270

Trp Asn Thr Tyr Ile Pro Leu His Tyr Cys Lys Asp Gly Leu Trp Ser
        275                 280                 285

His Ser Val Phe Leu Pro Ala Asp Thr Val Val Glu Trp Lys Phe Val
    290                 295                 300

Leu Val Glu Asn Lys Glu Val Thr Arg Trp Glu Glu Cys Ser Asn Arg
305                 310                 315                 320

Phe Leu Gln Thr Gly His Glu Asp Lys Val Val His Gly Trp Trp Gly
                325                 330                 335

Ile His

<210> SEQ ID NO 17
<211> LENGTH: 119
<212> TYPE: PRT
<213> ORGANISM: Mouse

<400> SEQUENCE: 17

Gly Thr Ser Pro Ala Ser Val Leu Arg Ser Val Ser Ser Asp Pro Ser
1               5                   10                  15

Leu Pro Pro Pro Ser Met Ala Ser Leu Leu Cys Cys Gly Pro Lys Leu
            20                  25                  30

Ala Ala Cys Gly Ile Val Leu Ser Ala Trp Gly Val Ile Met Leu Ile
        35                  40                  45

Met Leu Gly Ile Phe Phe Asn Val His Ser Ala Val Leu Ile Glu Asp
    50                  55                  60

Val Pro Phe Thr Glu Lys Asp Phe Glu Asn Gly Pro Gln Asn Ile Tyr
65                  70                  75                  80

Asn Leu Tyr Glu Gln Val Ser Tyr Asn Cys Phe Ile Ala Ala Gly Leu
                85                  90                  95

Tyr Leu Leu Leu Gly Gly Phe Ser Phe Cys Gln Val Arg Leu Asn Lys
            100                 105                 110

Arg Lys Glu Tyr Met Val Arg
        115

<210> SEQ ID NO 18
<211> LENGTH: 280
<212> TYPE: PRT
<213> ORGANISM: Mouse

<400> SEQUENCE: 18

Met Val Pro Trp Phe Leu Ser Leu Leu Leu Ala Arg Pro Val
1               5                   10                  15

Pro Gly Val Ala Tyr Ser Val Ser Leu Pro Ala Ser Phe Leu Glu Asp
            20                  25                  30

Val Ala Gly Ser Gly Glu Ala Glu Gly Ser Ser Ala Ser Ser Pro Ser
        35                  40                  45

Leu Pro Pro Pro Gly Thr Pro Ala Phe Ser Pro Thr Pro Glu Arg Pro
    50                  55                  60

Gln Pro Thr Ala Leu Asp Gly Pro Val Pro Thr Asn Leu Leu Glu
65                  70                  75                  80

Gly Ile Met Asp Phe Phe Arg Gln Tyr Val Met Leu Ile Ala Val Val
                85                  90                  95

Gly Ser Leu Thr Phe Leu Ile Met Phe Ile Val Cys Ala Ala Leu Ile
            100                 105                 110

Thr Arg Gln Lys His Lys Ala Thr Ala Tyr Tyr Pro Ser Ser Phe Pro
```

```
            115                 120                 125
Glu Lys Lys Tyr Val Asp Gln Arg Asp Arg Ala Gly Gly Pro Arg Thr
    130                 135                 140

Phe Ser Glu Val Pro Asp Arg Ala Pro Asp Ser Arg His Glu Glu Gly
145                 150                 155                 160

Leu Asp Thr Ser His Gln Leu Gln Ala Asp Ile Leu Ala Ala Thr Gln
                165                 170                 175

Asn Leu Arg Ser Pro Ala Arg Ala Leu Pro Gly Asn Gly Glu Gly Ala
            180                 185                 190

Lys Pro Val Lys Gly Ser Glu Glu Glu Glu Val Leu Ser
        195                 200                 205

Gly Gln Glu Glu Ala Gln Glu Ala Pro Val Cys Gly Val Thr Glu Glu
    210                 215                 220

Lys Leu Gly Val Pro Glu Glu Ser Val Ser Ala Glu Ala Glu Gly Val
225                 230                 235                 240

Pro Ala Thr Ser Glu Gly Gln Gly Glu Ala Glu Gly Ser Phe Ser Leu
                245                 250                 255

Ala Gln Glu Ser Gln Gly Ala Thr Gly Pro Pro Glu Ser Pro Cys Ala
            260                 265                 270

Cys Asn Arg Val Ser Pro Ser Val
        275                 280

<210> SEQ ID NO 19
<211> LENGTH: 188
<212> TYPE: PRT
<213> ORGANISM: Mouse

<400> SEQUENCE: 19

Met Ala Leu Cys Ala Arg Ala Ala Leu Leu Leu Gly Val Leu Gln Val
1               5                   10                  15

Leu Ala Leu Leu Gly Ala Ala Gln Asp Pro Thr Asp Ala Gln Gly Ser
            20                  25                  30

Ala Ser Gly Asn His Ser Val Leu Thr Ser Asn Ile Asn Ile Thr Glu
        35                  40                  45

Asn Thr Asn Gln Thr Met Ser Val Val Ser Asn Gln Thr Ser Glu Met
    50                  55                  60

Gln Ser Thr Ala Lys Pro Ser Val Leu Pro Lys Thr Thr Thr Leu Ile
65                  70                  75                  80

Thr Val Lys Pro Ala Thr Ile Val Lys Ile Ser Thr Pro Gly Val Leu
                85                  90                  95

Pro His Val Thr Pro Thr Ala Ser Lys Ser Thr Pro Asn Ala Ser Ala
            100                 105                 110

Ser Pro Asn Ser Thr His Thr Ser Ala Ser Met Thr Thr Pro Ala His
        115                 120                 125

Ser Ser Leu Leu Thr Thr Val Thr Val Ser Ala Thr Thr His Pro Thr
    130                 135                 140

Lys Gly Lys Gly Ser Lys Phe Asp Ala Gly Ser Phe Val Gly Gly Ile
145                 150                 155                 160

Gly Val Asn Thr Gly Ser Phe Ile Tyr Ser Leu His Trp Met Gln Asn
                165                 170                 175

Val Leu Phe Lys Lys Arg His Ser Val Pro Lys His
            180                 185

<210> SEQ ID NO 20
<211> LENGTH: 317
```

<212> TYPE: PRT
<213> ORGANISM: Mouse

<400> SEQUENCE: 20

```
Met Arg Ser Gly Ala Leu Trp Pro Leu Leu Trp Gly Ala Leu Val Trp
 1               5                  10                  15

Thr Val Gly Ser Val Gly Ala Val Met Gly Ser Glu Asp Ser Val Pro
                20                  25                  30

Gly Gly Val Cys Trp Leu Gln Gln Gly Arg Glu Ala Thr Cys Ser Leu
            35                  40                  45

Val Leu Lys Thr Arg Val Ser Arg Glu Glu Cys Cys Ala Ser Gly Asn
 50                  55                  60

Ile Asn Thr Ala Trp Ser Asn Phe Thr His Pro Gly Asn Lys Ile Ser
 65                  70                  75                  80

Leu Leu Gly Phe Leu Gly Leu Val His Cys Leu Pro Cys Lys Asp Ser
                85                  90                  95

Cys Asp Gly Val Glu Cys Gly Pro Gly Lys Ala Cys Arg Asn Ala Gly
            100                 105                 110

Gly Ala Ser Asn Asn Cys Glu Cys Val Pro Asn Cys Glu Gly Phe Pro
        115                 120                 125

Ala Gly Phe Gln Val Cys Gly Ser Asp Gly Ala Thr Tyr Arg Asp Glu
130                 135                 140

Cys Glu Leu Arg Thr Ala Arg Cys Arg Gly His Pro Asp Leu Arg Val
145                 150                 155                 160

Met Tyr Arg Gly Arg Cys Gln Lys Ser Cys Ala Gln Val Val Cys Pro
                165                 170                 175

Arg Pro Gln Ser Cys Leu Val Asp Gln Thr Gly Ser Ala His Cys Val
            180                 185                 190

Val Cys Arg Ala Ala Pro Cys Pro Val Pro Ser Asn Pro Gly Gln Glu
        195                 200                 205

Leu Cys Gly Asn Asn Asn Val Thr Tyr Ile Ser Ser Cys His Leu Arg
210                 215                 220

Gln Ala Thr Cys Phe Leu Gly Arg Ser Ile Gly Val Arg His Pro Gly
225                 230                 235                 240

Ile Cys Thr Gly Gly Pro Lys Phe Leu Lys Ser Gly Asp Ala Ala Ile
                245                 250                 255

Val Asp Met Val Pro Gly Lys Pro Met Cys Val Glu Ser Phe Ser Asp
            260                 265                 270

Tyr Pro Pro Leu Gly Arg Phe Ala Val Arg Asp Met Arg Gln Thr Val
        275                 280                 285

Ala Val Gly Val Ile Lys Ala Val Asp Lys Lys Ala Ala Gly Ala Gly
        290                 295                 300

Lys Val Thr Lys Ser Ala Gln Lys Ala Gln Lys Ala Lys
305                 310                 315
```

<210> SEQ ID NO 21
<211> LENGTH: 384
<212> TYPE: DNA
<213> ORGANISM: Mouse
<220> FEATURE:
<221> NAME/KEY: misc_feature
<222> LOCATION: (1)...(384)
<223> OTHER INFORMATION: n = A,T,C or G

<400> SEQUENCE: 21
ggtggacttc ggtgggacaa cgtccttcca gtgcaaggtg cgcagtgacg tgaagcctgt    60

| | |
|---|---|
| gatccagtgg ctgaagcggg tggagtacgg ctccgaggga cgccacaact ccaccattga | 120 |
| tgtgggtggc cagaagtttg tggtgttgcc cacgggtgat gtgtggtcac ggcctgatgg | 180 |
| ctcctacctc aacaagctgc tcatctctcg ggcccgccag gatgatgctg gcatgtacat | 240 |
| ctgcctaggt gcaaatacca tgggctacag tttccgtagc gccttcctca ctgtattacc | 300 |
| agaccccaaa cctccagggc ctcctatggc ttcttcatcg tcatccacaa gcctgccatg | 360 |
| gcctgtggng atcggcatcc cagc | 384 |

<210> SEQ ID NO 22
<211> LENGTH: 1967
<212> TYPE: DNA
<213> ORGANISM: Mouse

<400> SEQUENCE: 22

| | |
|---|---|
| gctgcgcgcc cccgcgctga tccctgtcga gcgtctacgc gcctcgcttc ctttgcctgg | 60 |
| agctcggcgc cgagggggc cggaccctgg ctctgcggcc gcgacctggg tcttgcgggc | 120 |
| ctgagccctg agtggcgtcc agtccagctc ccagtgaccg cgccctgct tcaggtccga | 180 |
| ccggcgagat gacgcggagc cccgcgctgc tgctgctgct attgggggcc ctcccgtcgg | 240 |
| ctgaggcggc gcgaggaccc ccaagaatgg cagacaaagt ggtcccacgg caggtggccc | 300 |
| gcctgggccg cactgtgcgg ctacagtgcc cagtggaggg ggacccacca ccgttgacca | 360 |
| tgtggaccaa agatggccgc acaatccaca gtggctggag ccgcttccgt gtgctgcccc | 420 |
| agggtctgaa ggtgaaggag gtggaggccg aggatgccgg tgtttatgtg tgcaaggcca | 480 |
| ccaatggctt tggcagcctc agcgtcaact acactctcat catcatggat gatattagtc | 540 |
| cagggaagga gagccctggg ccaggtggtt cttcgggggg ccaggaggac ccagccagcc | 600 |
| agcagtgggc acggcctcgc ttcacacagc cctccaagat gaggcgccga gtgattgcac | 660 |
| ggcctgtggg tagctctgtg cggctcaagt gtgtggccag tgggcaccca cggccagaca | 720 |
| tcatgtggat gaaggatgac cagaccttga cgcatctaga ggctagtgaa cacagaaaga | 780 |
| agaagtggac actgagcttg aagaacctga gcctgaaga cagtggcaag tacacgtgcc | 840 |
| gtgtatctaa caaggccggt gccatcaacg ccacctacaa agtggatgta atccagcgga | 900 |
| ctcgttccaa gcctgtgctc acagggacac accctgtgaa cacaacggtg gacttcggtg | 960 |
| ggacaacgtc cttccagtgc aaggtgcgca gtgacgtgaa gcctgtgatc cagtggctga | 1020 |
| agcgggtgga gtacggctcc gagggacgcc acaactccac cattgatgtg ggtggccaga | 1080 |
| agtttgtggt gttgccacg ggtgatgtgt ggtcacggcc tgatggctcc tacctcaaca | 1140 |
| agctgctcat ctctcgggcc cgccaggat atgctggcat gtacatctgc ctaggtgcaa | 1200 |
| ataccatggg ctacagtttc cgtagcgcct tcctcactgt attaccagac ccaaacctc | 1260 |
| cagggcctcc tatggcttct tcatcgtcat ccacaagcct gccatggcct gtggtgatcg | 1320 |
| gcatcccagc tggtgctgtc ttcatcctag cactgtgct gctctggctt tgccagacca | 1380 |
| agaagaagcc atgtgcccca gcatctacac ttcctgtgcc tgggcatcgt ccccaggga | 1440 |
| catcccgaga acgcagtggt gacaaggacc tgccctcatt ggctgtgggc atatgtgagg | 1500 |
| agcatggatc cgccatggcc ccccagcaca tcctggcctc tggctcaact gctggcccca | 1560 |
| agctgtaccc caagctatac acagatgtgc acacacacac acatacacac acctgcactc | 1620 |
| acacgctctc atgtggaggg caaggttcat caacaccagc atgtccacta tcagtgctaa | 1680 |
| atacagcgaa tctccaagca ctgtgtcctg aggtaggcat atgggggcca aggcaacagg | 1740 |
| ttgggagaat tgagaacaat ggaggaagag tatcttaggg tgccttatgg tggacactca | 1800 |

-continued

```
caaacttggc catatagatg tatgtactac cagatgaaca gccagccaga ttcacacacg      1860
cacatgttta aacgtgtaaa cgtgtgcaca actgcacaca caacctgaga aaccttcagg      1920
aggatttggg gtgtgacttt gcagtgacat gtagcgatgg ctagttg                    1967
```

<210> SEQ ID NO 23
<211> LENGTH: 1742
<212> TYPE: DNA
<213> ORGANISM: Mouse

<400> SEQUENCE: 23

```
gcgcggcgcc ccgggcccct cgcccgccg ccctcttcc ccgccctcgc caagcctcgc        60
cgtttatccg cgcggacagc gcgccccgcg ccccagcccg gccctagccg ccagcgccca      120
ggtagcgccg ccccgcccag gccgggcccg ggggcgcggg gggcgggatg cggcgcccgg      180
ggcagcgatg accgcgtcgc gctgctcagg ggcccggctc tgacccgtt gcctgctgcg       240 cgcccccgcg ctgatccctg tcgagcgtct acgcgcctcg cttcctttgc ctggagctcg      300
gcgccgaggg gggccggacc ctggctctgc ggccgcgacc tgggtcttgc gggcctgagc      360
cctgagtggc gtccagtcca gctcccagtg accgcgcccc tgcttcaggt ccgaccggcg      420
agatgacgcg gagccccgcg ctgctgctgc tgctattggg ggccctcccg tcggctgagg      480
cggcgcgaga tgatattagt ccagggaagg agagccctgg gccaggtggt tcttcggggg      540
gccaggagga cccagccagc cagcagtggg cacggcctcg cttcacacag ccctccaaga      600 tgaggcgcc agtgattgca cggcctgtgg gtagctctgt gcggctcaag tgtgtggcca      660
gtgggcaccc acggccagac atcatgtgga tgaaggatga ccagaccttg acgcatctag      720
aggctagtga acacagaaag aagaagtgga cactgagctt gaagaacctg aagcctgaag      780
acagtggcaa gtacacgtgc cgtgtatcta acaaggccgg tgccatcaac gccacctaca      840
aagtggatgt aatccagcgg actcgttcca agcctgtgct cacagggaca caccctgtga      900
acacaacggt ggacttcggt gggacaacgt ccttccagtg caaggtgcgc agtgacgtga      960
agcctgtgat ccagtggctg aagcgggtgg agtacggctc cgaggacgc cacaactcca      1020 ccattgatgt gggtggccag aagtttgtgg tgttgcccac gggtgatgtg tggtcacggc      1080
ctgatggctc ctacctcaac aagctgctca tctctcgggc ccgccaggat gatgctggca      1140
tgtacatctg cctaggtgca aataccatgg gctacagttt ccgtagcgcc ttcctcactg      1200
tattaccaga ccccaaacct cctccagggc tccctatgcc ttcttcatcg tcatccacaa      1260
gcctgccatg gcctgtggtg atcggcatcc agctggtgc tgtcttcatc ctaggcactg       1320
tgctgctctg gctttgccag accaagaaga agccatgtgc cccagcatct acacttcctg      1380
tgcctgggca tcgtccccca gggacatccc agaacgcag tggtgacaag gacctgccct       1440
cattggctgt gggcatatgt gaggagcatg atccgccat ggccccccag cacatcctgg       1500
cctctggctc aactgctggc cccaagctgt accccaagct atacacagat gtgcacacac      1560
acacacatac acacacctgc actcacacgc tctcatgtgg agggcaaggt tcatcaacac      1620
cagcatgtcc actatcagtg ctaaatacag cgaatctcca agcactgtgt cctgaggtag      1680
gcatatgggg gccaaggcaa caggttggga gaattgagaa caatggagga agagtatctt      1740
ag                                                                     1742
```

<210> SEQ ID NO 24
<211> LENGTH: 1004
<212> TYPE: DNA

<210> SEQ ID NO 24
<211> LENGTH: 1004
<212> TYPE: DNA
<213> ORGANISM: Human

<400> SEQUENCE: 24

```
gcggccgcga ccccaggtcc ggacaggccg agatgacgcc gagcccctg ttgctgctcc      60
tgctgccgcc gctgctgctg ggggccttcc caccggccgc cgccgccga ggccccccaa    120
agatggcgga caaggtggtc ccacggcagg tggccggctg ggccgcactg tgcggctgca    180
gtgccagtgg aggggaccc gccgccgctg accatgtgga ccaaggatgg ccgcaccatc     240
cacagcggct ggagccgctt ccgcgtgctg ccgcagggc tgaaggtgaa gcaggtggag     300
cgggaggatg ccggcgtgta cgtgtgcaag gccaccaacg gcttcggcag ccttagcgtc    360
aactacaccc tcgtcgtgct ggatgacatt agcccaggga aggagagcct ggggcccgac    420
agctcctctg ggggtcaaga ggaccccgcc agccagcagt gggcacgacc gcgcttcaca    480
cagccctcca agatgaggcg ccgggtgatc gcacggcccg tgggtagctc cgtgcggctc    540
aagtgcgtgg ccagcgggca ccctcggccc gacatcacgt ggatgaagga cgaccaggcc    600
ttgacgcgcc cagaggccgc tgagcccagg aagaagaagt ggacactgag cctgaagaac    660
ctgcggccgg aggacagcgg caaatacacc tgccgcgtgt cgaaccgcgc gggcgccatc    720
aacgccacct acaaggtgga tgtgatccag cggacccgtt ccaagcccgt gctcacaggc    780
acgcaccccg tgaacacgac ggtggacttc ggggggacca cgtccttcca gtgcaaggtg    840
cgcagcgacg tgaagccggt gatccagtgg ctgaagcgcg tggagtacgg cgccgagggc    900
cgccacaact ccaccatcga tgtgggcggc cagaagtttg tggtgctgcc cacgggtgac    960
gtgtggtcgc ggcccgacgg ctcctacctc aataagccgc tccc                   1004
```

<210> SEQ ID NO 25
<211> LENGTH: 478
<212> TYPE: DNA
<213> ORGANISM: Mouse

<400> SEQUENCE: 25

```
agaaaaaggc ctcgctaaag caacaaacct gatcattttc aagaaccata ggactgaggt      60
gaagccatga agttcttgct gatctcccta gccctatggc tgggcacagt gggcacacgt    120
gggacagagc ccgaactcag cgagacccag cgcaggagcc tacaggtggc tctggaggag    180
ttccacaaac acccacctgt gcagttggcc ttccaagaga tcggtgtgga cagagctgaa    240
gaagtgctct tctcagctgg caccttttgtg aggttggaat ttaagctcca gcagaccaac    300
tgccccaaga aggactggaa aaagccggag tgcacaatca aaccaaacgg ggcggaaatg    360
cctggcctgc attaaaatgg accccaaggg taaaattcta ggccggatag tccactgccc    420
aattctgaag caagggcctc aggatcctca ggagttgcaa tgcattaaga tagcacag     478
```

<210> SEQ ID NO 26
<211> LENGTH: 545
<212> TYPE: DNA
<213> ORGANISM: Mouse

<400> SEQUENCE: 26

```
agggaacaac tgccagggag ctgttccagg gaccacacag aaaaaggcct cgctaaagca      60
acaaacctga tcattttcaa gaaccatagg actgaggtga agccatgaag ttcttgctga    120
tctccctagc cctatggctg ggcacagtgg gcacacgtgg gacagagccc gaactcagcg    180
agacccagcg caggagccta caggtggctc tggaggagtt ccacaaacac ccacctgtgc    240
agttggcctt ccaagagatc ggtgtggaca gagctgaaga agtgctcttc tcagctggca    300
```

| | |
|---|---:|
| cctttgtgag gttggaattt aagctccagc agaccaactg ccccaagaag gactggaaaa | 360 |
| agccggagtg cacaatcaaa ccaaacggga gaaggcggaa atgcctggcc tgcattaaaa | 420 |
| tggaccccaa gggtaaaatt ctaggccgga tagtccactg cccaattctg aagcaagggc | 480 |
| ctcaggatcc tcaggagttg caatgcatta agatagcaca ggctggcgaa gacccccacg | 540 |
| gctac | 545 |

<210> SEQ ID NO 27
<211> LENGTH: 2213
<212> TYPE: DNA
<213> ORGANISM: Mouse

<400> SEQUENCE: 27

| | |
|---|---:|
| gttgcaggcg ctcggagtca gcatggaaag tctctgcggg gtcctgggat ttctgctgct | 60 |
| ggctgcagga ctgcctctcc aggctgccaa gcgatttcgt gatgtgctgg gccatgaaca | 120 |
| gtatcccaat cacatgagag agcacaacca attacgtggc tggtcttcgg atgaaaatga | 180 |
| atgggatgaa cacctgtatc cagtgtggag gaggggagac ggcaggtgga aggactcctg | 240 |
| ggaaggaggc cgtgtgcagg cagtcctgac cagtgactca ccggctctgg tgggttccaa | 300 |
| tatcaccttt gtggtgaacc tggtgttccc cagatgccag aaggaagatg ctaatggcaa | 360 |
| tatcgtctat gagaagaact gcaggaatga tttgggactg acctctgacc tgcatgtcta | 420 |
| caactggact gcaggggcag atgatggtga ctgggaagat ggcaccagcc gaagccagca | 480 |
| tctcaggttc ccggacagga ggcccttccc tcgcccccat ggatggaaga atggagcttt | 540 |
| tgtctacgtc tttcacacac ttggccagta tttccaaaaa ctgggtcggt gttcagcacg | 600 |
| ggtttctata aacacagtca acttgacagc tggccctcag gtcatggaag tgactgtctt | 660 |
| tcgaagatac ggccgggcat acattcccat ctcgaaggtg aaagatgtgt atgtgataac | 720 |
| agatcagatc cctgtattcg tgaccatgtc cagaagaat gacaggaact tgtctgatga | 780 |
| gatcttcctc agagacctcc ccatcgtctt cgatgtcctc attcatgatc ccagccactt | 840 |
| cctcaacgac tctgccattt cctacaagtg aactttggg acaacactg gcctgtttgt | 900 |
| ctccaacaat cacactttga atcacactta tgtgctcaat ggaaccttca accttaacct | 960 |
| caccgtgcaa actgcagtgc ccgggccatg ccctcccccct tcgccttcga ctccgcctcc | 1020 |
| accttcaact ccgccctcac ctccgccctc acctctgccc acattatcaa cacctagccc | 1080 |
| ctctttaatg cctactggtt acaaatccat ggagctgagt gacatttcca atgaaaactg | 1140 |
| ccgaataaac agatatggct acttcagagc caccatcaca attgtagagg ggatcctgga | 1200 |
| agtcagcatc atgcagatag cagatgtccc catgcccaca ccgcagcctg ccaactccct | 1260 |
| gatggacttc actgtgacct gcaaagggc cacccccatg aagcctgta cgatcatctc | 1320 |
| cgacccacc tgccagatcg cccagaaccg ggtctcagc cctgtggctg tggatgggct | 1380 |
| gtgcctgctg tctgtgagaa gagccttcaa tgggtctggc acctactgtg tgaatttcac | 1440 |
| tctgggagat gatgcaagcc tggccctcac cagcaccctg atctctatcc tggcaaaga | 1500 |
| cccagactcc cctctgagag cagtgaatgg tgtcctgatc tccattggct gcctggctgt | 1560 |
| gcttgtcacc atggttacca tcttgctgta caaaaacac aaggcgtaca agccaatagg | 1620 |
| aaactgcccc aggaacacgg tcaagggcaa aggcctgagt gttctcctca gccacgcgaa | 1680 |
| agccccgttc ttccgaggag accaggagaa ggatccattg ctccaggaca agccaaggac | 1740 |
| actctaagtc tttggccttc cctctgacca ggaacccact cttctgtgca tgtatgtgag | 1800 |

```
ctgtgcagaa gtatgtggct gggaactgtt gttctctaag gattattgta aatgtatat      1860 cgtggcttag ggagtgtggt taaatagcat tttagagaag acatgggaag acttagtgtt    1920
tcttcccatc tgtattgtgg tttttacact gttcgtgggg tggacacgct gtgtctgaag    1980
gggaggtggg gtcactgcta cttaaggtcc taggttaact gggggagata ccacagatgc    2040
ctcagctttc cacataacat ggcatgaacc ccagctaatc accacctgaa ggccatgctt    2100
catctgcctt ccaactcact gagcatgcct gagctcctga caaaattata atgggcccgg    2160
gctttgtgta tggtgcgtgt gtgtacatat tctactcatt aaaaaggtag tct           2213
```

<210> SEQ ID NO 28
<211> LENGTH: 412
<212> TYPE: DNA
<213> ORGANISM: Mouse

<400> SEQUENCE: 28

```
gcggagtccc gcctcgccgc ccctcgagcg cccccagctt ctctgctggc cggaacctgc      60
accccgaacc aggaagcacc tggcggcggg cgcgggatgg ctgggcccag ctggggtctc    120
cctcggctgg acggtttcat ccttaccgag cgcctgggca gtggcacgta cgccacggtg    180
tacaaggcct acgccaagaa ggatactcgg gaagtggtag ccataaaatg cgtggccaag    240
aagagtctca acaaggcgtc agtggaaaac ctcctgactg agattgagat cctcaagggc    300
attcggcacc cccatatcgt gcagctgaaa gacttccagt gggacaatga caatatctac    360
ctcatcatgg agttctgtgc aggggtgac  ctgtctcgct tcattcatac cc             412
```

<210> SEQ ID NO 29
<211> LENGTH: 437
<212> TYPE: DNA
<213> ORGANISM: Mouse

<400> SEQUENCE: 29

```
cacagtcttg tttctggtgg cttttgatcac tgtggggatg aacactacct atgtagtgtc      60
ttgccccaaa gaatttgaaa aacctggagc ttgtcccaag ccttcaccag aaagtgttgg    120
aatttgtgtt gatcaatgct caggagatgg atcctgccct ggcaacatga agtgctgtag    180
caatagctgt ggtcatgtct gcaaaactcc tgtcttttaa atggttgaca gccatgtgga    240
agatggattc aatcttcata acatgaatg atggccagcc ccagaagatt tcttctgaat     300
tcacagagcc tgtgcttggc tacttcctag ccctagaatt gcattcttgg acaaggaaga    360
tctatattgt ggtgacaatg ccctaatatg tctgtgtcca aaataaacta cccttagcat    420
tcaaaaaaaa aaaaaaa                                                    437
```

<210> SEQ ID NO 30
<211> LENGTH: 126
<212> TYPE: PRT
<213> ORGANISM: Mouse
<220> FEATURE:
<221> NAME/KEY: VARIANT
<222> LOCATION: (1)...(126)
<223> OTHER INFORMATION: Xaa = Any Amino Acid

<400> SEQUENCE: 30

Val Asp Phe Gly Gly Thr Thr Ser Phe Gln Cys Lys Val Arg Ser Asp
 1               5                  10                  15

Val Lys Pro Val Ile Gln Trp Leu Lys Arg Val Glu Tyr Gly Ser Glu
                20                  25                  30

Gly Arg His Asn Ser Thr Ile Asp Val Gly Gly Gln Lys Phe Val Val

```
                35                  40                  45
Leu Pro Thr Gly Asp Val Trp Ser Arg Pro Asp Gly Ser Tyr Leu Asn
 50                  55                  60

Lys Leu Leu Ile Ser Arg Ala Arg Gln Asp Asp Ala Gly Met Tyr Ile
 65                  70                  75                  80

Cys Leu Gly Ala Asn Thr Met Gly Tyr Ser Phe Arg Ser Ala Phe Leu
                 85                  90                  95

Thr Val Leu Pro Asp Pro Lys Pro Pro Gly Pro Met Ala Ser Ser
                100                 105                 110

Ser Ser Ser Thr Ser Leu Pro Trp Pro Val Xaa Gly Ile Pro
            115                 120                 125

<210> SEQ ID NO 31
<211> LENGTH: 529
<212> TYPE: PRT
<213> ORGANISM: Mouse

<400> SEQUENCE: 31

Met Thr Arg Ser Pro Ala Leu Leu Leu Leu Leu Gly Ala Leu Pro
  1               5                  10                  15

Ser Ala Glu Ala Ala Arg Gly Pro Pro Arg Met Ala Asp Lys Val Val
                 20                  25                  30

Pro Arg Gln Val Ala Arg Leu Gly Arg Thr Val Arg Leu Gln Cys Pro
                 35                  40                  45

Val Glu Gly Asp Pro Pro Pro Leu Thr Met Trp Thr Lys Asp Gly Arg
 50                  55                  60

Thr Ile His Ser Gly Trp Ser Arg Phe Arg Val Leu Pro Gln Gly Leu
 65                  70                  75                  80

Lys Val Lys Glu Val Glu Ala Glu Asp Ala Gly Val Tyr Val Cys Lys
                 85                  90                  95

Ala Thr Asn Gly Phe Gly Ser Leu Ser Val Asn Tyr Thr Leu Ile Ile
                100                 105                 110

Met Asp Asp Ile Ser Pro Gly Lys Glu Ser Pro Gly Pro Gly Gly Ser
            115                 120                 125

Ser Gly Gly Gln Glu Asp Pro Ala Ser Gln Trp Ala Arg Pro Arg
    130                 135                 140

Phe Thr Gln Pro Ser Lys Met Arg Arg Val Ile Ala Arg Pro Val
145                 150                 155                 160

Gly Ser Ser Val Arg Leu Lys Cys Val Ala Ser Gly His Pro Arg Pro
                165                 170                 175

Asp Ile Met Trp Met Lys Asp Asp Gln Thr Leu Thr His Leu Glu Ala
            180                 185                 190

Ser Glu His Arg Lys Lys Lys Trp Thr Leu Ser Leu Lys Asn Leu Lys
        195                 200                 205

Pro Glu Asp Ser Gly Lys Tyr Thr Cys Arg Val Ser Asn Lys Ala Gly
    210                 215                 220

Ala Ile Asn Ala Thr Tyr Lys Val Asp Val Ile Gln Arg Thr Arg Ser
225                 230                 235                 240

Lys Pro Val Leu Thr Gly Thr His Pro Val Asn Thr Thr Val Asp Phe
                245                 250                 255

Gly Gly Thr Thr Ser Phe Gln Cys Lys Val Arg Ser Asp Val Lys Pro
            260                 265                 270

Val Ile Gln Trp Leu Lys Arg Val Glu Tyr Gly Ser Glu Gly Arg His
        275                 280                 285
```

```
Asn Ser Thr Ile Asp Val Gly Gln Lys Phe Val Leu Pro Thr
    290                 295                 300

Gly Asp Val Trp Ser Arg Pro Asp Gly Ser Tyr Leu Asn Lys Leu Leu
305                 310                 315                 320

Ile Ser Arg Ala Arg Gln Asp Asp Ala Gly Met Tyr Ile Cys Leu Gly
                325                 330                 335

Ala Asn Thr Met Gly Tyr Ser Phe Arg Ser Ala Phe Leu Thr Val Leu
                340                 345                 350

Pro Asp Pro Lys Pro Gly Pro Pro Met Ala Ser Ser Ser Ser
                355                 360                 365

Thr Ser Leu Pro Trp Pro Val Val Ile Gly Ile Pro Ala Gly Ala Val
    370                 375                 380

Phe Ile Leu Gly Thr Val Leu Leu Trp Leu Cys Gln Thr Lys Lys Lys
385                 390                 395                 400

Pro Cys Ala Pro Ala Ser Thr Leu Pro Val Pro Gly His Arg Pro Pro
                405                 410                 415

Gly Thr Ser Arg Glu Arg Ser Gly Asp Lys Asp Leu Pro Ser Leu Ala
                420                 425                 430

Val Gly Ile Cys Glu Glu His Gly Ser Ala Met Ala Pro Gln His Ile
                435                 440                 445

Leu Ala Ser Gly Ser Thr Ala Gly Pro Lys Leu Tyr Pro Lys Leu Tyr
    450                 455                 460

Thr Asp Val His Thr His Thr His Thr His Thr Cys Thr His Thr Leu
465                 470                 475                 480

Ser Cys Gly Gly Gln Gly Ser Ser Thr Pro Ala Cys Pro Leu Ser Val
                485                 490                 495

Leu Asn Thr Ala Asn Leu Gln Ala Leu Cys Pro Glu Val Gly Ile Trp
                500                 505                 510

Gly Pro Arg Gln Gln Val Gly Arg Ile Glu Asn Asn Gly Gly Arg Val
                515                 520                 525

Ser
```

<210> SEQ ID NO 32
<211> LENGTH: 439
<212> TYPE: PRT
<213> ORGANISM: Mouse

<400> SEQUENCE: 32

```
Met Thr Arg Ser Pro Ala Leu Leu Leu Leu Leu Gly Ala Leu Pro
  1               5                  10                  15

Ser Ala Glu Ala Ala Arg Asp Asp Ile Ser Pro Gly Lys Glu Ser Pro
                20                  25                  30

Gly Pro Gly Gly Ser Gly Gly Gln Glu Asp Pro Ala Ser Gln Gln
                35                  40                  45

Trp Ala Arg Pro Arg Phe Thr Gln Pro Ser Lys Met Arg Arg Arg Val
    50                  55                  60

Ile Ala Arg Pro Val Gly Ser Ser Val Arg Leu Lys Cys Val Ala Ser
65                  70                  75                  80

Gly His Pro Arg Pro Asp Ile Met Trp Met Lys Asp Asp Gln Thr Leu
                85                  90                  95

Thr His Leu Glu Ala Ser Glu His Arg Lys Lys Lys Trp Thr Leu Ser
                100                 105                 110

Leu Lys Asn Leu Lys Pro Glu Asp Ser Gly Lys Tyr Thr Cys Arg Val
    115                 120                 125
```

```
Ser Asn Lys Ala Gly Ala Ile Asn Ala Thr Tyr Lys Val Asp Val Ile
    130                 135                 140

Gln Arg Thr Arg Ser Lys Pro Val Leu Thr Gly Thr His Pro Val Asn
145                 150                 155                 160

Thr Thr Val Asp Phe Gly Gly Thr Thr Ser Phe Gln Cys Lys Val Arg
            165                 170                 175

Ser Asp Val Lys Pro Val Ile Gln Trp Leu Lys Arg Val Glu Tyr Gly
            180                 185                 190

Ser Glu Gly Arg His Asn Ser Thr Ile Asp Val Gly Gly Gln Lys Phe
            195                 200                 205

Val Val Leu Pro Thr Gly Asp Val Trp Ser Arg Pro Asp Gly Ser Tyr
    210                 215                 220

Leu Asn Lys Leu Leu Ile Ser Arg Ala Arg Gln Asp Asp Ala Gly Met
225                 230                 235                 240

Tyr Ile Cys Leu Gly Ala Asn Thr Met Gly Tyr Ser Phe Arg Ser Ala
            245                 250                 255

Phe Leu Thr Val Leu Pro Asp Pro Lys Pro Pro Gly Pro Pro Met
            260                 265                 270

Ala Ser Ser Ser Ser Thr Ser Leu Pro Trp Pro Val Val Ile Gly
            275                 280                 285

Ile Pro Ala Gly Ala Val Phe Ile Leu Gly Thr Val Leu Leu Trp Leu
    290                 295                 300

Cys Gln Thr Lys Lys Lys Pro Cys Ala Pro Ala Ser Thr Leu Pro Val
305                 310                 315                 320

Pro Gly His Arg Pro Pro Gly Thr Ser Arg Glu Arg Ser Gly Asp Lys
            325                 330                 335

Asp Leu Pro Ser Leu Ala Val Gly Ile Cys Glu Glu His Gly Ser Ala
            340                 345                 350

Met Ala Pro Gln His Ile Leu Ala Ser Gly Ser Thr Ala Gly Pro Lys
            355                 360                 365

Leu Tyr Pro Lys Leu Tyr Thr Asp Val His Thr His Thr His Thr His
    370                 375                 380

Thr Cys Thr His Thr Leu Ser Cys Gly Gly Gln Gly Ser Ser Thr Pro
385                 390                 395                 400

Ala Cys Pro Leu Ser Val Leu Asn Thr Ala Asn Leu Gln Ala Leu Cys
            405                 410                 415

Pro Glu Val Gly Ile Trp Gly Pro Arg Gln Gln Val Gly Arg Ile Glu
            420                 425                 430

Asn Asn Gly Gly Arg Val Ser
            435

<210> SEQ ID NO 33
<211> LENGTH: 322
<212> TYPE: PRT
<213> ORGANISM: Human

<400> SEQUENCE: 33

Arg Arg Ala Pro Cys Cys Cys Ser Cys Cys Arg Arg Cys Cys Trp Gly
1               5                   10                  15

Pro Ser His Arg Pro Pro Pro Glu Ala Pro Gln Arg Trp Arg Thr
            20                  25                  30

Arg Trp Ser His Gly Arg Trp Pro Ala Gly Pro His Cys Ala Ala Ala
            35                  40                  45

Val Pro Val Glu Gly Asp Pro Pro Leu Thr Met Trp Thr Lys Asp
    50                  55                  60
```

```
Gly Arg Thr Ile His Ser Gly Trp Ser Arg Phe Arg Val Leu Pro Gln
 65                  70                  75                  80

Gly Leu Lys Val Lys Gln Val Glu Arg Glu Asp Ala Gly Val Tyr Val
                 85                  90                  95

Cys Lys Ala Thr Asn Gly Phe Gly Ser Leu Ser Val Asn Tyr Thr Leu
                100                 105                 110

Val Val Leu Asp Asp Ile Ser Pro Gly Lys Glu Ser Leu Gly Pro Asp
            115                 120                 125

Ser Ser Ser Gly Gly Gln Glu Asp Pro Ala Ser Gln Gln Trp Ala Arg
        130                 135                 140

Pro Arg Phe Thr Gln Pro Ser Lys Met Arg Arg Val Ile Ala Arg
145                 150                 155                 160

Pro Val Gly Ser Ser Val Arg Leu Lys Cys Val Ala Ser Gly His Pro
                165                 170                 175

Arg Pro Asp Ile Thr Trp Met Lys Asp Asp Gln Ala Leu Thr Arg Pro
            180                 185                 190

Glu Ala Ala Glu Pro Arg Lys Lys Lys Trp Thr Leu Ser Leu Lys Asn
        195                 200                 205

Leu Arg Pro Glu Asp Ser Gly Lys Tyr Thr Cys Arg Val Ser Asn Arg
    210                 215                 220

Ala Gly Ala Ile Asn Ala Thr Tyr Lys Val Asp Val Ile Gln Arg Thr
225                 230                 235                 240

Arg Ser Lys Pro Val Leu Thr Gly Thr His Pro Val Asn Thr Thr Val
                245                 250                 255

Asp Phe Gly Gly Thr Thr Ser Phe Gln Cys Lys Val Arg Ser Asp Val
            260                 265                 270

Lys Pro Val Ile Gln Trp Leu Lys Arg Val Glu Tyr Gly Ala Glu Gly
        275                 280                 285

Arg His Asn Ser Thr Ile Asp Val Gly Gly Gln Lys Phe Val Val Leu
    290                 295                 300

Pro Thr Gly Asp Val Trp Ser Arg Pro Asp Gly Ser Tyr Leu Asn Lys
305                 310                 315                 320

Pro Leu

<210> SEQ ID NO 34
<211> LENGTH: 102
<212> TYPE: PRT
<213> ORGANISM: Mouse

<400> SEQUENCE: 34

Met Lys Phe Leu Leu Ile Ser Leu Ala Leu Trp Leu Gly Thr Val Gly
  1               5                  10                  15

Thr Arg Gly Thr Glu Pro Glu Leu Ser Glu Thr Gln Arg Arg Ser Leu
                 20                  25                  30

Gln Val Ala Leu Glu Glu Phe His Lys His Pro Val Gln Leu Ala
             35                  40                  45

Phe Gln Glu Ile Gly Val Asp Arg Ala Glu Glu Val Leu Phe Ser Ala
         50                  55                  60

Gly Thr Phe Val Arg Leu Glu Phe Lys Leu Gln Gln Thr Asn Cys Pro
 65                  70                  75                  80

Lys Lys Asp Trp Lys Lys Pro Glu Cys Thr Ile Lys Pro Asn Gly Ala
                 85                  90                  95

Glu Met Pro Gly Leu His
                100
```

<210> SEQ ID NO 35
<211> LENGTH: 147
<212> TYPE: PRT
<213> ORGANISM: Mouse

<400> SEQUENCE: 35

```
Met Lys Phe Leu Leu Ile Ser Leu Ala Leu Trp Leu Gly Thr Val Gly
  1               5                  10                  15

Thr Arg Gly Thr Glu Pro Glu Leu Ser Glu Thr Gln Arg Arg Ser Leu
             20                  25                  30

Gln Val Ala Leu Glu Glu Phe His Lys His Pro Val Gln Leu Ala
         35                  40                  45

Phe Gln Glu Ile Gly Val Asp Arg Ala Glu Val Leu Phe Ser Ala
     50                  55                  60

Gly Thr Phe Val Arg Leu Glu Phe Lys Leu Gln Gln Thr Asn Cys Pro
 65                  70                  75                  80

Lys Lys Asp Trp Lys Lys Pro Glu Cys Thr Ile Lys Pro Asn Gly Arg
                 85                  90                  95

Arg Arg Lys Cys Leu Ala Cys Ile Lys Met Asp Pro Lys Gly Lys Ile
                100                 105                 110

Leu Gly Arg Ile Val His Cys Pro Ile Leu Lys Gln Gly Pro Gln Asp
            115                 120                 125

Pro Gln Glu Leu Gln Cys Ile Lys Ile Ala Gln Ala Gly Glu Asp Pro
        130                 135                 140

His Gly Tyr
145
```

<210> SEQ ID NO 36
<211> LENGTH: 574
<212> TYPE: PRT
<213> ORGANISM: Mouse

<400> SEQUENCE: 36

```
Met Glu Ser Leu Cys Gly Val Leu Gly Phe Leu Leu Ala Ala Gly
  1               5                  10                  15

Leu Pro Leu Gln Ala Ala Lys Arg Phe Arg Asp Val Leu Gly His Glu
             20                  25                  30

Gln Tyr Pro Asn His Met Arg Glu His Asn Gln Leu Arg Gly Trp Ser
         35                  40                  45

Ser Asp Glu Asn Glu Trp Asp Glu His Leu Tyr Pro Val Trp Arg Arg
     50                  55                  60

Gly Asp Gly Arg Trp Lys Asp Ser Trp Glu Gly Gly Arg Val Gln Ala
 65                  70                  75                  80

Val Leu Thr Ser Asp Ser Pro Ala Leu Val Gly Ser Asn Ile Thr Phe
                 85                  90                  95

Val Val Asn Leu Val Phe Pro Arg Cys Gln Lys Glu Asp Ala Asn Gly
                100                 105                 110

Asn Ile Val Tyr Glu Lys Asn Cys Arg Asn Asp Leu Gly Leu Thr Ser
            115                 120                 125

Asp Leu His Val Tyr Asn Trp Thr Ala Gly Ala Asp Asp Gly Asp Trp
        130                 135                 140

Glu Asp Gly Thr Ser Arg Ser Gln His Leu Arg Phe Pro Asp Arg Arg
145                 150                 155                 160

Pro Phe Pro Arg Pro His Gly Trp Lys Lys Trp Ser Phe Val Tyr Val
                165                 170                 175
```

```
Phe His Thr Leu Gly Gln Tyr Phe Gln Lys Leu Gly Arg Cys Ser Ala
            180                 185                 190

Arg Val Ser Ile Asn Thr Val Asn Leu Thr Ala Gly Pro Gln Val Met
        195                 200                 205

Glu Val Thr Val Phe Arg Arg Tyr Gly Arg Ala Tyr Ile Pro Ile Ser
        210                 215                 220

Lys Val Lys Asp Val Tyr Val Ile Thr Asp Gln Ile Pro Val Phe Val
225                 230                 235                 240

Thr Met Ser Gln Lys Asn Asp Arg Asn Leu Ser Asp Glu Ile Phe Leu
                245                 250                 255

Arg Asp Leu Pro Ile Val Phe Asp Val Leu Ile His Asp Pro Ser His
            260                 265                 270

Phe Leu Asn Asp Ser Ala Ile Ser Tyr Lys Trp Asn Phe Gly Asp Asn
            275                 280                 285

Thr Gly Leu Phe Val Ser Asn Asn His Thr Leu Asn His Thr Tyr Val
        290                 295                 300

Leu Asn Gly Thr Phe Asn Leu Asn Leu Thr Val Gln Thr Ala Val Pro
305                 310                 315                 320

Gly Pro Cys Pro Pro Pro Ser Pro Ser Thr Pro Pro Pro Ser Thr
                325                 330                 335

Pro Pro Ser Pro Pro Ser Pro Leu Pro Thr Leu Ser Thr Pro Ser
            340                 345                 350

Pro Ser Leu Met Pro Thr Gly Tyr Lys Ser Met Glu Leu Ser Asp Ile
            355                 360                 365

Ser Asn Glu Asn Cys Arg Ile Asn Arg Tyr Gly Tyr Phe Arg Ala Thr
        370                 375                 380

Ile Thr Ile Val Glu Gly Ile Leu Glu Val Ser Ile Met Gln Ile Ala
385                 390                 395                 400

Asp Val Pro Met Pro Thr Pro Gln Pro Ala Asn Ser Leu Met Asp Phe
                405                 410                 415

Thr Val Thr Cys Lys Gly Ala Thr Pro Met Glu Ala Cys Thr Ile Ile
                420                 425                 430

Ser Asp Pro Thr Cys Gln Ile Ala Gln Asn Arg Val Cys Ser Pro Val
            435                 440                 445

Ala Val Asp Gly Leu Cys Leu Leu Ser Val Arg Arg Ala Phe Asn Gly
            450                 455                 460

Ser Gly Thr Tyr Cys Val Asn Phe Thr Leu Gly Asp Ala Ser Leu
465                 470                 475                 480

Ala Leu Thr Ser Thr Leu Ile Ser Ile Pro Gly Lys Asp Pro Asp Ser
                485                 490                 495

Pro Leu Arg Ala Val Asn Gly Val Leu Ile Ser Ile Gly Cys Leu Ala
            500                 505                 510

Val Leu Val Thr Met Val Thr Ile Leu Leu Tyr Lys Lys His Lys Ala
            515                 520                 525

Tyr Lys Pro Ile Gly Asn Cys Pro Arg Asn Thr Val Lys Gly Lys Gly
        530                 535                 540

Leu Ser Val Leu Leu Ser His Ala Lys Ala Pro Phe Phe Arg Gly Asp
545                 550                 555                 560

Gln Glu Lys Asp Pro Leu Leu Gln Asp Lys Pro Arg Thr Leu
                565                 570

<210> SEQ ID NO 37
<211> LENGTH: 137
```

```
<212> TYPE: PRT
<213> ORGANISM: Mouse

<400> SEQUENCE: 37

Ala Glu Ser Arg Leu Ala Ala Pro Arg Ala Pro Ala Ser Leu Leu
 1               5                  10                  15

Ala Gly Thr Cys Thr Pro Asn Gln Glu Ala Pro Gly Gly Arg Gly
                20                  25                  30

Met Ala Gly Pro Ser Trp Gly Leu Pro Arg Leu Asp Gly Phe Ile Leu
         35                  40                  45

Thr Glu Arg Leu Gly Ser Gly Thr Tyr Ala Thr Val Tyr Lys Ala Tyr
     50                  55                  60

Ala Lys Lys Asp Thr Arg Glu Val Val Ala Ile Lys Cys Val Ala Lys
65                  70                  75                  80

Lys Ser Leu Asn Lys Ala Ser Val Glu Asn Leu Leu Thr Glu Ile Glu
                85                  90                  95

Ile Leu Lys Gly Ile Arg His Pro His Ile Val Gln Leu Lys Asp Phe
            100                 105                 110

Gln Trp Asp Asn Asp Asn Ile Tyr Leu Ile Met Glu Phe Cys Ala Gly
            115                 120                 125

Gly Asp Leu Ser Arg Phe Ile His Thr
        130                 135

<210> SEQ ID NO 38
<211> LENGTH: 72
<212> TYPE: PRT
<213> ORGANISM: Mouse

<400> SEQUENCE: 38

Thr Val Leu Phe Leu Val Ala Leu Ile Thr Val Gly Met Asn Thr Thr
 1               5                  10                  15

Tyr Val Ser Cys Pro Lys Glu Phe Glu Lys Pro Gly Ala Cys Pro
                20                  25                  30

Lys Pro Ser Pro Glu Ser Val Gly Ile Cys Val Asp Gln Cys Ser Gly
            35                  40                  45

Asp Gly Ser Cys Pro Gly Asn Met Lys Cys Cys Ser Asn Ser Cys Gly
    50                  55                  60

His Val Cys Lys Thr Pro Val Phe
65                  70

<210> SEQ ID NO 39
<211> LENGTH: 1587
<212> TYPE: DNA
<213> ORGANISM: Mouse

<400> SEQUENCE: 39
gcggcgcggg tagagggcgg tgggcggcga gcggcgatgg gccgcgcctg gggcttgctc      60
gttggactcc tgggcgtcgt gtggctgctg cgcttgggcc acggcgagga gcggcggccg     120
gagacagcgg cacagcgctg cttctgccag gttagtggtt acctggacga ctgtacctgt     180
gatgtcgaga ccatcgataa gtttaataac tacagacttt tcccaagact acaaaagctt     240
cttgaaagtg actactttag atattacaag gtgaacttga agaagccttg tcctttctgg     300
aatgacatca accagtgtgg aagaagagac tgtgccgtca aaccctgcca ttctgatgaa     360
gttcctgatg gaattaagtc tgcgagctac aagtattctg aggaagccaa ccgcattgaa     420
gaatgtgagc aagctgagcg acttggagcc gtggatgagt ctctgagtga ggagacccag     480
```

-continued

```
aaagctgtac ttcagtggac caagcatgat gattcgtcag acagcttctg cgaaattgac      540
gatatacagt cccccgatgc tgagtatgtg gacttactcc ttaaccctga gcgctacaca      600
ggctacaagg ggccagacgc ttggaggata tggagtgtca tctatgaaga aaactgtttt      660
aagccacaga caattcaaag gcctttggct tctgggcgag aaaaagtaa agagaacaca      720 ttttacaact ggctagaagg cctctgtgta gaaagagag cattctacag acttatatct      780
ggcctgcacg caagcattaa tgtgcatttg agtgcaaggt atcttttaca agatacttgg      840
ctggaaaaga atggggtca caatgtcaca gagttccagc agcgctttga tgggattctg      900
actgaaggag aaggcccacg aaggctgagg aacttgtact tcctgtacct gatagagtta      960
agggctctct ccaaagtgct tccatttttt gagcgtccag attttcagct cttcactggg     1020
aataaagttc aggatgcaga aaacaaagcg ttacttctgg agatacttca tgaaatcaag     1080
tcatttcctt tgcacttcga tgagaattct ttttttgctg gggataaaaa cgaagcacat     1140
aaactaaagg aggacttccg gctacacttt aggaacattt caagaatcat ggactgtgtt     1200
ggctgcttca agtgccgcct gtggggcaag cttcagacgc aggggctggg cactgctctg     1260
aagatcttgt ttttccgaaaa actgatcgca aatatgccgg aaagcggacc aagttatgag     1320
ttccagctaa ccagacaaga aatagtatca ctgtttaatg catttggaag gatttccaca     1380
agtgtgagag aactagagaa cttcaggcac ttgttacaga atgttcactg aggaggacgg     1440
ttggaatgtg cctgtttctg cacaggggaa tttgaagggc aaaatctctt ttagccccat     1500
ggttgcaatg tactgtccta agcccaacgt ttatataaac ctgcttttgt taaagaaaaa     1560
aaaaaaaaaa aaaaaaaaa aaaaaaa                                          1587
```

<210> SEQ ID NO 40
<211> LENGTH: 2435
<212> TYPE: DNA
<213> ORGANISM: Mouse

<400> SEQUENCE: 40

```
ggaggaggct cggcgccccc ctcctggccc cctcccccc ggtgctggct ccatgtctgt       60
gtgaccggcc gcagggtag gattcaggcc cgacgcgggg cggcgggcg acggcggctg      120 aggtgagagg cggcggcggc ggcgcggctc gggcaccggc cccccagcgg gaggatgaag      180
cggcggaacg ccgactgcag taagctccgc cgccccctga agcggaaccg gatcaccgag      240
ggtatctacg gcagtacatt tttatacctg aaattcctgg tagtgtgggc acttgtcctc      300
cttgccgact ttgtcctgga gttccgattt gaatacctgt ggccgttctg gcttttcatc      360
agaagcgtct atgattcctt cagataccaa ggactggcct tctcagtatt ttttgtttgt      420
gtagcattca cttcaaatat catatgtctc ctcttcattc ccatacaatg gctttttttc      480
gctgctagca catatgtatg ggtccagtac gtatggcaca cagaaagggg agtgtgtttg      540
cctacagtgt cactctggat cctctttgtt tatattgaag cagcaattag atttaaagat      600
ctgaaaaact ttcatgtaga cctttgtcga ccgtttgctg ctcactgcat tggatacccct      660 gtggtgactt tgggctttgg cttcaaaagt tatgtgagct acaaaatgcg gttaaggaag      720
cagaaggaag ttcagaagga gaacgagttt tacatgcagc ttcttcagca ggccctccct      780
ccagagcagc aaatgttgca gaagcaggag aaggaggctg aggaagcagc caagggattg      840
ccggacatgg attcctcgat ccttatacac acaacggag gcatcccagc caacaaaaaa      900
ctgtccacaa cgttgccaga gatagaatat cgagaaaaag ggaaagagaa ggacaaggat      960
gccaagaaac acaaccttgg aataaataac aacaacattc tacaacctgt agactctaag     1020
```

```
atacaagaga ttgagtatat ggaaaaccat atcaatagta aaagattaaa caatgatctt   1080
gtgggaagta cagaaaatct cttaaaagag gactcatgca ctgcttcctc aaaaaattac   1140
aaaaatgcca gtggagttgt gaactcctcg cctcgaagtc acagcgctac aaatggaagc   1200
attccttcct cgtctagtaa aaacgagaag aagcagaagt gcaccagcaa gggcccgagt   1260
gcacacaagg acttaatgga gaactgtatt cctaacaacc agctgagcaa accagacgcg   1320
ctggtaaggc tggaacaaga cattaaaaag ctaaaggctg acctgcaagc cagccggcaa   1380
gtggagcaag agctgcgcag tcagatcagc gccctctcaa gcacagagcg aggcatccgc   1440
tcagaaatgg gccagctccg gcaggagaac gagctgctgc agaacaagtt acacaatgcc   1500
gtgcaaatga agcaaaaaga caagcagaat atcagccagc tagagaagaa gctaaaggct   1560
gagcaggaag cccgaagctt tgtagaaaag cagctaatgg aggagaaaaa aaggaagaag   1620
ttagaagaag ccacagctgc acgggctgtt gcctttgctg ctgcatctag gggagagtgc   1680
acggaaacct acggagtcg gatcagagag ctagaagctg agggcaagaa gctcacaatg   1740
gacatgaaag tgaaggagga gcagatcagg gaactggaac tgaaggttca ggagcttcgg   1800
aagtacaaag aaaacgagaa ggacaccgag gtattgatgt cagccctctc cgccatgcaa   1860
gacaaaacgc aacacctaga gaacagtctc agcgcagaga cgaggatcaa gctggacctc   1920
ttctctgcac ttggtgatgc aaagcggcag ctggagattg cccaggggca aattcttcag   1980
aaagaccagg aaatcaagga cctaaaacag aaaatagctg aagtcatggc tgtcatgccc   2040
agcataacat acagtgctgc caccagtccc ctgagcccccg tgtcccccca ctactcttcc   2100
aagtttgtgg agaccagccc ctctggactt gaccctaatg cctctgtcta ccagcccttg   2160
aagaagtgaa ggccaactgt gtgctcgccc aacatttgca accaggaggc ttcgaaaagc   2220
agcgtctctg gcagtcaaga taaaaaagtt gatattgtgt tttgtgggac tgtatatgtt   2280
gtcattttta aagggggaa ataacatcca agtctgatta gaaccgccca tcagttgttc   2340
ttggaagttt ttagaagacc tcacggactt tgcagtttat ttttgttggc aacacatta   2400 aacccattct tggatttcaa gtaaaaaaaa aaaaa                              2435

<210> SEQ ID NO 41
<211> LENGTH: 1720
<212> TYPE: DNA
<213> ORGANISM: Mouse

<400> SEQUENCE: 41
gtgacgcgca ggcccaggcg gaagtgcggg cggaggatcc cgagccggat cccgagccgg    60
gcgcggggct cggggctcgc aggagcggct ggctcccgcg atggcgagcc tatggtgcgg   120
aaacctgctg cggctgggct cggggctcaa catgtcctgc ctggcgctgt cggtgctgct   180
gctcgcgcag ctgacaggcg ccgccaagaa ttttgaagat gtgagatgta aatgcatctg   240
ccctccctat aaagagaatc ctgggcacat ttataataag aatatatctc agaaagattg   300
tgattgcctt catgtcgtgg agcccatgcc tgtacgggga cctgatgtag aagcatactg   360
tctacgctgt gaatgcaaat acgaagagag aagctctgtc acaatcaagg ttaccattat   420
aatttatctc tctattttgg gccttctgct tctgtacatg gtatatctta ccttagttga   480
gcccatcctg aagaggcgcc tctttggaca ctcccagctg ttgcagagcg atgatgacgt   540 tgggggatcac cagcctttg caaatgccca tgatgtgctg gcccgctctc gcagccgagc   600
caatgttcta aacaaggtgg agtacgctca gcagcgctgg aagctccagg tccaggagca   660
```

```
gcgaaagtct gtcttcgacc gacacgttgt cctcagctaa ctgggaactg gaatcaggtg      720
actaggaaga acacgcagac aactgggaag aattgtctgg gtgtccgtgc gttttaatgc      780
catgtttgtt tttacaaatc cttgctggat ggaggaagac tccaaactgg aagcaaaccc      840
catgcttggt attttcctgt taatatatta atagagacat ttttacagca cacagttcca      900
agtcaaccag taagtctttt cctacttgtg acttttacta ataaaattaa gctgcctgtg      960
agttatcttg aagcccgtgt cctggaacaa gctctctctt tcttgccaca cagttctaac     1020
ttggtgttca agataacttc caggtgtgtt tttgcttctc tttcttgtgg tgggagagag     1080
agggaaggat gccttgggag tgcttgagta gcttctcaag tgtctttttcc agacagactt    1140 atgaatactt cagaccctct acttcacact tgttaatgtc ccagtgtagc tggcttgtca     1200
gcgtgctggc ctccccactt gacttttgca ctgactacat tacctaagat tctggttagc     1260
ctgtggctgc atttcatgac cagttggatc tgaaatgcct gggggctcct cacaaaatga     1320
agatttgttt catgcactgt gatgtctgac gcaacatgtt ctagaacaga ctggccatct     1380
gctagtttac actgatacct aaacacagtc tcagtgtgtg tggtcttcct catcttcttc     1440
tagtagctct aaggacttga acatttagaa taaagacatt ttctcttaag cccaagcctc     1500
cctggatgat tgacgtacaa atactgatca gccttttctg tcttgctgag aggcagttct     1560
ttgaactgat gtgggcagct ttgaacaagg actagagttc agattgcctc tctctgagaa     1620
gtctaacagt tattggataa ctggctttttt tcttcctaca tcctctttgg aatgtaacaa     1680
taaaataatt tacaaaaccc aaaaaaaaaa aaaaaaaaa                             1720

<210> SEQ ID NO 42
<211> LENGTH: 1008
<212> TYPE: DNA
<213> ORGANISM: Mouse

<400> SEQUENCE: 42
gggaaaagca agatcttgca caaggtcccc tccggctggc tgctggcaaa ggaaaggtgc       60
catgggacct ctccaccagt ttctcctgct gctgatcaca gccctgtccc aagccctcaa      120
caccacggtg ctgcagggca tggccggcca gtccttgagg gtgtcatgta cttatgacgc      180
cttgaagcac tggggagac gcaaggcctg tgtcggcag ctgggtgagg agggcccatg       240
ccagcgtgtg gtgagcacac acggtgtgtg gctgctggcc ttcctgaaga agcggaatgg      300
gagcacagtc atcgcagatg acacccttgc tggaaccgtc accatcactc tgaagaacct      360
ccaagccggt gacgcgggcc tctaccagtg tcagagtctc cgaggccgag aggctgaggt      420
cctgcagaaa gtactggtgg aggtgctgga ggaccctcta gatgaccaag atgctggaga      480
tctctgggtc cccgaggagt catcgagttt cgagggtgcc caagtggaac acagcacctc      540
caggaatcaa gagacctcct tcccacccac ctccattctt ctcctcctgg cctgcgttct      600
cctgagcaag tttcttgcag ccagcatcct ctgggctgtg ccaggggca ggcagaagcc       660 gggaacacct gtggtcagag ggctggactg tggccaagat gctgggcacc aacttcagat      720
cctcactgga cccggaggta cgtgagagaa ttctgagtgg gaggagaact acagcttaag      780
tccagccagg agtcaatcca gcctgcatgc tctcccctcc tccaccaaga cttctgtttc      840
tgctactttt gcttcagagg ccgcctctgc ctcaagccca cctatcctgg gagcaggaat      900
actggtgtgt acatctgtgt tgagtgggga agacagctgg atggttgtct gtcaagttct      960
gcactttgga cattaaacat tctccacaca ccaaaaaaaa aaaaaaaa                  1008
```

<210> SEQ ID NO 43
<211> LENGTH: 1871
<212> TYPE: DNA
<213> ORGANISM: Mouse

<400> SEQUENCE: 43

| | | | | | | |
|---|---|---|---|---|---|---|
| ggcagcggca | gtgtagagcc | gggccgggag | gccgatcctg | cgggtctgga | gtccggcggg | 60 |
| accatgggga | ccgggctgg | tgggccgagt | gtcctggcgc | tgctgttcgc | cgtgtgtgct | 120 |
| ccgctccggt | tgcaggcgga | ggagctgggt | gatggctgtg | ggcacatagt | gacctctcag | 180 |
| gacagtggca | caatgacatc | taagaattat | ccagggactt | accccaatta | cactgtgtgt | 240 |
| gaaaagatca | tcacagtccc | aaaggggaag | agacttattc | tgaggttggg | agatttgaac | 300 |
| attgagtcca | agacctgcgc | ttctgactat | ctcctcttca | gcagtgcaac | agatcagtat | 360 |
| ggtccatatt | gtgggagttg | ggctgttccc | aaagaactcc | ggctgaactc | aaacgaagtg | 420 |
| actgtcctct | tcaagagtgg | atctcacatt | tctggccggg | gctttctgct | gacctacgcc | 480 |
| agcagtgacc | atccagattt | aataacctgt | ttggaacgag | gcagccatta | tttcgaggaa | 540 |
| aaatacagca | aattctgccc | agctggctgt | agagacatag | cacgagatat | ttctgggaat | 600 |
| acaaaagatg | gttacagaga | tacctcttta | ttgtgcaaag | ctgccatcca | cgcagggatc | 660 |
| atcacagatg | aactaggtgg | ccacatcaac | ttgcttcaga | gcaaagggat | aagtcactat | 720 |
| gaaggactcc | tggccaatgg | cgtgctctcc | cggcatggtt | ctttgtcgga | aaagcgattt | 780 |
| cttttttacaa | ccccaggaat | gaatattaca | actgtggcga | ttccatcagt | gatcttcatc | 840 |
| gccctccttc | tgactggaat | ggggatcttt | gcaatctgta | gaaagaggaa | aaagaaagga | 900 |
| aatccatatg | tgtcagctga | cgctcagaaa | acaggctgtt | ggaagcagat | taaatatccc | 960 |
| tttgccaggc | atcagtcgac | ggaatttacc | atcagctatg | acaatgaaaa | agagatgaca | 1020 |
| caaaagttgg | atctcatcac | tagtgatatg | gcagattatc | agcagcctct | catgattggc | 1080 |
| acaggcacag | tcgcgagaaa | gggctctacc | ttccgaccca | tggacacaga | cactgaggag | 1140 |
| gtcagagtga | acactgaggc | cagcggccac | tatgactgtc | ctcaccgccc | gggccgccat | 1200 |
| gagtacgcac | tgcctttgac | gcactcagaa | cctgagtatg | ccacacctat | cgtggagcgg | 1260 |
| cacctgctgc | gagctcacac | cttctccaca | cagagcggct | accgagtccc | tgggcccagg | 1320 |
| cccactcacg | aacactccca | ttcctctgga | ggctttcctc | ctgctacagg | agccacccag | 1380 |
| gttgaaagct | atcagaggcc | agcaagcccc | aagcctgtgg | gtggtggcta | tgacaagcct | 1440 |
| gctgctagca | gcttcttgga | cagcagagac | ccagcctctc | agtcacagat | gacttccggg | 1500 |
| ggagatgatg | gttattcggc | acccagaaac | ggtcttgcgc | ccctcaacca | gacggccatg | 1560 |
| actgctcttt | tgtgaaccca | atgtgaaaga | aacctgctgt | ggtactgagc | gcgcaccgct | 1620 |
| gcgagtcact | ggaagaaatg | tgcaagcgtg | catgtgtgac | tcttcaggat | cctagagacg | 1680 |
| acctcactta | ctgtttacag | aactgtgcag | ctggtttagt | tccaacccct | cctgcagagc | 1740 |
| cagttggttt | ctgttgtgct | agaacaaggg | gacttttctc | atttgtctta | actgtgatgc | 1800 |
| tgtgctgtaa | aatgtgcaat | ttgtacagtt | atatttaaca | cgaattaaca | ttaaaaaaaa | 1860 |
| aaaaaaaaaa | a | | | | | 1871 |

<210> SEQ ID NO 44
<211> LENGTH: 3767
<212> TYPE: DNA
<213> ORGANISM: Mouse

<400> SEQUENCE: 44

-continued

```
cggacttggg gcgggaggct ggcggataaa aagcccccag ggcgcccgg gaggcccgtt      60 agcgctgctc tgccgcggcg cccggcccag ccccgacctc cacatcctgc cggcgctctg    120
aaatcaccat gatgtggccc caaccaccca ccttctccct gttcctgcta ctgctgctaa    180
gccaagcccc ttccagtagg ccacagtcat caggcaccaa gaagctcagg cttgtggggc    240
cagcggacag accaaaggag ggccgcttgg aggtgctgca ccagggccag tggggcacgg    300
tgtgtgatga tgatttcgct ctccaggagg ctactgtggc ctgccgacag ctgggctttg    360
agtcagcctt gacctgggca cacagtgcca agtatggtca aggagagggt cccatctggc    420
tggacaatgt tcgttgtttg ggcaccgaga agaccctaga tcagtgtggc tctaacggct    480
ggggtatcag tgactgcaga cactcagaag atgttggggt ggtatgtcac ccacggcgcc    540
agcacggata tcactctgag aaggtctcca atgccctcgg gcctcagggc cggcggctag    600
aagaggtacg gctgaaaccc atcctcgcca gtgccaaaag gcacagccca gtgactgaag    660
gggctgtgga agtacggtac gacgccact  ggaggcaggt gtgtgaccag ggctggacca    720
tgaacaacag cagggttgta tgcgggatgc tgggctttcc cagtcagaca tctgtcaaca    780
gccactacta cagaaaagtc tggaatctga agatgaagga tcccaagtct aggctcaaca    840
gcctgacaaa aagaattcc ttctggattc accgggttga ctgtttcggg acagagcccc     900
acttggccaa gtgccaggta caggtggctc caggaagggg caagcttcgg gcagcctgtc    960
caggcggcat gcacgctgtg gtcagctgtg tggcagggcc ccacttccgc cgacagaagc   1020
caaagcccac gcgcaaggag tcccatgcag aggagctgaa agtgcgcctg cgctctgggg   1080
ctcaggtggg tgagggccgt gtggaagtgc tcatgaaccg ccagtggggc acagtctgtg   1140
accacaggtg gaacctcatc tcagccagcg tcgtgtgtcg ccagcttggc tttggctctg   1200
cccgggaggc cctttttggg gcccagttgg gtcaagggct aggacccatc cacctgagtg   1260
aggtgcgctg ccggggggtat gagcggaccc tgggtgactg ccttgccctg gaagggtccc   1320
agaatggttg tcaacatgca aacgacgctg ctgtcaggtg caacatccca gacatgggct   1380
tccagaacaa ggtgcgcttg gctggtgggc gcaactccga gagggagtg gtggaggtgc    1440 aggtggaggt gaatgggggtc ccacgatggg ggactgtatg cagtgaccac tggggggctca   1500 ccgaagccat ggtgacctgt cggcaacttg gtctgggatt tgccaacttt gctctcaagg   1560
acacctggta ctggcagggg acaccagagg ccaaagaagt ggtgatgagt ggagttcgct   1620
gctccggcac agaaatggcc ctgcagcagt gtcagaggca tgggccggtg cactgttccc   1680
acggcccagg gcgcttctcg gctggcgttg cttgtatgaa cagtgctcca gacctcgtga   1740
tgaacgccca gctggtacaa gagacggcgt acttggagga tcgtccactc agcatgctgt   1800
actgtgctca cgaggaaaac tgcctctcca agtccgctga tcacatggac tggccctacg   1860
ggtaccggcg cttgctgcgc ttctcctcac agatctacaa ccttggccgg ccgacttcc    1920 gtcccaaggc tggacgccac agctggattt ggcaccagtg ccacaggcac taccacagca   1980
tcgaagtctt cactcattat gacctgctca cgctcaatgg ctccaaggtg gccgagggac   2040
acaaggccag cttctgtcta aagatacaa actgccctc aggagtgcag cggcgctatg    2100
catgtgccaa cttttgggaa cagggagtgg ctgtaggctg ctgggacacc taccggcatg   2160
acatcgattg ccagtgggtg gatatcacag atgtgggtcc aggggactat atcttccagg   2220
tggttgtgaa ccccacaaac gatgttgcag agtccgattt ctccaataac atgatacggt   2280
gccgctgcaa gtatgatgga cagcgagtct ggttgcacaa ctgccacaca ggagattcct   2340
accgagccaa tgcagagctc tccctggagc aggaacagcg actcaggaac aacttgatct   2400
```

```
gaagccatta ctgcactccc agctctgctc acacaccaga tacctcagct gactggagcc    2460
atgcccttca caaagccctg actcacagga caaggggcta gtgacaagga gcaccaagaa    2520
gctgctcagg aggcctttca gtggccagat catcacccgg gatggcagtt ctctcaggat    2580
ggctctgggc cagctcaacc ttctcttcct tcaggagact cgatcttctt tacaacttga    2640
tgcacagttc ccagtttcag gagctctaag ttcctcaggg atgaactgtg accaaggccc    2700
cctctaagtg gtgctttgca aatgtcttgg aggaccaaag gacagacgac ccgagaacac    2760
aagctgtgga tggagtcgtt ttctctgcta tacgctccac gcaaaaggac catgtcaaag    2820
tcacacctgg cagagacgct ggtgaacaca gtccctcagc ttaccctcac ttagaactcg    2880
catctcaggc tctgaagcct ctccttgcat ctttaccttc attcggtcac acatggtgtt    2940
tccaatatcc ctgaaccctc aggcctcctc catttcctga tgggtcaaca cctcgattat    3000
tggggctggg gagcaagttt cacagaatga cgagacaggg cctttcctgc agagtagtca    3060
gaaagcaaga cgaaggctga ggtcacatga attcagcctc ggaggacctc tgcccaggga    3120
ggtgccatat ctggcaggca ggccagtctc ttagaatcac ccacattgta gggttagcct    3180
aaatttcaga tttaaccaaa gccacttcac cttaaacttt tgcaattgag aagaaattgg    3240
tcagccaagc ccctctgcag gaacaccaag acaggtccag tagagttagg aacagaagac    3300
ggagttaaca agaagtgaga aggaaacctg ggagaggcca ccatccagtg aggcggctgt    3360
gctctgttct tgctcaggtg gtataagacc tggagtcttc cagggcatgc ctggaccttt    3420
tctccactga catacacaca gatgatcctt ctaggtctta taatgccaac aaaggttgct    3480
cactatgggc tgccacaaag gccagaccag ctgagcttct gcagcttcca ctgcactaca    3540
ctctgccctc ttccctccag agctggatga cgctcggaac acaatccttg gcacagccca    3600
ccctagtaca tttcttgggt ctcacactaa cctgcttcac cgttacgctg cccaaggtca    3660
acagtgaatc ttgggtcagg aaggctgaga ggtgaagggg aggaatgaga aggtgtgacc    3720
cagactttag acttttataa cagaggctac aaaaaaaaaa aaaaaaa           3767
```

<210> SEQ ID NO 45
<211> LENGTH: 925
<212> TYPE: DNA
<213> ORGANISM: Mouse

<400> SEQUENCE: 45

```
gcgcgcgcgg cgatggaggc ggcggcgacc gtggttttgg ccctggcgct gctcggggcc     60
gcggcgcggg gcgcggcgag tgacgacttc aacctgggcg acgccctgga ggaccccaac    120
atgaagccaa ccccaaggc cccaacgccc aagaagccgt caggaggctt cgacctggag    180
gacgccctgc ccggcggcgg cggaggaggc gcaggagaga agccgggaaa ccggccccag    240
ccggacccga agccgccaag gccacacgga gactcaggcg gcatctcgga cagcgacctg    300
gcagacgccg cgggccaggg aggcggagcc gggcgacgcg ggagcggaga cgaaggcggc    360
catggcggcg ctggcggggc ggagccggaa gggacgcccc agggcttggt gccgggcgtg    420
gtggcggccg tggtggccgc cgtggcgggc gcggtgtcga gcttcgtggc ctatcagcgg    480
cggcgcctgt gcttccgcga gggcggctcc gcccccgtgt agatgacgcc atggcccgc    540 ccctccgggc atcatcgccc cctccagggc cccgatgaca tcactgacgc tgctcatttg    600
catacgcgct ccgccccgct gtgacgtcac tgacccccgcc ccggcctcg cctgaatatg    660 caaatagtcg gccccgcctc ccgccgtgaa atcaccgcct gcaccgcccc tcgccgctgc    720
```

| | |
|---|---|
| atcagtgatg tcactactgc caaagactcc gcccacaact gacctctgac cccggtgaca | 780 |
| tcataacctc cactcacaag gagccatcat gggcagcccc ctgtctcagc tcagcatccc | 840 |
| ctccaggaca ggaaggggcg gagcctgaag gccgggggcg ggaccggaaa taaaggcgga | 900 |
| gttttgtaaa aaaaaaaaaa aaaaa | 925 |

<210> SEQ ID NO 46
<211> LENGTH: 1423
<212> TYPE: DNA
<213> ORGANISM: Mouse

<400> SEQUENCE: 46

| | |
|---|---|
| tctgtgcggc tcaagtgtgt ggccagtggg cacccacggc cagacatcat gtggatgaag | 60 |
| gatgaccaga ccttgacgca tctagaggct agtgaacaca gaaagaagaa gtggacactg | 120 |
| agcttgaaga acctgaagcc tgaagacagt ggcaagtaca cgtgccgtgt atctaacaag | 180 |
| gccggtgcca tcaacgccac ctacaaagtg gatgtaatcc gtgagtggtg ggtctgtggt | 240 |
| aggacagggg cccgtggtgc ctaaaactgt gctgacatgt ttgttttttcc ttggcttaga | 300 |
| gcggactcgt tccaagcctg tgctcacagg gacacaccct gtgaacacaa cggtggactt | 360 |
| cggtgggaca acgtccttcc agtgcaaggt gcgcagtgac gtgaagcctg tgatccagtg | 420 |
| gctgaagcgg gtggagtacg gctccgaggg acgccacaac tccaccattg atgtgggtgg | 480 |
| ccagaagttt gtggtgttgc ccacgggtga tgtgtggtca cggcctgatg gctcctacct | 540 |
| caacaagctg ctcatctctc gggcccgcca ggatgatgct ggcatgtaca tctgcctagg | 600 |
| tgcaaatacc atgggctaca gtttccgtag cgccttcctc actgtattac aggtgtgtg | 660 |
| tgtgggctgc ccaccccatg tttactctca gtctctacca ttggtctggg ctgtcctggg | 720 |
| gttccccaat gtccacttag caagtggggc ctccctatcc ttttcccttc gttgtgggtt | 780 |
| atccttgcct catagggagt tcaggggtgc tgcccatata gttcacattt gggctggttg | 840 |
| ccccattaat atagggacat tctgtcccct actcttcttc ttaatctctc ttgcagaccc | 900 |
| caaacctcca gggcctccta tggcttcttc atcgtcatcc acaagcctgc catggcctgt | 960 |
| ggtgatcggc atcccagctg gtgctgtctt catcctaggc actgtgctgc tctggctttg | 1020 |
| ccagaccaag aagaagccat gtgccccagc atctacactt cctgtgcctg ggcatcgtcc | 1080 |
| cccagggaca tcccgagaac gcagtggtga caaggacctg ccctcattgg ctgtgggcat | 1140 |
| atgtgaggag catggatccg ccatggcccc ccagcacatc ctggcctctg gctcaactgc | 1200 |
| tggccccaag ctgtacccca agctatacac agatgtgcac acacacacac atacacacac | 1260 |
| ctgcactcac acgctctcat gtggagggca aggttcatca acaccagcat gtccactatc | 1320 |
| agtgctaaat acagcgaatc tccaagcact gtgtcctgag gtaggcatat gggggccaag | 1380 |
| gcaacaggtt gggagaattg agaacaatgg aggaagagta tct | 1423 |

<210> SEQ ID NO 47
<211> LENGTH: 464
<212> TYPE: PRT
<213> ORGANISM: Mouse

<400> SEQUENCE: 47

Met Gly Arg Ala Trp Gly Leu Leu Val Gly Leu Leu Gly Val Val Trp
1               5                   10                  15

Leu Leu Arg Leu Gly His Gly Glu Glu Arg Arg Pro Glu Thr Ala Ala
                20                  25                  30

Gln Arg Cys Phe Cys Gln Val Ser Gly Tyr Leu Asp Asp Cys Thr Cys

-continued

```
                 35                  40                  45
Asp Val Glu Thr Ile Asp Lys Phe Asn Asn Tyr Arg Leu Phe Pro Arg
 50                  55                  60
Leu Gln Lys Leu Leu Glu Ser Asp Tyr Phe Arg Tyr Lys Val Asn
 65                  70                  75                  80
Leu Lys Lys Pro Cys Pro Phe Trp Asn Asp Ile Asn Gln Cys Gly Arg
                 85                  90                  95
Arg Asp Cys Ala Val Lys Pro Cys His Ser Asp Glu Val Pro Asp Gly
                100                 105                 110
Ile Lys Ser Ala Ser Tyr Lys Tyr Ser Glu Glu Ala Asn Arg Ile Glu
                115                 120                 125
Glu Cys Glu Gln Ala Glu Arg Leu Gly Ala Val Asp Glu Ser Leu Ser
                130                 135                 140
Glu Glu Thr Gln Lys Ala Val Leu Gln Trp Thr Lys His Asp Asp Ser
145                 150                 155                 160
Ser Asp Ser Phe Cys Glu Ile Asp Asp Ile Gln Ser Pro Asp Ala Glu
                165                 170                 175
Tyr Val Asp Leu Leu Asn Pro Glu Arg Tyr Thr Gly Tyr Lys Gly
                180                 185                 190
Pro Asp Ala Trp Arg Ile Trp Ser Val Ile Tyr Glu Glu Asn Cys Phe
                195                 200                 205
Lys Pro Gln Thr Ile Gln Arg Pro Leu Ala Ser Gly Arg Gly Lys Ser
                210                 215                 220
Lys Glu Asn Thr Phe Tyr Asn Trp Leu Glu Gly Leu Cys Val Glu Lys
225                 230                 235                 240
Arg Ala Phe Tyr Arg Leu Ile Ser Gly Leu His Ala Ser Ile Asn Val
                245                 250                 255
His Leu Ser Ala Arg Tyr Leu Leu Gln Asp Thr Trp Leu Glu Lys Lys
                260                 265                 270
Trp Gly His Asn Val Thr Glu Phe Gln Gln Arg Phe Asp Gly Ile Leu
                275                 280                 285
Thr Glu Gly Glu Gly Pro Arg Arg Leu Arg Asn Leu Tyr Phe Leu Tyr
290                 295                 300
Leu Ile Glu Leu Arg Ala Leu Ser Lys Val Leu Pro Phe Phe Glu Arg
305                 310                 315                 320
Pro Asp Phe Gln Leu Phe Thr Gly Asn Lys Val Gln Asp Ala Glu Asn
                325                 330                 335
Lys Ala Leu Leu Leu Glu Ile Leu His Glu Ile Lys Ser Phe Pro Leu
                340                 345                 350
His Phe Asp Glu Asn Ser Phe Phe Ala Gly Asp Lys Asn Glu Ala His
                355                 360                 365
Lys Leu Lys Glu Asp Phe Arg Leu His Phe Arg Asn Ile Ser Arg Ile
                370                 375                 380
Met Asp Cys Val Gly Cys Phe Lys Cys Arg Leu Trp Gly Lys Leu Gln
385                 390                 395                 400
Thr Gln Gly Leu Gly Thr Ala Leu Lys Ile Leu Phe Ser Glu Lys Leu
                405                 410                 415
Ile Ala Asn Met Pro Glu Ser Gly Pro Ser Tyr Glu Phe Gln Leu Thr
                420                 425                 430
Arg Gln Glu Ile Val Ser Leu Phe Asn Ala Phe Gly Arg Ile Ser Thr
                435                 440                 445
Ser Val Arg Glu Leu Glu Asn Phe Arg His Leu Leu Gln Asn Val His
450                 455                 460
```

<210> SEQ ID NO 48
<211> LENGTH: 664
<212> TYPE: PRT
<213> ORGANISM: Mouse

<400> SEQUENCE: 48

| Met | Lys | Arg | Arg | Asn | Ala | Asp | Cys | Ser | Lys | Leu | Arg | Arg | Pro | Leu | Lys |
|---|---|---|---|---|---|---|---|---|---|---|---|---|---|---|---|
| 1 | | | | 5 | | | | | 10 | | | | | 15 | |

Arg Asn Arg Ile Thr Glu Gly Ile Tyr Gly Ser Thr Phe Leu Tyr Leu
            20                  25                  30

Lys Phe Leu Val Val Trp Ala Leu Val Leu Ala Asp Phe Val Leu
        35                  40                  45

Glu Phe Arg Phe Glu Tyr Leu Trp Pro Phe Trp Leu Phe Ile Arg Ser
 50                  55                  60

Val Tyr Asp Ser Phe Arg Tyr Gln Gly Leu Ala Phe Ser Val Phe Phe
 65                  70                  75                  80

Val Cys Val Ala Phe Thr Ser Asn Ile Ile Cys Leu Leu Phe Ile Pro
                85                  90                  95

Ile Gln Trp Leu Phe Phe Ala Ala Ser Thr Tyr Val Trp Val Gln Tyr
            100                 105                 110

Val Trp His Thr Glu Arg Gly Val Cys Leu Pro Thr Val Ser Leu Trp
        115                 120                 125

Ile Leu Phe Val Tyr Ile Glu Ala Ala Ile Arg Phe Lys Asp Leu Lys
130                 135                 140

Asn Phe His Val Asp Leu Cys Arg Pro Phe Ala Ala His Cys Ile Gly
145                 150                 155                 160

Tyr Pro Val Val Thr Leu Gly Phe Gly Phe Lys Ser Tyr Val Ser Tyr
                165                 170                 175

Lys Met Arg Leu Arg Lys Gln Lys Glu Val Gln Lys Glu Asn Glu Phe
            180                 185                 190

Tyr Met Gln Leu Leu Gln Gln Ala Leu Pro Pro Glu Gln Gln Met Leu
        195                 200                 205

Gln Lys Gln Glu Lys Glu Ala Glu Glu Ala Ala Lys Gly Leu Pro Asp
    210                 215                 220

Met Asp Ser Ser Ile Leu Ile His His Asn Gly Gly Ile Pro Ala Asn
225                 230                 235                 240

Lys Lys Leu Ser Thr Thr Leu Pro Glu Ile Glu Tyr Arg Glu Lys Gly
                245                 250                 255

Lys Glu Lys Asp Lys Asp Ala Lys Lys His Asn Leu Gly Ile Asn Asn
            260                 265                 270

Asn Asn Ile Leu Gln Pro Val Asp Ser Lys Ile Gln Glu Ile Glu Tyr
        275                 280                 285

Met Glu Asn His Ile Asn Ser Lys Arg Leu Asn Asn Asp Leu Val Gly
    290                 295                 300

Ser Thr Glu Asn Leu Leu Lys Glu Asp Ser Cys Thr Ala Ser Ser Lys
305                 310                 315                 320

Asn Tyr Lys Asn Ala Ser Gly Val Val Asn Ser Ser Pro Arg Ser His
                325                 330                 335

Ser Ala Thr Asn Gly Ser Ile Pro Ser Ser Ser Lys Asn Glu Lys
            340                 345                 350

Lys Gln Lys Cys Thr Ser Lys Gly Pro Ser Ala His Lys Asp Leu Met
        355                 360                 365

Glu Asn Cys Ile Pro Asn Asn Gln Leu Ser Lys Pro Asp Ala Leu Val

```
                    370               375               380
Arg Leu Glu Gln Asp Ile Lys Lys Leu Lys Ala Asp Leu Gln Ala Ser
385                 390               395               400

Arg Gln Val Glu Gln Glu Leu Arg Ser Gln Ile Ser Ala Leu Ser Ser
                405               410               415

Thr Glu Arg Gly Ile Arg Ser Glu Met Gly Gln Leu Arg Gln Glu Asn
            420               425               430

Glu Leu Leu Gln Asn Lys Leu His Asn Ala Val Gln Met Lys Gln Lys
        435               440               445

Asp Lys Gln Asn Ile Ser Gln Leu Glu Lys Lys Leu Lys Ala Glu Gln
450               455               460

Glu Ala Arg Ser Phe Val Glu Lys Gln Leu Met Glu Lys Lys Arg
465               470               475               480

Lys Lys Leu Glu Glu Ala Thr Ala Ala Arg Ala Val Ala Phe Ala Ala
                485               490               495

Ala Ser Arg Gly Glu Cys Thr Glu Thr Leu Arg Ser Arg Ile Arg Glu
            500               505               510

Leu Glu Ala Glu Gly Lys Lys Leu Thr Met Asp Met Lys Val Lys Glu
        515               520               525

Glu Gln Ile Arg Glu Leu Glu Leu Lys Val Gln Glu Leu Arg Lys Tyr
    530               535               540

Lys Glu Asn Glu Lys Asp Thr Glu Val Leu Met Ser Ala Leu Ser Ala
545               550               555               560

Met Gln Asp Lys Thr Gln His Leu Glu Asn Ser Leu Ser Ala Glu Thr
                565               570               575

Arg Ile Lys Leu Asp Leu Phe Ser Ala Leu Gly Asp Ala Lys Arg Gln
            580               585               590

Leu Glu Ile Ala Gln Gly Gln Ile Leu Gln Lys Asp Gln Glu Ile Lys
        595               600               605

Asp Leu Lys Gln Lys Ile Ala Glu Val Met Ala Val Met Pro Ser Ile
    610               615               620

Thr Tyr Ser Ala Ala Thr Ser Pro Leu Ser Pro Val Ser Pro His Tyr
625               630               635               640

Ser Ser Lys Phe Val Glu Thr Ser Pro Ser Gly Leu Asp Pro Asn Ala
                645               650               655

Ser Val Tyr Gln Pro Leu Lys Lys
            660

<210> SEQ ID NO 49
<211> LENGTH: 199
<212> TYPE: PRT
<213> ORGANISM: Mouse

<400> SEQUENCE: 49

Met Ala Ser Leu Trp Cys Gly Asn Leu Leu Arg Leu Gly Ser Gly Leu
  1               5                  10                  15

Asn Met Ser Cys Leu Ala Leu Ser Val Leu Leu Ala Gln Leu Thr
                20                  25                  30

Gly Ala Ala Lys Asn Phe Glu Asp Val Arg Cys Lys Cys Ile Cys Pro
            35                  40                  45

Pro Tyr Lys Glu Asn Pro Gly His Ile Tyr Asn Lys Asn Ile Ser Gln
        50                  55                  60

Lys Asp Cys Asp Cys Leu His Val Val Glu Pro Met Pro Val Arg Gly
65                  70                  75                  80
```

-continued

```
Pro Asp Val Glu Ala Tyr Cys Leu Arg Cys Glu Cys Lys Tyr Glu Glu
                85                  90                  95

Arg Ser Ser Val Thr Ile Lys Val Thr Ile Ile Tyr Leu Ser Ile
            100                 105                 110

Leu Gly Leu Leu Leu Tyr Met Val Tyr Leu Thr Leu Val Glu Pro
            115                 120                 125

Ile Leu Lys Arg Arg Leu Phe Gly His Ser Gln Leu Leu Gln Ser Asp
130                     135                 140

Asp Asp Val Gly Asp His Gln Pro Phe Ala Asn Ala His Asp Val Leu
145                 150                 155                 160

Ala Arg Ser Arg Ser Arg Ala Asn Val Leu Asn Lys Val Glu Tyr Ala
                165                 170                 175

Gln Gln Arg Trp Lys Leu Gln Val Gln Glu Gln Arg Lys Ser Val Phe
            180                 185                 190

Asp Arg His Val Val Leu Ser
            195

<210> SEQ ID NO 50
<211> LENGTH: 227
<212> TYPE: PRT
<213> ORGANISM: Mouse

<400> SEQUENCE: 50

Met Gly Pro Leu His Gln Phe Leu Leu Leu Ile Thr Ala Leu Ser
1               5                   10                  15

Gln Ala Leu Asn Thr Thr Val Leu Gln Gly Met Ala Gly Gln Ser Leu
            20                  25                  30

Arg Val Ser Cys Thr Tyr Asp Ala Leu Lys His Trp Gly Arg Arg Lys
        35                  40                  45

Ala Trp Cys Arg Gln Leu Gly Glu Glu Gly Pro Cys Gln Arg Val Val
    50                  55                  60

Ser Thr His Gly Val Trp Leu Leu Ala Phe Leu Lys Lys Arg Asn Gly
65                  70                  75                  80

Ser Thr Val Ile Ala Asp Asp Thr Leu Ala Gly Thr Val Thr Ile Thr
                85                  90                  95

Leu Lys Asn Leu Gln Ala Gly Asp Ala Gly Leu Tyr Gln Cys Gln Ser
            100                 105                 110

Leu Arg Gly Arg Glu Ala Glu Val Leu Gln Lys Val Leu Val Glu Val
        115                 120                 125

Leu Glu Asp Pro Leu Asp Asp Gln Asp Ala Gly Asp Leu Trp Val Pro
    130                 135                 140

Glu Glu Ser Ser Ser Phe Glu Gly Ala Gln Val Glu His Ser Thr Ser
145                 150                 155                 160

Arg Asn Gln Glu Thr Ser Phe Pro Pro Thr Ser Ile Leu Leu Leu Leu
                165                 170                 175

Ala Cys Val Leu Leu Ser Lys Phe Leu Ala Ala Ser Ile Leu Trp Ala
            180                 185                 190

Val Ala Arg Gly Arg Gln Lys Pro Gly Thr Pro Val Val Arg Gly Leu
        195                 200                 205

Asp Cys Gly Gln Asp Ala Gly His Gln Leu Gln Ile Leu Thr Gly Pro
    210                 215                 220

Gly Gly Thr
225

<210> SEQ ID NO 51
```

```
<211> LENGTH: 503
<212> TYPE: PRT
<213> ORGANISM: Mouse

<400> SEQUENCE: 51

Met Gly Thr Gly Ala Gly Gly Pro Ser Val Leu Ala Leu Leu Phe Ala
 1               5                  10                  15

Val Cys Ala Pro Leu Arg Leu Gln Ala Glu Leu Gly Asp Gly Cys
             20                  25                  30

Gly His Ile Val Thr Ser Gln Asp Ser Gly Thr Met Thr Ser Lys Asn
             35                  40                  45

Tyr Pro Gly Thr Tyr Pro Asn Tyr Thr Val Cys Glu Lys Ile Ile Thr
 50                  55                  60

Val Pro Lys Gly Lys Arg Leu Ile Leu Arg Leu Gly Asp Leu Asn Ile
65                  70                  75                  80

Glu Ser Lys Thr Cys Ala Ser Asp Tyr Leu Leu Phe Ser Ser Ala Thr
                 85                  90                  95

Asp Gln Tyr Gly Pro Tyr Cys Gly Ser Trp Ala Val Pro Lys Glu Leu
                100                 105                 110

Arg Leu Asn Ser Asn Glu Val Thr Val Leu Phe Lys Ser Gly Ser His
            115                 120                 125

Ile Ser Gly Arg Gly Phe Leu Leu Thr Tyr Ala Ser Ser Asp His Pro
130                 135                 140

Asp Leu Ile Thr Cys Leu Glu Arg Gly Ser His Tyr Phe Glu Glu Lys
145                 150                 155                 160

Tyr Ser Lys Phe Cys Pro Ala Gly Cys Arg Asp Ile Ala Arg Asp Ile
                165                 170                 175

Ser Gly Asn Thr Lys Asp Gly Tyr Arg Asp Thr Ser Leu Leu Cys Lys
            180                 185                 190

Ala Ala Ile His Ala Gly Ile Ile Thr Asp Glu Leu Gly Gly His Ile
            195                 200                 205

Asn Leu Leu Gln Ser Lys Gly Ile Ser His Tyr Glu Gly Leu Leu Ala
210                 215                 220

Asn Gly Val Leu Ser Arg His Gly Ser Leu Ser Glu Lys Arg Phe Leu
225                 230                 235                 240

Phe Thr Thr Pro Gly Met Asn Ile Thr Thr Val Ala Ile Pro Ser Val
                245                 250                 255

Ile Phe Ile Ala Leu Leu Leu Thr Gly Met Gly Ile Phe Ala Ile Cys
                260                 265                 270

Arg Lys Arg Lys Lys Gly Asn Pro Tyr Val Ser Ala Asp Ala Gln
                275                 280                 285

Lys Thr Gly Cys Trp Lys Gln Ile Lys Tyr Pro Phe Ala Arg His Gln
    290                 295                 300

Ser Thr Glu Phe Thr Ile Ser Tyr Asp Asn Glu Lys Glu Met Thr Gln
305                 310                 315                 320

Lys Leu Asp Leu Ile Thr Ser Asp Met Ala Asp Tyr Gln Gln Pro Leu
                325                 330                 335

Met Ile Gly Thr Gly Thr Val Ala Arg Lys Gly Ser Thr Phe Arg Pro
                340                 345                 350

Met Asp Thr Asp Thr Glu Glu Val Arg Val Asn Thr Glu Ala Ser Gly
            355                 360                 365

His Tyr Asp Cys Pro His Arg Pro Gly Arg His Glu Tyr Ala Leu Pro
370                 375                 380

Leu Thr His Ser Glu Pro Glu Tyr Ala Thr Pro Ile Val Glu Arg His
```

```
                385                 390                 395                 400
Leu Leu Arg Ala His Thr Phe Ser Thr Gln Ser Gly Tyr Arg Val Pro
                405                 410                 415

Gly Pro Arg Pro Thr His Glu His Ser His Ser Ser Gly Gly Phe Pro
                420                 425                 430

Pro Ala Thr Gly Ala Thr Gln Val Glu Ser Tyr Gln Arg Pro Ala Ser
                435                 440                 445

Pro Lys Pro Val Gly Gly Tyr Asp Lys Pro Ala Ala Ser Ser Phe
            450                 455                 460

Leu Asp Ser Arg Asp Pro Ala Ser Gln Ser Gln Met Thr Ser Gly Gly
465                 470                 475                 480

Asp Asp Gly Tyr Ser Ala Pro Arg Asn Gly Leu Ala Pro Leu Asn Gln
                485                 490                 495

Thr Ala Met Thr Ala Leu Leu
                500

<210> SEQ ID NO 52
<211> LENGTH: 757
<212> TYPE: PRT
<213> ORGANISM: Mouse

<400> SEQUENCE: 52

Met Met Trp Pro Gln Pro Pro Thr Phe Ser Leu Phe Leu Leu Leu Leu
1               5                   10                  15

Leu Ser Gln Ala Pro Ser Ser Arg Pro Gln Ser Ser Gly Thr Lys Lys
                20                  25                  30

Leu Arg Leu Val Gly Pro Ala Asp Arg Pro Lys Glu Gly Arg Leu Glu
                35                  40                  45

Val Leu His Gln Gly Gln Trp Gly Thr Val Cys Asp Asp Phe Ala
            50                  55                  60

Leu Gln Glu Ala Thr Val Ala Cys Arg Gln Leu Gly Phe Glu Ser Ala
65                  70                  75                  80

Leu Thr Trp Ala His Ser Ala Lys Tyr Gly Gln Gly Glu Gly Pro Ile
                85                  90                  95

Trp Leu Asp Asn Val Arg Cys Leu Gly Thr Glu Lys Thr Leu Asp Gln
                100                 105                 110

Cys Gly Ser Asn Gly Trp Gly Ile Ser Asp Cys Arg His Ser Glu Asp
                115                 120                 125

Val Gly Val Val Cys His Pro Arg Arg Gln His Gly Tyr His Ser Glu
            130                 135                 140

Lys Val Ser Asn Ala Leu Gly Pro Gln Gly Arg Arg Leu Glu Glu Val
145                 150                 155                 160

Arg Leu Lys Pro Ile Leu Ala Ser Ala Lys Arg His Ser Pro Val Thr
                165                 170                 175

Glu Gly Ala Val Glu Val Arg Tyr Asp Gly His Trp Arg Gln Val Cys
                180                 185                 190

Asp Gln Gly Trp Thr Met Asn Asn Ser Arg Val Val Cys Gly Met Leu
            195                 200                 205

Gly Phe Pro Ser Gln Thr Ser Val Asn Ser His Tyr Tyr Arg Lys Val
    210                 215                 220

Trp Asn Leu Lys Met Lys Asp Pro Lys Ser Arg Leu Asn Ser Leu Thr
225                 230                 235                 240

Lys Lys Asn Ser Phe Trp Ile His Arg Val Asp Cys Phe Gly Thr Glu
                245                 250                 255
```

```
Pro His Leu Ala Lys Cys Gln Val Gln Val Ala Pro Gly Arg Gly Lys
            260                 265                 270

Leu Arg Ala Ala Cys Pro Gly Gly Met His Ala Val Val Ser Cys Val
        275                 280                 285

Ala Gly Pro His Phe Arg Arg Gln Lys Pro Lys Pro Thr Arg Lys Glu
    290                 295                 300

Ser His Ala Glu Glu Leu Lys Val Arg Leu Arg Ser Gly Ala Gln Val
305                 310                 315                 320

Gly Glu Gly Arg Val Glu Val Leu Met Asn Arg Gln Trp Gly Thr Val
                325                 330                 335

Cys Asp His Arg Trp Asn Leu Ile Ser Ala Ser Val Val Cys Arg Gln
                340                 345                 350

Leu Gly Phe Gly Ser Ala Arg Glu Ala Leu Phe Gly Ala Gln Leu Gly
            355                 360                 365

Gln Gly Leu Gly Pro Ile His Leu Ser Glu Val Arg Cys Arg Gly Tyr
        370                 375                 380

Glu Arg Thr Leu Gly Asp Cys Leu Ala Leu Glu Gly Ser Gln Asn Gly
385                 390                 395                 400

Cys Gln His Ala Asn Asp Ala Ala Val Arg Cys Asn Ile Pro Asp Met
                405                 410                 415

Gly Phe Gln Asn Lys Val Arg Leu Ala Gly Gly Arg Asn Ser Glu Glu
            420                 425                 430

Gly Val Val Glu Val Gln Val Glu Val Asn Gly Val Pro Arg Trp Gly
        435                 440                 445

Thr Val Cys Ser Asp His Trp Gly Leu Thr Glu Ala Met Val Thr Cys
    450                 455                 460

Arg Gln Leu Gly Leu Gly Phe Ala Asn Phe Ala Leu Lys Asp Thr Trp
465                 470                 475                 480

Tyr Trp Gln Gly Thr Pro Glu Ala Lys Glu Val Val Met Ser Gly Val
                485                 490                 495

Arg Cys Ser Gly Thr Glu Met Ala Leu Gln Gln Cys Gln Arg His Gly
                500                 505                 510

Pro Val His Cys Ser His Gly Pro Gly Arg Phe Ser Ala Gly Val Ala
            515                 520                 525

Cys Met Asn Ser Ala Pro Asp Leu Val Met Asn Ala Gln Leu Val Gln
        530                 535                 540

Glu Thr Ala Tyr Leu Glu Asp Arg Pro Leu Ser Met Leu Tyr Cys Ala
545                 550                 555                 560

His Glu Glu Asn Cys Leu Ser Lys Ser Ala Asp His Met Asp Trp Pro
                565                 570                 575

Tyr Gly Tyr Arg Arg Leu Leu Arg Phe Ser Ser Gln Ile Tyr Asn Leu
                580                 585                 590

Gly Arg Ala Asp Phe Arg Pro Lys Ala Gly Arg His Ser Trp Ile Trp
            595                 600                 605

His Gln Cys His Arg His Tyr His Ser Ile Glu Val Phe Thr His Tyr
        610                 615                 620

Asp Leu Leu Thr Leu Asn Gly Ser Lys Val Ala Glu Gly His Lys Ala
625                 630                 635                 640

Ser Phe Cys Leu Glu Asp Thr Asn Cys Pro Ser Gly Val Gln Arg Arg
                645                 650                 655

Tyr Ala Cys Ala Asn Phe Gly Glu Gln Gly Val Ala Val Gly Cys Trp
                660                 665                 670

Asp Thr Tyr Arg His Asp Ile Asp Cys Gln Trp Val Asp Ile Thr Asp
```

-continued

```
                675                 680                 685
Val Gly Pro Gly Asp Tyr Ile Phe Gln Val Val Asn Pro Thr Asn
    690                 695                 700

Asp Val Ala Glu Ser Asp Phe Ser Asn Asn Met Ile Arg Cys Arg Cys
705                 710                 715                 720

Lys Tyr Asp Gly Gln Arg Val Trp Leu His Asn Cys His Thr Gly Asp
                725                 730                 735

Ser Tyr Arg Ala Asn Ala Glu Leu Ser Leu Glu Gln Glu Gln Arg Leu
                740                 745                 750

Arg Asn Asn Leu Ile
            755

<210> SEQ ID NO 53
<211> LENGTH: 169
<212> TYPE: PRT
<213> ORGANISM: Mouse

<400> SEQUENCE: 53

Met Glu Ala Ala Ala Thr Val Val Leu Ala Leu Ala Leu Leu Gly Ala
1               5                   10                  15

Ala Ala Arg Gly Ala Ala Ser Asp Asp Phe Asn Leu Gly Asp Ala Leu
                20                  25                  30

Glu Asp Pro Asn Met Lys Pro Thr Pro Lys Ala Pro Thr Pro Lys Lys
            35                  40                  45

Pro Ser Gly Gly Phe Asp Leu Glu Asp Ala Leu Pro Gly Gly Gly Gly
    50                  55                  60

Gly Gly Ala Gly Glu Lys Pro Gly Asn Arg Pro Gln Pro Asp Pro Lys
65                  70                  75                  80

Pro Pro Arg Pro His Gly Asp Ser Gly Gly Ile Ser Asp Ser Asp Leu
                85                  90                  95

Ala Asp Ala Ala Gly Gln Gly Gly Ala Gly Arg Arg Gly Ser Gly
                100                 105                 110

Asp Glu Gly Gly His Gly Gly Ala Gly Gly Ala Glu Pro Glu Gly Thr
            115                 120                 125

Pro Gln Gly Leu Val Pro Gly Val Val Ala Val Val Ala Ala Val
    130                 135                 140

Ala Gly Ala Val Ser Ser Phe Val Ala Tyr Gln Arg Arg Arg Leu Cys
145                 150                 155                 160

Phe Arg Glu Gly Gly Ser Ala Pro Val
                165

<210> SEQ ID NO 54
<211> LENGTH: 30
<212> TYPE: DNA
<213> ORGANISM: Artificial Sequence
<220> FEATURE:
<223> OTHER INFORMATION: Made in a lab

<400> SEQUENCE: 54
cccaagctta tgacgcggag ccccgcgctg                                    30

<210> SEQ ID NO 55
<211> LENGTH: 35
<212> TYPE: DNA
<213> ORGANISM: Artificial Sequence
<220> FEATURE:
<223> OTHER INFORMATION: Made in a lab

<400> SEQUENCE: 55
```

```
cgggatccag gccatggcag gcttgtggat gacga                                35
```

<210> SEQ ID NO 56
<211> LENGTH: 37
<212> TYPE: DNA
<213> ORGANISM: Artificial Sequence
<220> FEATURE:
<223> OTHER INFORMATION: Made in a lab

<400> SEQUENCE: 56

```
ccgctcgagt agatactctt cctccattgt tctcatt                              37
```

<210> SEQ ID NO 57
<211> LENGTH: 18
<212> TYPE: DNA
<213> ORGANISM: Artificial Sequence
<220> FEATURE:
<223> OTHER INFORMATION: Made in a lab

<400> SEQUENCE: 57

```
ctgtgcggct caagtgtg                                                   18
```

<210> SEQ ID NO 58
<211> LENGTH: 3503
<212> TYPE: DNA
<213> ORGANISM: Mouse

<400> SEQUENCE: 58

```
gactgattcg cctgcaggtc gacactagtg gatccaaaga attcggcacg aggcggagtc     60
ccgcctcgcc gccccctcgag cgcccccagc ttctctgctg gccggaacct gcaccccgaa   120
ccaggaagca cctggcggcg ggcgcgggat ggctgggccc agctgggtgc tccctcggct    180
ggacggtttc atccttaccg agcgcctggg cagtggcacg tacgccacgg tgtacaaggc    240
ctacgccaag aaggatactc gggaagtggt agccataaaa tgcgtggcca agaagagtct    300
caacaaggcg tcagtggaaa acctcctgac tgagattgag atcctcaagg gcattcggca    360
ccccatatc gtgcagctga aagacttcca gtgggacaat gacaatatct acctcatcat    420
ggagttctgt gcaggggggtg acctgtctcg cttcattcat acccgcagga tcctgcctga   480
gaaggtggcc cgtgttttca tgcagcagtt ggctagtgcc ctgcagttcc tgcatgaacg    540
aaacatctct cacttggatc tgaaaccgca gaacatcctg ctgagctctt ggagaagcc     600
ccacctgaaa ctggcagact ttggctttgc ccagcacatg tccccgtggg acgaaaaaca    660
cgtgctccgt ggctccccgc tctatatggc tcctgagatg gtgtgtcggc ggcagtatga    720
tgcgcgtgtg gacctctggt ctgtgggggt gatcctgtac gaagccctct ttgggcagcc    780
cccctttgcc tccagatcgt tctcagagct agaagaaaag attcgcagca atcgggtgat    840
tgaggtgcgt ctggcagggt ctaggcatcc accggggatt gagggactca aggcccagaa    900
gtttgttcag cactgcagtg caggctctgg gcctttcatg gcagtggggc atgttctgtg    960
gtggaagcct agagtctggt ccgttcctga ggatccatat cagccacgac aggcaacaaa   1020
tgaccaggcc caatcttccc atagtccggg gctggaggca atacccatt tgataggaga    1080
ctgataaagg atgcttggct ctcttcctgc acatcaccgg gacttgccat gatccactca   1140
gattacccac agcaaacacg tacccttatg ggggttccta acaggccttg ggctttgggc   1200
tcagatgttg gagccttctg tgatgtgtct ctgctctatg cctctgtagc tccctcttcg   1260
gcccaactct ccctagactg ccgggacctg ttgcagcgac ttctagagcg ggaccccgcc   1320
```

```
cgtcgaatct ccttcaagga cttctttgcc catccctggg tggacctgga gcacatgccc    1380
agtggggaga gcctggcaca ggcaagggcc cttgtggtgg aggctgtgaa gaaggaccag    1440 gaggggatg ctgccgctgc cctgtcgctc tactgcaagg ctctggactt ctttgtacct     1500
gcgctacact gtgagaacca ggccattcct ataacctgtg tgcagagggg ggcaggagtt    1560
gggtcaggct ccccattcag agcttagggg agatggtgca gaagatcaac gtggaactga    1620
gtatctgaag attgcaaagg gcttactgtg gggtaggctt tcaggacagc atcctcatat    1680
gaacccttca ccttctgcag acgaagtgga tgcccagagg aaggaggcaa ttaaggcgaa    1740
ggtgggacag tatgtgtccc gggcagagga gctcaaagcc attgtctcct cctccaatca    1800
ggccctgcta agacagggca caactgtcca agagctgctt cgaggctgct ccctcaccat    1860
gagcctttac tctcacatca gagatggccc gtgacaaacc acgcctcctg gctgccctgg    1920
aagtggcctc agctgccctg gccaaggagg aggaagctgg caaagagcag gatgccctgg    1980
acctgtacca gcacagcctc ggggagctgc tagtgctgtt ggcagcagag gccccaggcc    2040
gaaggcggga gctccttcac accgaggttc agaacctcat ggctcgagct gaatacctga    2100
aggagcagat caagataagg gagtctcact gggaagcgga gagtctggac aaagaggggc    2160
tgtcggagtc tgttcgtagt tcttgcacac tgcagtgaca ccggaaggag cagcggatgg    2220
agcacaaccc tagagagaag ctgcattacc aactcaggtt gacacctgca cacctgggac    2280
cttcctggac gagcagctcc cacatgctgg ttcccagcat tcctctgagt gttctccacc    2340
cttggggcgt ctggtggcag gtgtactaag ctctgggaga attacttgaa tgtgaccttg    2400
tcattaggtg actgctggtc taagcctgtc cggcttcagg acaccatcac cccgttgtgt    2460
tttgttctgc aaagaggacg tcatgcctct tcaggacact tgctaccaga cagctgctgt    2520
acctgggcca ccctccctg ggagccttta ttccaaccct actttttttc ttgcactgga     2580
atgggacact cggatacct cagggactac ctacctgaca gtatgctctc ggctctcaga     2640
cctctccagt cttcctgcga gctcagagct gccatccttt tcagttcttt aagacaatcc    2700
ttcatgcatg aaagtcatgc cctttgtaaa ggtggaatac atgtgagaac cccagacctt    2760
ccctgccttg gcatggagga ggggtcctca tacccccact tacagctctc tttgagggga    2820
tatgccacac tagtcacatg gtggaccctg agctagagct gggtcttggc tgggtcttcc    2880
cctctgtcct attaagctat ggatacatcc acagcttata ccctgtatga gctggagaag    2940
aacttacgta tctggagtta ctggaagatt gctctttttt ttttttcttct ttaaacaccc    3000 cctcccccag gtcatcatct tgtttcagat ttttattcaa attcttattg aaggctgatt    3060
tttgaataag gagcagagga gctgttctgc cacaaatgac ccccaaatga caggcactga    3120
gactttcttt cttccttcct tccttccttc cttccttcct tccttccttc cttccttcct    3180
tccttccttt ctttctttct ttctttcttt ctttctttct ttctttcttt ctttctttct    3240
ttcttctttc ttcctctgtg tgtgtgtggg gtgtgtgtgt gtgtgtgtgt gtgtgtgtgt    3300
gtgtgtgtgt aaagggttat ttttaaagtt agagaatact ggtgattttc aatcattctg    3360
cccttaaccg cctccttagg gcaaaatgga acaccctcct tgctaaaggc tggatgtatg    3420
taaagacaat agttcattgt ttctctatta aattattttc cctccttaaa aaaaaaaaa    3480 aaaaaaaaaa aaaaaaaaaa aaa                                            3503
```

<210> SEQ ID NO 59
<211> LENGTH: 311
<212> TYPE: PRT
<213> ORGANISM: Mouse

<400> SEQUENCE: 59

```
Met Ala Gly Pro Ser Trp Gly Leu Pro Arg Leu Asp Gly Phe Ile Leu
1               5                   10                  15

Thr Glu Arg Leu Gly Ser Gly Thr Tyr Ala Thr Val Tyr Lys Ala Tyr
            20                  25                  30

Ala Lys Lys Asp Thr Arg Glu Val Val Ala Ile Lys Cys Val Ala Lys
        35                  40                  45

Lys Ser Leu Asn Lys Ala Ser Val Glu Asn Leu Leu Thr Glu Ile Glu
    50                  55                  60

Ile Leu Lys Gly Ile Arg His Pro His Ile Val Gln Leu Lys Asp Phe
65                  70                  75                  80

Gln Trp Asp Asn Asp Asn Ile Tyr Leu Ile Met Glu Phe Cys Ala Gly
                85                  90                  95

Gly Asp Leu Ser Arg Phe Ile His Thr Arg Arg Ile Leu Pro Glu Lys
            100                 105                 110

Val Ala Arg Val Phe Met Gln Gln Leu Ala Ser Ala Leu Gln Phe Leu
        115                 120                 125

His Glu Arg Asn Ile Ser His Leu Asp Leu Lys Pro Gln Asn Ile Leu
    130                 135                 140

Leu Ser Ser Leu Glu Lys Pro His Leu Lys Leu Ala Asp Phe Gly Phe
145                 150                 155                 160

Ala Gln His Met Ser Pro Trp Asp Glu Lys His Val Leu Arg Gly Ser
                165                 170                 175

Pro Leu Tyr Met Ala Pro Glu Met Val Cys Arg Arg Gln Tyr Asp Ala
            180                 185                 190

Arg Val Asp Leu Trp Ser Val Gly Val Ile Leu Tyr Glu Ala Leu Phe
        195                 200                 205

Gly Gln Pro Pro Phe Ala Ser Arg Ser Phe Ser Glu Leu Glu Glu Lys
    210                 215                 220

Ile Arg Ser Asn Arg Val Ile Glu Val Arg Leu Ala Gly Ser Arg His
225                 230                 235                 240

Pro Pro Gly Ile Glu Gly Leu Lys Ala Gln Lys Phe Val Gln His Cys
                245                 250                 255

Ser Ala Gly Ser Gly Pro Phe Met Ala Val Gly His Val Leu Trp Trp
            260                 265                 270

Lys Pro Arg Val Trp Ser Val Pro Glu Asp Pro Tyr Gln Pro Arg Gln
        275                 280                 285

Ala Thr Asn Asp Gln Ala Gln Ser Ser His Ser Pro Gly Leu Glu Ala
    290                 295                 300

Asn Thr His Leu Ile Gly Asp
305                 310
```

<210> SEQ ID NO 60
<211> LENGTH: 373
<212> TYPE: PRT
<213> ORGANISM: Mouse

<400> SEQUENCE: 60

```
Met Thr Arg Ser Pro Ala Leu Leu Leu Leu Leu Gly Ala Leu Pro
1               5                   10                  15

Ser Ala Glu Ala Ala Arg Gly Pro Arg Met Ala Asp Lys Val Val
            20                  25                  30

Pro Arg Gln Val Ala Arg Leu Gly Arg Thr Val Arg Leu Gln Cys Pro
        35                  40                  45
```

```
Val Glu Gly Asp Pro Pro Leu Thr Met Trp Thr Lys Asp Gly Arg
    50                  55                  60

Thr Ile His Ser Gly Trp Ser Arg Phe Arg Val Leu Pro Gln Gly Leu
65                  70                  75                  80

Lys Val Lys Glu Val Glu Ala Glu Asp Ala Gly Val Tyr Val Cys Lys
                85                  90                  95

Ala Thr Asn Gly Phe Gly Ser Leu Ser Val Asn Tyr Thr Leu Ile Ile
                100                 105                 110

Met Asp Asp Ile Ser Pro Gly Lys Glu Ser Pro Gly Pro Gly Gly Ser
                115                 120                 125

Ser Gly Gly Gln Glu Asp Pro Ala Ser Gln Gln Trp Ala Arg Pro Arg
130                 135                 140

Phe Thr Gln Pro Ser Lys Met Arg Arg Arg Val Ile Ala Arg Pro Val
145                 150                 155                 160

Gly Ser Ser Val Arg Leu Lys Cys Val Ala Ser Gly His Pro Arg Pro
                165                 170                 175

Asp Ile Met Trp Met Lys Asp Gln Thr Leu Thr His Leu Glu Ala
                180                 185                 190

Ser Glu His Arg Lys Lys Lys Trp Thr Leu Ser Leu Lys Asn Leu Lys
                195                 200                 205

Pro Glu Asp Ser Gly Lys Tyr Thr Cys Arg Val Ser Asn Lys Ala Gly
                210                 215                 220

Ala Ile Asn Ala Thr Tyr Lys Val Asp Val Ile Gln Arg Thr Arg Ser
225                 230                 235                 240

Lys Pro Val Leu Thr Gly Thr His Pro Val Asn Thr Thr Val Asp Phe
                245                 250                 255

Gly Gly Thr Thr Ser Phe Gln Cys Lys Val Arg Ser Asp Val Lys Pro
                260                 265                 270

Val Ile Gln Trp Leu Lys Arg Val Glu Tyr Gly Ser Glu Gly Arg His
                275                 280                 285

Asn Ser Thr Ile Asp Val Gly Gly Gln Lys Phe Val Val Leu Pro Thr
                290                 295                 300

Gly Asp Val Trp Ser Arg Pro Asp Gly Ser Tyr Leu Asn Lys Leu Leu
305                 310                 315                 320

Ile Ser Arg Ala Arg Gln Asp Asp Ala Gly Met Tyr Ile Cys Leu Gly
                325                 330                 335

Ala Asn Thr Met Gly Tyr Ser Phe Arg Ser Ala Phe Leu Thr Val Leu
                340                 345                 350

Pro Asp Pro Lys Pro Pro Gly Pro Pro Met Ala Ser Ser Ser Ser Ser
                355                 360                 365

Thr Ser Leu Pro Trp
    370

<210> SEQ ID NO 61
<211> LENGTH: 135
<212> TYPE: PRT
<213> ORGANISM: Mouse

<400> SEQUENCE: 61

Cys Gln Thr Lys Lys Pro Cys Ala Pro Ala Ser Thr Leu Pro Val
1               5                   10                  15

Pro Gly His Arg Pro Pro Gly Thr Ser Arg Glu Arg Ser Gly Asp Lys
                20                  25                  30

Asp Leu Pro Ser Leu Ala Val Gly Ile Cys Glu Glu His Gly Ser Ala
```

-continued

```
                    35                  40                  45
Met Ala Pro Gln His Ile Leu Ala Ser Gly Ser Thr Ala Gly Pro Lys
    50                  55                  60

Leu Tyr Pro Lys Leu Tyr Thr Asp Val His Thr His Thr His Thr His
65              70                  75                  80

Thr Cys Thr His Thr Leu Ser Cys Gly Gly Gln Gly Ser Ser Thr Pro
                85                  90                  95

Ala Cys Pro Leu Ser Val Leu Asn Thr Ala Asn Leu Gln Ala Leu Cys
            100                 105                 110

Pro Glu Val Gly Ile Trp Gly Pro Arg Gln Gln Val Gly Arg Ile Glu
        115                 120                 125

Asn Asn Gly Gly Arg Val Ser
    130                 135
```

METHODS FOR ENHANCING IMMUNE RESPONSES BY FIBROBLAST GROWTH FACTOR RECEPTOR 5 POLYPEPTIDES

This application is a continuation-in-part of U.S. patent application Ser. No. 09/383,586, filed Aug. 26, 1999, now U.S. Pat. No. 6,242,419; which is a continuation-in-part of U.S. patent application Ser. No. 09/276,268, filed Mar. 25, 1999, now abandoned; and claims priority to International Patent Application No. PCT/NZ00/00015, filed Feb. 18, 2000; and to U.S. Provisional Patent Application No. 60/221,216, filed Jul. 25, 2000.

TECHNICAL FIELD OF THE INVENTION

This invention relates to polynucleotides and polypeptides derived from lymph node stromal cells from flaky skin (fsn -/-) mice and their use in therapeutic methods.

BACKGROUND OF THE INVENTION

Lymph vessels and nodes are important components of the body's immune system. Lymph nodes are small lymphatic organs that are located in the path of lymph vessels. Large molecules and cells, including foreign substances, enter into the lymphatic vessels and, in circulating through these vessels, pass through the lymph nodes. Here, any foreign substances are concentrated and exposed to lymphocytes. This triggers a cascade of events that constitute an immune response, protecting the body from infection and from cancer.

Lymph nodes are surrounded by a dense connective tissue network that forms a supporting capsule. This network extends into the body of the lymph node, forming an additional framework of support. Throughout the remainder of the organ, a fine meshwork can be identified that comprises reticular fibres and the reticular cells that produce and surround the fibres. These features provide a support for the main functional cells of the lymphatic system, which are T- and B-lymphocytes. Additional cell types found in lymph nodes include macrophages, follicular dendritic cells, and endothelial cells that line the blood vessels servicing the node.

The cells within lymph nodes communicate with each other in order to defend the body against foreign substances. When a foreign substance, or antigen, is present, it is detected by macrophages and follicular dendritic cells that take up and process the antigen, and display parts of it on their cell surface. These cell surface antigens are then presented to T- and B-lymphocytes, causing them to proliferate and differentiate into activated T-lymphocytes and plasma cells, respectively. These cells are released into the circulation in order to seek out and destroy antigen. Some T- and B-lymphocytes will also differentiate into memory cells. Should these cells come across the same antigen at a later date, the immune response will be more rapid.

Once activated T- and B-lymphocytes are released into the circulation, they can perform a variety of functions that lead to the eventual destruction of antigen. Activated T-lymphocytes can differentiate into cytotoxic lymphocytes (also known as killer T-cells) which recognise other cells that have foreign antigens on their surface and kill the cell by causing them to lyse. Activated T-lymphocytes can also differentiate into helper T-cells which will then secrete proteins in order to stimulate B-lymphocytes, and other T-lymphocytes, to respond to antigens. In addition, activated T-lymphocytes can differentiate into suppressor T-cells which secrete factors that suppress the activity of B-lymphocytes. Activated B-lymphocytes differentiate into plasma cells, which synthesise and secrete antibodies that bind to foreign antigens. The antibody-antigen complex is then detected and destroyed by macrophages, or by a group of blood constituents known as complement.

Lymph nodes can be dissociated and the resulting cells grown in culture. Cells that adhere to the tissue culture dishes can be maintained for some length of time and are known as stromal cells. The cultured cells are a heterogeneous population and can be made up of most cells residing within lymph nodes, such as reticular cells, follicular dendritic cells, macrophages and endothelial cells. It is well known that bone marrow stromal cells play a critical role in homing, growth and differentiation of hematopoietic progenitor cells. Proteins produced by stromal cells are necessary for the maintenance of plasma cells in vitro. Furthermore, stromal cells are known to secrete factors and present membrane-bound receptors that are necessary for the survival of lymphoma cells.

An autosomal recessive mutation, designated flaky skin (fsn -/-), has been described in the inbred A/J mouse strain (The Jackson Laboratory, Bar Harbour, Me.). The mice have a skin disorder similar to psoriasis in humans. Psoriasis is a common disease affecting 2% of the population, which is characterised by a chronic inflammation associated with thickening and scaling of the skin. Histology of skin lesions shows increased proliferation of the cells in the epidermis, the uppermost layer of skin, together with the abnormal presence of inflammatory cells, including lymphocytes, in the dermis, the layer of skin below the epidermis. While the cause of the disease is unclear, psoriasis is associated with a disturbance of the immune system involving T lymphocytes. The disease occurs more frequently in family members, indicating the involvement of a genetic factor as well. Mice with the fsn gene mutation have not only a psoriatic-like skin disease but also other abnormalities involving cells of the immune and hematopoietic system. These mice have markedly increased numbers of lymphocytes associated with enlarged lymphoid organs, including the spleen and lymph nodes. In addition, their livers are enlarged, and the mice are anaemic. Genes and proteins expressed in abnormal lymph nodes of fsn-/- mice may thus influence the development or function of cells of the immune and hematopoietic system, the response of these cells in inflammatory disorders, and the responses of skin and other connective tissue cells to inflammatory signals.

There is a need in the art to identify genes encoding proteins that function to modulate all cells of the immune system. These proteins from normal or abnormal lymph nodes may be useful in modifying the immune responses to tumour cells or infectious agents such as bacteria, viruses, protozoa and worms. Such proteins may be useful in the treatment of disorders where the immune system initiates unfavourable reactions to the body, including Type I hypersensitivity reactions (such as hay fever, eczema, allergic rhinitis and asthma), and Type II hypersensitivity reactions (such as transfusion reactions and haemolytic disease of newborns). Other unfavourable reactions are initiated during Type III reactions, which are due to immune complexes forming in infected organs during persistent infection or in the lungs following repeated inhalation of materials from moulds, plants or animals, and in Type IV reactions in diseases such as leprosy, schistosomiasis and dermatitis.

Novel proteins of the immune system may also be useful in treating autoimmune diseases where the body recognises itself as foreign. Examples of such diseases include rheumatoid arthritis, Addison's disease, ulcerative colitis, dermatomyositis and lupus. Such proteins may also be useful during tissue transplantation, where the body will often recognise the transplanted tissue as foreign and attempt to kill it, and also in bone marrow transplantation when there is a high risk of graft-versus-host disease where the transplanted cells attack their host cells, often causing death.

There thus remains a need in the art for the identification and isolation of genes encoding proteins expressed in cells of the immune system for use in the development of therapeutic agents for the treatment of disorders including those associated with the immune system.

SUMMARY OF THE INVENTION

The present invention provides polypeptides and functional portions of polypeptides expressed in lymph node stromal cells of fsn -/- mice, together with polynucleotides encoding such polypeptides, expression vectors and host cells comprising such polynucleotides, and methods for their use.

In specific embodiments, isolated polypeptides are provided that comprise an amino acid sequence selected from the group consisting of sequences provided in SEQ ID NO: 11–20, 30–38, 47–53 and 59–61, and variants of such sequences, as defined herein. Isolated polypeptides which comprise at least a functional portion of a polypeptide comprising an amino acid sequence selected from the group consisting of (a) sequences provided in SEQ ID NO: 11–20, 30–38, 47–53 and 59–61; and (b) variants of a sequence of SEQ ID NO: 11–20, 30–38, 47–53 and 59–61, as defined herein, are also provided.

In other embodiments, the present invention provides isolated polynucleotides comprising a nucleotide sequence selected from the group consisting of (a) sequences provided in SEQ ID NO: 1–10, 21–29, 39–46 and 58; (b) complements of sequences provided in SEQ ID NO: 1–10, 21–29, 39–46 and 58; (c) reverse complements of sequences provided in SEQ ID NO: 1–10, 21–29, 39–46 and 58; (d) reverse sequences of sequences provided in SEQ ID NO: 1–10, 21–29, 39–46 and 58; and (e) variants of the sequences of (a)–(d), as defined herein.

In related embodiments, the present invention provides expression vectors comprising the above polynucleotides, together with host cells transformed with such vectors.

As detailed below, the isolated polynucleotides and polypeptides of the present invention may be usefully employed in the preparation of therapeutic agents for the treatment of immunological disorders.

In related embodiments, methods for modulating the growth of blood vessels, and for the treatment of disorders such as inflammatory disorders, disorders of the immune system, cancer, tumour-necrosis factor-mediated disorders, and viral disorders are provided. Examples of such disorders include HIV-infection; epithelial, lymphoid, myeloid, stromal and neuronal cancers; arthritis; inflammatory bowel disease; and cardiac failure.

The above-mentioned and additional features of the present invention, together with the manner of obtaining them, will be best understood by reference to the following more detailed description. All references disclosed herein are hereby incorporated by reference in their entirety as if each was incorporated individually.

BRIEF DESCRIPTION OF THE DRAWINGS

FIG. 1 is the amino acid sequence of the murine FGF receptor muFGFβ (SEQ ID NO: 31), showing the location of the transmembrane domain, the Ig domain, splice sites, and putative glycosylation and SHP binding sites. Specifically, the underlined regions represent the signal peptide, IgG1 domain, IgG2 domain and transmembrane domain; the regions in bold italics and underlined represent the four putative glycosylation sites; and the bold underlined regions represent the two putative SHP-2 binding sites.

FIG. 2B shows the competition analysis of NIH-3T3 SRE cells treated with a standard dose of FGF-2+heparin in the presence of increasing concentrations of FGFR2Fc (closed diamonds), FGFR5βFc (closed squares), FGFR5γFc (closed triangles) and FGF-2 alone (asterisk). The mean and SD were calculated for both experiments from 3 separate wells and are represented as fold-induction of the reporter gene relative to.

FIG. 9 illustrates the stimulation of NK cell adherence by FGFR5β and FGFR5γ as measured by the presence of anti-CD56 antibodies, markers of NK cells. The filled histograms represent the adherent PBMC stained with the NK cell marker CD56 and the open histograms represent the same cells stained with the isotype-matched control antibody.

DETAILED DESCRIPTION OF THE INVENTION

Figure 2A:
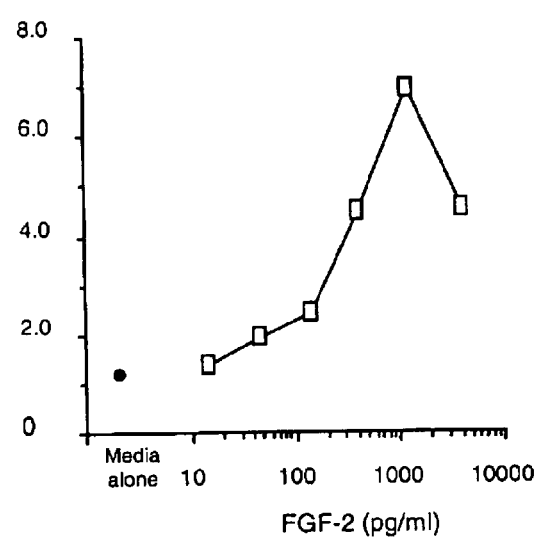
FIG. 2A shows the induction of genes under the control of the SRE. NIH-3T3 SRE cells were stimulated with a titration of FGF-2 in the presence of 10 µg/ml of heparin for 6 hours. Closed circles represent media alone, open squares represent titration of FGF-2.

In one aspect, the present invention provides polynucleotides isolated from lymph node stromal cells of fsn -/- mice and isolated polypeptides encoded by such polynucleotides.

The term "polynucleotide(s)," as used herein, means a single or double-stranded polymer of deoxyribonucleotide or ribonucleotide bases and includes DNA and corresponding RNA molecules, including HnRNA and mRNA molecules, both sense and anti-sense strands, and comprehends cDNA, genomic DNA and recombinant DNA, as well as wholly or partially synthesized polynucleotides. An HnRNA molecule contains introns and corresponds to a DNA molecule in a generally one-to-one manner. An mRNA molecule corresponds to an HnRNA and DNA molecule from which the introns have been excised. A polynucleotide may consist of an entire gene, or any portion thereof. Operable anti-sense polynucleotides may comprise a fragment of the corresponding polynucleotide, and the definition of "polynucleotide" therefore includes all such operable anti-sense polynucleotides. Anti-sense polynucleotides and techniques involving anti-sense polynucleotides are well known in the art and are described, for example, in Robinson-Benion et al., *Methods in Enzymol.* 254: 363–375, 1995 and Kawasaki et al., *Artific. Organs* 20: 836–848, 1996.

In specific embodiments, the isolated polynucleotides of the present invention comprise a polynucleotide sequence selected from the group consisting of sequences provided in SEQ ID NO: 1–10, 21–29, 39–46 and 58.

Complements of such isolated polynucleotides, reverse complements of such isolated polynucleotides and reverse sequences of such isolated polynucleotides are also provided, together with polynucleotides comprising at least a specified number of contiguous residues (x-mers) of any of the above-mentioned polynucleotides, extended sequences corresponding to any of the above polynucleotides, anti-sense sequences corresponding to any of the above polynucleotides, and variants of any of the above polynucleotides, as that term is described in this specification.

The definitions of the terms "complement", "reverse complement" and "reverse sequence", as used herein, are best illustrated by the following example. For the sequence 5' AGGACC 3', the complement, reverse complement and reverse sequence are as follows:

```
complement           3' TCCTGG 5' reverse complement   3' GGTCCT 5' reverse sequence     5' CCAGGA 3'.
```

Some of the polynucleotides of the present invention are "partial" sequences, in that they do not represent a full length gene encoding a full length polypeptide. Such partial sequences may be extended by analyzing and sequencing various DNA libraries using primers and/or probes and well known hybridization and/or PCR techniques. Partial sequences may be extended until an open reading frame encoding a polypeptide, a full length polynucleotide and/or gene capable of expressing a polypeptide, or another useful portion of the genome is identified. Such extended sequences, including full length polynucleotides and genes, are described as "corresponding to" a sequence identified as one of the sequences of SEQ ID NO: 1–10, 21–29, 39–46 and 58, or a variant thereof, or a portion of one of the sequences of SEQ ID NO: 1–10, 21–29, 39–46 and 58, or a variant thereof, when the extended polynucleotide comprises an identified sequence or its variant, or an identified contiguous portion (x-mer) of one of the sequences of SEQ ID NO: 1–10, 21–29, 39–46 and 58, or a variant thereof. Such extended polynucleotides may have a length of from about 50 to about 4,000 nucleic acids or base pairs, and preferably have a length of less than about 4,000 nucleic acids or base pairs, more preferably yet a length of less than about 3,000 nucleic acids or base pairs, more preferably yet a length of less than about 2,000 nucleic acids or base pairs. Under some circumstances, extended polynucleotides of the present invention may have a length of less than about 1,800 nucleic acids or base pairs, preferably less than about 1,600 nucleic acids or base pairs, more preferably less than about 1,400 nucleic acids or base pairs, more preferably yet less than about 1,200 nucleic acids or base pairs, and most preferably less than about 1,000 nucleic acids or base pairs.

Similarly, RNA sequences, reverse sequences, complementary sequences, antisense sequences, and the like, corresponding to the polynucleotides of the present invention, may be routinely ascertained and obtained using the cDNA sequences identified as SEQ ID NO: 1–10, 21–29, 39–46 and 58.

The polynucleotides identified as SEQ ID NO: 1–10, 21–29, 39–46 and 58 contain open reading frames ("ORFs") or partial open reading frames encoding polypeptides or functional portions of polypeptides. Open reading frames may be identified using techniques that are well known in the art. These techniques include, for example, analysis for the location of known start and stop codons, most likely reading frame identification based on codon frequencies, etc. Open reading frames and portions of open reading frames may be identified in the polynucleotides of the present invention. Suitable tools and software for ORF analysis are available, for example, on the Internet. Suitable tools and software for ORF analysis are also available through other distribution channels. Exemplary tools and software include, for example, GeneWise, available from The Sanger Center, Wellcome Trust Genome Campus, Hinxton, Cambridge, CB10 1SA, United Kingdom; Diogenes, available from Computational Biology Centers, University of Minnesota, Academic Health Center, UMHG Box 43 Minneapolis Minn. 55455; and GRAIL, available from the Informatics Group, Oak Ridge National Laboratories, Oak Ridge, Tennessee Tenn. Once a partial open reading frame is identified, the polynucleotide may be extended in the area of the partial open reading frame using techniques that are well known in the art until the polynucleotide for the full open reading frame is identified. Thus, open reading frames encoding polypeptides and/or functional portions of polypeptides may be identified using the polynucleotides of the present invention.

Once open reading frames are identified in the polynucleotides of the present invention, the open reading frames may be isolated and/or synthesized. Expressible genetic constructs comprising the open reading frames and suitable promoters, initiators, terminators, etc., which are well known in the art, may then be constructed. Such genetic constructs may be introduced into a host cell to express the polypeptide encoded by the open reading frame. Suitable host cells may include various prokaryotic and eukaryotic cells, including plant cells, mammalian cells, bacterial cells, algae and the like.

In another aspect, the present invention provides isolated polypeptides encoded, or partially encoded, by the above polynucleotides. The term "polypeptide", as used herein, encompasses amino acid chains of any length including full length proteins, wherein amino acid residues are linked by covalent peptide bonds. Polypeptides of the present invention may be naturally purified products, or may be produced partially or wholly using recombinant techniques. The term "polypeptide encoded by a polynucleotide" as used herein, includes polypeptides encoded by a nucleotide sequence which includes the partial isolated DNA sequences of the present invention. In specific embodiments, the inventive polypeptides comprise an amino acid sequence selected from the group consisting of sequences provided in SEQ ID NO: 11–20, 30–38, 47–53, 59 and variants of such sequences.

Polypeptides encoded by the polynucleotides of the present invention may be expressed and used in various assays to determine their biological activity. Such polypeptides may be used to raise antibodies, to isolate corresponding interacting proteins or other compounds, and to quantitatively determine levels of interacting proteins or other compounds.

All of the polynucleotides and polypeptides described herein are isolated and purified, as those terms are commonly used in the art. Preferably, the polypeptides and polynucleotides are at least about 80% pure, more preferably at least about 90% pure, and most preferably at least about 99% pure.

As used herein, the term "variant" comprehends nucleotide or amino acid sequences different from the specifically identified sequences, wherein one or more nucleotides or amino acid residues is deleted, substituted, or added. Variants may be naturally occurring allelic variants, or non-naturally occurring variants. Variant sequences (polynucleotide or polypeptide) preferably exhibit at least 50%, more preferably at least 75%, and most preferably at least 90% or 95% identity to a sequence of the present invention. The percentage identity is determined by aligning the two sequences to be compared, determining the number of identical residues in the aligned portion, dividing that number by the total length of the inventive, or queried, sequence and multiplying the result by 100.

Polynucleotide or polypeptide sequences may be aligned, and percentage of identical residues in a specified region may be determined against another polynucleotide, using computer algorithms that are publicly available. Two exemplary algorithms for aligning and identifying the similarity of polynucleotide sequences are the BLASTN and FASTA algorithms. Polynucleotides may also be analyzed using the BLASTX algorithm, which compares the six-frame conceptual translation products of a nucleotide query sequence (both strands) against a protein sequence database. The similarity of polypeptide sequences may be examined using the BLASTP or FASTX algorithms. Both the BLASTN and BLASTP software are available on the NCBI anonymous FTP server and are available from the National Center for Biotechnology Information (NCBI), National Library of Medicine, Building 38A, Room 8N805, Bethesda, Md. 20894 USA. The BLASTN algorithm versions 2.0.6 and version 2.0.11, set to the default parameters described in the documentation and distributed with the algorithm, are preferred for use in the determination of variants according to the present invention. The use of the BLAST family of algorithms, including BLASTN and BLASTP, is described at NCBI's website and in the publication of Altschul et al., "Gapped BLAST and PSI-BLAST: a new generation of protein database search programs", *Nucleic Acids Res.* 25:3389–3402, 1997.

The computer algorithm FASTA is available on the Internet. The FASTA software package is also available from the University of Virginia by contacting David Hudson, Assistant Provost for Research, University of Virginia, PO Box 9025, Charlottesville, Va. 22906-9025. FASTA Version3.1t11, August 1998, set to the default parameters described in the documentation and distributed with the algorithm, is preferred for use in the determination of variants according to the present invention. The use of the FASTA algorithm is described in Pearson and Lipman, "Improved Tools for Biological Sequence Analysis," *Proc. Natl. Acad. Sci. USA* 85:2444–2448, 1988 and Pearson, "Rapid and Sensitive Sequence Comparison with FASTP and FASTA," *Methods in Enzymol.* 183:63–98, 1990. The use of the FASTX algorithm is described in Pearson et al., "Comparison of DNA sequences with protein sequences," *Genomics* 46:24–36, 1997.

The following running parameters are preferred for determination of polynucleotide alignments and similarities using BLASTN that contribute to the E values and percentage identity: Unix running command: blastall -p blastn -d embldb -e 10 -G 0 -E 0 -r 1 -v 30 -b 30 -i queryseq -o results; and parameters are as follows: -p Program Name [String]; -d Database [String]; -e Expectation value (E) [Real]; -G Cost to open a gap (zero invokes default behavior) [Integer]; -E Cost to extend a gap (zero invokes default behavior) [Integer]; -r Reward for a nucleotide match (BLAST only) [Integer]; -v Number of one-line descriptions (V) [Integer]; -b Number of alignments to show (B) [Integer]; -i Query File [File In]; -o BLAST report Output File [File Out] Optional.

For BLASTP analyses of polypeptide sequences, the following running parameters are preferred: blastall -p blastp -d swissprotdb -e 10 -0 -E 0 -v 30 -b 30 -i queryseq -o results; and the parameters are as follows: -p Program Name [String]; -d Database [String]; -e Expectation value (E) [Real]; -G Cost to open a gap (zero invokes default behavior) [Integer]; -E Cost to extend a gap (zero invokes default behavior) [Integer]; -v Number of one-line descriptions (v) [Integer]; -b Number of alignments to show (b) [Integer]; -I Query File [File In]; -o BLAST report Output File [File Out] Optional.

The "hits" to one or more database sequences by a queried sequence produced by BLASTN, BLASTP, FASTA, or a similar algorithm, align and identify similar portions of sequences. The hits are arranged in order of the degree of similarity and the length of sequence overlap. Hits to a database sequence generally represent an overlap over only a fraction of the sequence length of the queried sequence.

The percentage identity of a polynucleotide or polypeptide sequence is determined by aligning polynucleotide and polypeptide sequences using appropriate algorithms, such as BLASTN or BLASTP, respectively, set to default parameters; identifying the number of identical nucleic or amino acids over the aligned portions; dividing the number of identical nucleic or amino acids by the total number of nucleic or amino acids of the polynucleotide or polypeptide of the present invention; and then multiplying by 100 to determine the percentage similarity. By way of example, a queried polynucleotide having 220 nucleic acids has a hit to a polynucleotide sequence in the EMBL database having 520 nucleic acids over a stretch of 23 nucleotides in the alignment produced by the BLASTN algorithm using the default parameters. The 23 nucleotide hit includes 21 identical nucleotides, one gap and one different nucleotide. The percentage identity of the queried polynucleotide to the hit in the EMBL database is thus 21/220 times 100, or 9.5%. The similarity of polypeptide sequences may be determined in a similar fashion.

The BLASTN and FASTA algorithms also produce "Expect" values for alignments. The Expect value (E) indicates the number of hits one can "expect" to see over a certain number of contiguous sequences by chance when searching a database of a certain size. The Expect value is used as a significance threshold for determining whether the hit to a database, such as the preferred EMBL database, indicates true similarity. For example, an E value of 0.1 assigned to a hit is interpreted as meaning that in a database of the size of the EMBL database, one might expect to see 0.1 matches over the aligned portion of the sequence with a similar score simply by chance. By this criterion, the aligned and matched portions of the sequences then have a probability of 90% of being the same. For sequences having an E value of 0.01 or less over aligned and matched portions, the probability of finding a match by chance in the EMBL database is 1% or less using the BLASTN or FASTA algorithm.

According to one embodiment, "variant" polynucleotides, with reference to each of the polynucleotides of the present invention, preferably comprise sequences having the same number or fewer nucleic acids than each of the polynucleotides of the present invention and producing an E value of 0.01 or less when compared to the polynucleotide of the present invention. That is, a variant polynucleotide is any sequence that has at least a 99% probability of being the same as the polynucleotide of the present invention, measured as having an E value of 0.01 or less using the BLASTN or FASTA algorithms set at the default parameters. According to a preferred embodiment, a variant polynucleotide is a sequence having the same number or fewer nucleic acids than a polynucleotide of the present invention that has at least a 99% probability of being the same as the polynucleotide of the present invention, measured as having an E value of 0.01 or less using the BLASTN or FASTA algorithms set at the default parameters.

Alternatively, variant polynucleotide sequences hybridize to the recited polynucleotide sequence under stringent conditions. As used herein, "stringent conditions" refers to prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

The present invention also encompasses polynucleotides that differ from the disclosed sequences but that, as a consequence of the degeneracy of the genetic code, encode a polypeptide which is the same as that encoded by a polynucleotide of the present invention. Thus, polynucleotides comprising sequences that differ from the polynucleotide sequences provided in SEQ ID NO: 1–10, 21–29, 39–46 and 58, or complements, reverse sequences, or reverse complements thereof, as a result of conservative substitutions, are contemplated by and encompassed within the present invention. Additionally, polynucleotides comprising sequences that differ from the polynucleotide sequences provided in SEQ ID NO: 1–10, 21–29, 39–46 and 58, or complements, reverse complements or reverse sequences thereof, as a result of deletions and/or insertions totaling less than 10% of the total sequence length are also contemplated by and encompassed within the present invention. Similarly, polypeptides comprising sequences that differ from the polypeptide sequences provided in SEQ ID NO: 11–20, 30–38, 47–53 and 59–61, as a result of amino acid substitutions, insertions, and/or deletions totaling less than 10% of the total sequence length are contemplated by and encompassed within the present invention.

Polynucleotides of the present invention also comprehend polynucleotides comprising at least a specified number of contiguous residues (x-mers) of any of the polynucleotides identified as SEQ ID NO: 1–10, 21–29, 39–46 and 58, complements, reverse sequences, and reverse complements of such sequences, and their variants. Similarly, polypeptides of the present invention comprehend polypeptides comprising at least a specified number of contiguous residues (x-mers) of any of the polypeptides identified as SEQ ID NO: 11–20, 30–38, 47–53 and 59–61, and their variants. As used herein, the term "x-mer," with reference to a specific value of "x," refers to a sequence comprising at least a specified number ("x") of contiguous residues of any of the polynucleotides identified as SEQ ID NO: 1–10, 21–29, 39–46 and 58, or the polypeptides identified as SEQ ID NO: 11–20, 30–38, 47–53 and 59–61. According to preferred embodiments, the value of x is preferably at least 20, more preferably at least 40, more preferably yet at least 60, and most preferably at least 80. Thus, polynucleotides and polypeptides of the present invention comprise a 20-mer, a 40-mer, a 60-mer, an 80-mer, a 100-mer, a 120-mer, a 150-mer, a 180-mer, a 220-mer, a 250-mer, a 300-mer, a 400-mer, a 500-mer or 600-mer of a polynucleotide or polypeptide identified as SEQ ID NO: 1–53, 58 and 59, and variants thereof.

The inventive polynucleotides may be isolated by high throughput sequencing of cDNA libraries prepared from lymph node stromal cells of fsn -/- mice as described below in Example 1. Alternatively, oligonucleotide probes based on the sequences provided in SEQ ID NO: 1–10, 21–29, 39–46 and 58 can be synthesized and used to identify positive clones in either cDNA or genomic DNA libraries from lymph node stromal cells of fsn -/- mice by means of hybridization or polymerase chain reaction (PCR) techniques. Probes can be shorter than the sequences provided herein but should be at least about 10, preferably at least about 15 and most preferably at least about 20 nucleotides in length. Hybridization and PCR techniques suitable for use with such oligonucleotide probes are well known in the art (see, for example, Mullis et al., *Cold Spring Harbor Symp. Quant. Biol.*, 51:263, 1987; Erlich ed., *PCR Technology*, Stockton Press, New York, 1989; Sambrook et al., *Molecular cloning—a laboratory manual*, Cold Spring Harbor Laboratory Press, Cold Spring Harbor, N.Y., 1989). Positive clones may be analyzed by restriction enzyme digestion, DNA sequencing or the like.

The polynucleotides of the present invention may alternatively be synthesized using techniques that are well known in the art. The polynucleotides may be synthesized, for example, using automated oligonucleotide synthesizers (e.g., Beckman Oligo 1000M DNA Synthesizer) to obtain polynucleotide segments of up to 50 or more nucleic acids. A plurality of such polynucleotide segments may then be ligated using standard DNA manipulation techniques that are well known in the art of molecular biology. One conventional and exemplary polynucleotide synthesis technique involves synthesis of a single stranded polynucleotide segment having, for example, 80 nucleic acids, and hybridizing that segment to a synthesized complementary 85 nucleic acid segment to produce a 5 nucleotide overhang. The next segment may then be synthesized in a similar fashion, with a 5 nucleotide overhang on the opposite strand. The "sticky" ends ensure proper ligation when the two portions are hybridized. In this way, a complete polynucleotide of the present invention may be synthesized entirely in vitro.

Polypeptides of the present invention may be produced recombinantly by inserting a DNA sequence that encodes the polypeptide into an expression vector and expressing the polypeptide in an appropriate host. Any of a variety of expression vectors known to those of ordinary skill in the art may be employed. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli*, insect, yeast or a mammalian cell line such as COS or CHO. The DNA sequences expressed in this manner may encode naturally occurring polypeptides, portions of naturally occurring polypeptides, or other variants thereof.

In a related aspect, polypeptides are provided that comprise at least a functional portion of a polypeptide having an amino acid sequence selected from the group consisting of sequences provided in SEQ ID NO: 11–20, 30–38, 47–53 and 59–61 and variants thereof. As used herein, the "functional portion" of a polypeptide is that portion which contains the active site essential for affecting the function of the polypeptide, for example, the portion of the molecule that is capable of binding one or more reactants. The active site may be made up of separate portions present on one or more polypeptide chains and will generally exhibit high binding affinity. Such functional portions generally comprise at least about 5 amino acid residues, more preferably at least about 10, and most preferably at least about 20 amino acid residues. Functional portions of the inventive polypeptides may be identified by first preparing fragments of the polypeptide, by either chemical or enzymatic digestion of the polypeptide or mutation analysis of the polynucleotide that encodes for the polypeptide, and subsequently expressing the resultant mutant polypeptides. The polypeptide fragments or mutant polypeptides are then tested to determine which portions retain the biological activity of the full-length polypeptide. Portions and other variants of the inventive polypeptides may be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain (Merrifield, *J. Am. Chem. Soc.* 85:2149–2154, 1963). Equipment for automated synthesis of polypeptides is commercially available from suppliers such as Perkin Elmer/Applied BioSystems, Inc. (Foster City, Calif.), and may be operated according to the manufacturer's instructions. Variants of a native polypeptide may be prepared using standard mutagenesis techniques, such as oligonucleotide-directed site-specific mutagenesis (see, for example, Kunkel, *Proc. Natl. Acad. Sci. USA* 82:488–492, 1985). Sections of DNA sequence may also be removed using standard techniques to permit preparation of truncated polypeptides.

The polynucleotide sequences of the present invention, derived from fsn -/- mouse lymph node stromal cells, encode polypeptides that have important role(s) in growth and development of the immune system, and in responses of the immune system to tissue injury and inflammation as well as other disease states. Some of the polynucleotides contain sequences that code for signal sequences, or transmembrane domains, which identify the protein products as secreted molecules or receptors. Such polypeptide products include growth factors, cytokines, or their cognate receptors. The polypeptide sequence of SEQ ID NO: 13 has more than 25% identity to members of the tumour necrosis factor (TNF) receptor family of proteins; the polypeptides of SEQ ID NO: 30, 31, 32 and 33 have more than 25% identity to members of the fibroblast growth factor (FGF) receptor family of proteins; and the polypeptide of SEQ ID NO: 38 has more than 25% identity to members of the WDNM1 family of proteins. These identified polypeptides have similar biological functions.

In particular, the inventive polypeptides have important roles in processes such as: modulation of immune responses; differentiation of precursor immune cells into specialized cell types; cell migration; cell proliferation and cell-cell interaction. The polypeptides are important in the defence of the body against infectious agents, and thus important in maintaining a disease-free environment. These polypeptides act as modulators of skin cells, especially since immune cells infiltrate skin during tissue insult, causing growth and differentiation of skin cells. In addition, these polypeptides are immunologically active, making them important therapeutic targets in a large range of disease states.

In one aspect, the present invention provides methods for using one or more of the inventive polypeptides or polynucleotides to treat disorders in a patient. As used herein, a "patient" refers to any warm-blooded animal, preferably a human.

In this aspect, the polypeptide or polynucleotide is generally present within a pharmaceutical composition or a vaccine. Pharmaceutical compositions may comprise one or more polypeptides, each of which may contain one or more of the above sequences (or variants thereof), and a physiologically acceptable carrier. Vaccines may comprise one or more of the above polypeptides and a non-specific immune response amplifier, such as an adjuvant or a liposome, into which the polypeptide is incorporated.

Alternatively, a vaccine or pharmaceutical composition of the present invention may contain DNA encoding one or more polypeptides as described above, such that the polypeptide is generated in situ. In such vaccines and pharmaceutical compositions, the DNA may be present within any of a variety of delivery systems known to those of ordinary skill in the art, including nucleic acid expression systems, and bacterial and viral expression systems. Appropriate nucleic acid expression systems contain the necessary DNA sequences for expression in the patient (such as a suitable promoter and terminator signal). Bacterial delivery systems involve the administration of a bacterium (such as Bacillus Calmette-Guerin) that expresses an immunogenic portion of the polypeptide on its cell surface. In a preferred embodiment, the DNA may be introduced using a viral expression system (e.g., vaccinia or other poxvirus, retrovirus, or adenovirus), which may involve the use of a non-pathogenic, or defective, replication competent virus. Techniques for incorporating DNA into such expression systems are well known in the art. The DNA may also be "naked," as described, for example, in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells.

Routes and frequency of administration, as well as dosage, vary from individual to individual. In general, the pharmaceutical compositions and vaccines may be administered by injection (e.g., intradermal, intramuscular, intravenous or subcutaneous), intranasally (e.g., by aspiration) or orally. In general, the amount of polypeptide present in a dose (or produced in situ by the DNA in a dose) ranges from about 1 pg to about 100 mg per kg of host, typically from about 10 pg to about 1 mg per kg of host, and preferably from about 100 pg to about 1 μg per kg of host. Suitable dose sizes will vary with the size of the patient, but will typically range from about 0.1 ml to about 2 ml.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a lipid, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897, 268 and 5,075,109.

Any of a variety of adjuvants may be employed in the vaccines derived from this invention to non-specifically enhance the immune response. Most adjuvants contain a substance designed to protect the antigen from rapid catabolism, such as aluminum hydroxide or mineral oil, and a non-specific stimulator of immune responses, such as lipid A, *Bordetella pertussis* or *M. tuberculosis*. Suitable adjuvants are commercially available as, for example, Freund's Incomplete Adjuvant and Freund's Complete Adjuvant (Difco Laboratories, Detroit, Mich.), and Merck Adjuvant 65 (Merck and Company, Inc., Rahway, N.J.). Other suitable adjuvants include alum, biodegradable microspheres, monophosphoryl lipid A and Quil A.

The polynucleotides of the present invention may also be used as markers for tissue, as chromosome markers or tags, in the identification of genetic disorders, and for the design of oligonucleotides for examination of expression patterns using techniques well known in the art, such as the microarray technology available from Synteni (Palo Alto, Calif.). Partial polynucleotide sequences disclosed herein may be employed to obtain full length genes by, for example, screening of DNA expression libraries, and to isolate homologous DNA sequences from other species using hybridization probes or PCR primers based on the inventive sequences.

The isolated polynucleotides of the present invention also have utility in genome mapping, in physical mapping, and in positional cloning of genes. As detailed below, the polynucleotide sequences identified as SEQ ID NO: 1–10, 21–29, 39–46 and 58, and their variants, may be used to design oligonucleotide probes and primers. Oligonucleotide probes designed using the polynucleotides of the present invention may be used to detect the presence and examine the expression patterns of genes in any organism having sufficiently similar DNA and RNA sequences in their cells using techniques that are well known in the art, such as slot blot DNA hybridization techniques. Oligonucleotide primers designed using the polynucleotides of the present invention may be used for PCR amplifications. Oligonucleotide probes and primers designed using the polynucleotides of the present invention may also be used in connection with various microarray technologies, including the microarray technology of Synteni (Palo Alto, Calif.).

As used herein, the term "oligonucleotide" refers to a relatively short segment of a polynucleotide sequence, generally comprising between 6 and 60 nucleotides, and comprehends both probes for use in hybridization assays and primers for use in the amplification of DNA by polymerase chain reaction. An oligonucleotide probe or primer is described as "corresponding to" a polynucleotide of the present invention, including one of the sequences set out as SEQ ID NO: 1–10, 21–29 and 39–46, or a variant thereof, if the oligonucleotide probe or primer, or its complement, is contained within one of the sequences set out as SEQ ID NO: 1–10, 21–29, 39–46 and 58, or a variant of one of the specified sequences. Oligonucleotide probes and primers of the present invention are substantially complementary to a polynucleotide disclosed herein.

Two single stranded sequences are said to be substantially complementary when the nucleotides of one strand, optimally aligned and compared, with the appropriate nucleotide insertions and/or deletions, pair with at least 80%, preferably at least 90% to 95% and more preferably at least 98% to 100% of the nucleotides of the other strand. Alternatively, substantial complementarity exists when a first DNA strand will selectively hybridize to a second DNA strand under stringent hybridization conditions. Stringent hybridization conditions for determining complementarity include salt conditions of less than about 1 M, more usually less than about 500 mM, and preferably less than about 200 mM. Hybridization temperatures can be as low as 5° C., but are generally greater than about 22° C., more preferably greater than about 30° C., and most preferably greater than about 37° C. Longer DNA fragments may require higher hybridization temperatures for specific hybridization. Since the stringency of hybridization may be affected by other factors such as probe composition, presence of organic solvents and extent of base mismatching, the combination of parameters is more important than the absolute measure of any one alone.

In specific embodiments, the oligonucleotide probes and/or primers comprise at least about 6 contiguous residues, more preferably at least about 10 contiguous residues, and most preferably at least about 20 contiguous residues complementary to a polynucleotide sequence of the present invention. Probes and primers of the present invention may be from about 8 to 100 base pairs in length or, preferably from about 10 to 50 base pairs in length or, more preferably from about 15 to 40 base pairs in length. The probes can be easily selected using procedures well known in the art, taking into account DNA—DNA hybridization stringencies, annealing and melting temperatures, and potential for formation of loops and other factors, which are well known in the art. Tools and software suitable for designing probes, and especially suitable for designing PCR primers, are available on the Internet, for example. A software program suitable for designing probes, and especially for designing PCR primers, is available from Premier Biosoft International, 3786 Corina Way, Palo Alto, Calif. 94303-4504. Preferred techniques for designing PCR primers are also disclosed in Dieffenbach, CW and Dyksler, GS. *PCR Primer: a laboratory manual*, CSHL Press: Cold Spring Harbor, N.Y., 1995.

A plurality of oligonucleotide probes or primers corresponding to a polynucleotide of the present invention may be provided in a kit form. Such kits generally comprise multiple DNA or oligonucleotide probes, each probe being specific for a polynucleotide sequence. Kits of the present invention may comprise one or more probes or primers corresponding to a polynucleotide of the present invention, including a polynucleotide sequence identified in SEQ ID NO: 1–10, 21–29, 39–46 and 58.

In one embodiment useful for high-throughput assays, the oligonucleotide probe kits of the present invention comprise multiple probes in an array format, wherein each probe is immobilized at a predefined, spatially addressable location on the surface of a solid substrate. Array formats which may be usefully employed in the present invention are disclosed, for example, in U.S. Pat. Nos. 5,412,087 and 5,545,451, and PCT Publication No. WO 95/00450, the disclosures of which are hereby incorporated by reference.

The polynucleotides of the present invention may also be used to tag or identify an organism or reproductive material therefrom. Such tagging may be accomplished, for example, by stably introducing a non-disruptive non-functional heterologous polynucleotide identifier into an organism, the polynucleotide comprising one of the polynucleotides of the present invention.

The polypeptides provided by the present invention may additionally be used in assays to determine biological activity, to raise antibodies, to isolate corresponding ligands or receptors, in assays to quantify levels of protein or cognate corresponding ligand or receptor, as anti-inflammatory agents, and in compositions for the treatment of diseases of skin, connective tissue and the immune system.

EXAMPLE 1

Isolation of cDNA Sequences From Lymph Node Stromal Cell Expression Libraries The cDNA sequences of the present invention were obtained by high-throughput sequencing of cDNA expression libraries constructed from rodent fsn -/- lymph node stromal cells as described below.

cDNA Libraries from Lymph Node Stromal Cells (MLSA and MLSE)

Lymph nodes were removed from flaky skin fsn -/- mice, the cells dissociated and the resulting single cell suspension placed in culture. After four passages, the cells were harvested. Total RNA, isolated using TRIzol Reagent (BRL Life Technologies, Gaithersburg, Md.), was used to obtain mRNA using a Poly(A) Quik mRNA isolation kit (Stratagene, La Jolla, Calif.), according to the manufacturer's specifications. A cDNA expression library (referred to as the MLSA library) was then prepared from the mRNA by Reverse Transcriptase synthesis using a Lambda ZAP Express cDNA library synthesis kit (Stratagene, La Jolla, Calif.). A second cDNA expression library, referred to as the MLSE library, was prepared exactly as above except that the cDNA was inserted into the mammalian expression vector pcDNA3 (Invitrogen, Carlsbad Calif.).

The nucleotide sequence of the cDNA clone isolated from the MLSE library is given in SEQ ID NO: 1, with the corresponding amino acid sequence being provided in SEQ ID NO: 11. The nucleotide sequences of the cDNA clones isolated from the MLSA library are given in SEQ ID NO: 2–10, 21–23 and 28, with the corresponding amino acid sequences being provided in SEQ ID NO: 12–20, 30–32 and 37, respectively.

Subtracted cDNA Library from flaky skin Lymph Node Stromal Cells (MLSS)

Stromal cells from flaky skin mice lymph nodes and 3T3 fibroblasts were grown in culture and the total RNA extracted from these cells using established protocols. Total RNA from both populations was isolated using TRIzol Reagent (Gibco BRL Life Technologies, Gaitherburg, Md.) and used to obtain mRNA using either a Poly (A) Quik mRNA isolation kit (Stratagene, La Jolla, Calif.) or Quick Prep$^{(R)}$ Micro mRNA purification kit (Pharmacia, Uppsala, Sweden). Double-stranded cDNA from flaky skin lymph node stromal cell mRNA was prepared by Reverse Transcriptase synthesis using a lambda ZAP cDNA library synthesis kit (Stratagene) that had been ligated with EcoRI adaptors and digested with XhoI to produce double-stranded fragments with EcoRI and IhoI overhanging ends.

Double-stranded cDNA from 3T3 fibroblasts was prepared using the Superscript II reverse transcriptase (Gibco BRL Life Technologies) followed by treatment with DNA polymerase I and RNaseH (Gibco BRL Life Technologies). Double-stranded 3T3 cDNA was then digested with restriction endonucleases AluI and RsaI (Gibco BRL Life Technologies) to produce blunt-ended fragments. A 20-fold excess of AluI/RsaI-digested 3T3 cDNA was hybridized with the EcoRI/IhoI flaky skin lymph node stromal cell cDNA in the following hybridisation solution: 50% formamide, 5×SSC, 10 mM NaH$_2$PO$_4$ pH7.5, 1 mM EDTA, 0.1% SDS, 200 μg yeast tRNA (Boehringer Mannheim) at 37° C. for 24 hours. Hybridized flaky skin lymph node stromal cell cDNA and 3T3 cDNA was then phenol/chloroform extracted and ethanol precipitated. The cDNA was size-fractionated over a Sepharose CL-2B gel filtration column as described in the Lambda ZAP cDNA library synthesis protocol (Stratagene). Flaky skin lymph node stromal cell-specific cDNA was preferentially ligated into ZAP Express vector (Stratagene) by virtue of EcoRI/XhoI ends. Chimeric cDNA between flaky skin lymph node stromal cell cDNA and 3T3 cDNA would not be cloned due to non-compatible ends, and the subtracted cDNA library was packaged using Gigapack III Gold packaging extract (Stratagene).

The nucleotide sequences of the cDNA clones isolated from the MLSS library are given in SEQ ID NO: 25–27 and 29, with the corresponding amino acid sequences being provided in SEQ ID NO: 34–36 and 38, respectively.

EXAMPLE 2

Characterization of Isolated cDNA Sequences

The isolated cDNA sequences were compared to sequences in the EMBL DNA database using the computer algorithm BLASTN, and the corresponding polypeptide sequences (DNA translated to protein in each of 6 reading frames) were compared to sequences in the SwissProt database using the computer algorithm BLASTP. Specifically, comparisons of DNA sequences provided in SEQ ID NO: 1–10, 21–29 and 39–46 to sequences in the EMBL (Release 60, September 1999) DNA database, and amino acid sequences provided in SEQ ID NO: 11–20, 30–38 and 47–53 to sequences in the SwissProt and TrEMBL (up to October 20, 1999) databases were made as of Dec. 31, 1999. Comparisons of DNA sequences provided in SEQ ID NO: 58 to sequences in the EMBL (Release 62, April 2000) DNA database, and amino acid sequences provided in SEQ ID NO: 59 to sequences in the SwissProt and TrEMBL (up to Apr. 7, 2000) databases were made as of Jul. 11, 2000. The cDNA sequences of SEQ ID NO: 1–10, 21–24 and 27–28, and their corresponding polypeptide sequences (SEQ ID NO: 11–20, 30–33 and 36–37, respectively) were determined to have less than 75% identity (determined as described above) to sequences in the EMBL and SwissProt databases using the computer algorithms BLASTN and BLASTP, respectively. The polypeptide of SEQ ID NO: 59 was determined to have less than 75% identity (determined as described above) to sequences in the SwissProt database using the computer algorithm BLASTP.

Isolated cDNA sequences and their corresponding polypeptide sequences, were computer analyzed for the presence of signal sequences identifying secreted molecules. Isolated cDNA sequences that have a signal sequence at a putative start site within the sequence are provided in SEQ ID NO: 4–6, 9–10, 25–26, 39–41 and 43–45. The isolated cDNA sequences were also computer analyzed for the presence of transmembrane domains coding for putative membrane-bound molecules. Isolated cDNA sequences that have one or more transmembrane domain(s) within the sequence are provided in SEQ ID NO: 1–3, 7, 8, 27 and 41–45.

Using automated search programs to screen against sequences coding for known molecules reported to be of therapeutic and/or diagnostic use, the isolated polynucleotides of SEQ ID NO: 3, 21–24 and 29 were determined to encode polypeptide sequences that are members of the tumour necrosis factor (TNF) receptor family of proteins (SEQ ID NO: 13), the fibroblast growth factor (FGF) receptor family (SEQ ID NO: 30–33), the WDNM1 protein family (SEQ ID NO: 38) and the serine/threonine protein kinase family (SEQ ID NO: 59). A family member is here defined to have at least 20% identical amino acid residues in the translated polypeptide to a known protein or member of a protein family.

As noted above, the isolated cDNA sequence of SEQ ID NO: 3 was determined to encode a polypeptide (SEQ ID NO: 13) that is a member of the TNF-receptor family. Proteins of the TNF/NGF-receptor family are involved in the proliferation, differentiation and death of many cell types including B and T lymphocytes. Residues 18–55 of SEQ ID NO: 13 show a high degree of similarity to the Prosite motif for the TNF/NGF receptor family (Banner et al., *Cell* 73:431–445, 1993). This motif contributes to the ligand binding domain of the molecule and is thus essential to its function. (Gruss and Dower, *Blood* 85:3378–3404, 1995). The polypeptide of SEQ ID NO: 13 therefore influences the growth, differentiation and activation of several cell types, and has utility as an agent for the treatment of skin wounds, and the treatment and diagnosis of cancers, inflammatory diseases, and growth and developmental defects.

The isolated cDNA sequence of SEQ ID NO: 29 was determined to encode a polypeptide (SEQ ID NO: 38) that is a member of the WDNM1 protein family. The WDNM1 family of proteins has a conserved arrangement of cysteine residues. The family includes several proteinase inhibitors, indicating that WDNM1 encodes a product with proteinase inhibiting capacity. The WDNM1 gene has been shown to be down-regulated in metastatic rat mammary adenocarcinomas (Dear and Kefford, *Biochem. Biophys. Res. Comm.* 176:247–254,1991).

The isolated cDNA sequence of SEQ ID NO: 21 was determined to encode a protein sequence (SEQ ID NO: 30) that is a member of the fibroblast growth factor (FGF) receptor family of proteins, specifically the FGF receptor 3. Fibroblast growth factor receptors belong to a family of four single membrane-spanning tyrosine kinases (FGFR1 to 4). These receptors serve as high-affinity receptors for 17 growth factors (FGF1 to 17). FGF receptors have important roles in multiple biological processes, including mesoderm induction and patterning, cell growth and migration, organ formation and bone growth (Xu, *Cell Tissue Res.* 296:33–43, 1999). Further analysis of the sequence revealed the presence of a putative transmembrane domain and intracellular domain, similar to other FGF receptors.

The isolated cDNA sequence of SEQ ID NO: 44 was determined to encode a polypeptide (SEQ ID NO: 52) corresponding to a lysyl oxidase-related protein. Lysyl oxidase is a copper-dependent amine oxidase that has an important role in the formation of connective tissue matrices. The molecule is involved in crosslinking of the extracellular matrix proteins, collagen and elastin (Smith-Mungo and Kagan, *Matrix Biol.* 16:387–398, 1998). Expression of lysyl oxidase is upregulated in many fibrotic diseases, and down regulated in diseases involving impaired copper metabolism. Identification of new lysyl oxidase-related proteins indicates the existence of a multigene family. Experimental evidence suggests that lysyl oxidase may have other important biological functions in addition to its role in cross-linking of collagen and elastin (Smith-Mungo and Kagan, *Matrix Biol.* 16:387–398, 1998).

The isolated cDNA sequence of SEQ ID NO: 45 was determined to encode a polypeptide (SEQ ID NO: 53) of a CD99-like protein. CD99, also referred to as MIC2, is a cell surface molecule involved in T cell adhesion processes (Gelin et al., *EMBO J.* 8:3252–3259).

The isolated cDNA sequence of SEQ ID NO: 58 was determined to encode a polypeptide sequence (SEQ ID NO: 59) that corresponds to a serine/threonine protein kinase. Serine/threonine kinases participate in cell cycle progression and signal transduction. They are involved in mediating intracellular responses to external signals, such as growth factors, hormones and neurotransmitters, and are involved in cell proliferation and oncogenesis.

EXAMPLE 3

Isolation of Full Length cDNA Sequence of a Murine Fibroblast Growth Factor Receptor Homolog The full-length cDNA sequence of a murine fibroblast growth factor receptor homolog was isolated as follows.

The MLSA cell cDNA library (described in Example 1) was screened with an [$\alpha^{32}$P]-dCTP labeled cDNA probe corresponding to nucleotides 1 to 451 of the coding region within SEQ ID NO: 21. Plaque lifts, hybridization and screening were performed using standard molecular biology techniques. The determined polynucleotide sequence of the full-length murine FGFR gene (referred to as muFGFR-β) is provided in SEQ ID NO: 22, with the corresponding polypeptide sequence being provided in SEQ ID NO: 31.

Analysis of the polynucleotide sequence of SEQ ID NO: 22 revealed the presence of a putative transmembrane domain corresponding to nucleotides 1311 to 1370. The polypeptide sequence (SEQ ID NO: 31; FIG. 1) has regions similar to the extracellular domain of the fibroblast growth factor receptor family. The amino acid sequence of the extracellular domain of muFGFR-β is provided in SEQ ID NO: 60, while the amino acid sequence of the intracellular domain is provided in SEQ ID NO: 61.

A splice variant of SEQ ID NO: 22 was also isolated from the MLSA cDNA library as described in Example 1. The determined polynucleotide sequence of the splice variant (referred to as FGFR-γ) is provided in SEQ ID NO: 23 and the corresponding polypeptide sequence is provided in SEQ ID NO: 32. The splice regions are in an equivalent position to splice sites for previously described FGF receptors (Omitz, *J. Biol. Chem.* 296:15292–15297, 1996; Wilkie, *Current Biology* 5:500–507, 1995; Miki, *Proc. Natl. Acad. Sci. USA* 89:246–250, 1992), thus establishing that this molecule (referred to as FGFR5) is a FGF receptor homolog. The main difference between the two FGFR5 splice variants is that muFGFR-β contains three extracellular Ig-domains, while FGFR-γ contains only two such domains.

To examine the structural similarities between FGFR5 and the other members of the FGF receptor family, 3D Swiss modeller (Petisch, *Bio/Technology* 13:658–660, 1995; Peitsch, *Biochem Soc Trans.* 24:274–279, 1996; Guex and Peitsch, *Electrophoresis* 18:2714–2723, 1997) was employed to produce a predicted crystal structure of the extracellular domain of FGFR-γ. These studies showed that the crystal structure of FGFR5 deviates from that of the known FGFR1 structure between residues 188 and 219 of SEQ ID NO: 32. These residues correlate with an area of low homology between FGFR5 and other members of the FGF receptor family that may have a critical role in defining ligand specificity.

The critical residues for ligand binding have previously been identified in co-crystallization studies of FGFR1 binding FGF-2 (Plotnikov et al., *Cell* 98:641–650, 1999). Alignment of FGFR-γ with FGFR1 showed that many of these residues are conserved or are a conservative substitution. Conserved ligand binding residues between the two receptors are found at residues 66, 68, 146, 178, 181, 183 and 216 of SEQ ID NO: 32, while conservative substitutions of potential ligand binding residues are found at residues 64, 180 and 226 of SEQ ID NO: 32. When visualized on the predicted crystal structure of FGFR-γ, these residues line the groove of the ligand binding domain. Thus, while the overall degree of similarity between FGFR5 and other FGF receptors is relatively low, the extracellular domains of the two FGFR5 splice variants have all the conserved residues important for ligand binding.

The main difference between the FGFR5 receptor and other family members is the lack of an intracellular tyrosine kinase domain. With the four previously identified FGF receptors (FGFR1–4), signal transduction is mediated by ligand binding and receptor dimerization, resulting in autophosphorylation of the tyrosine residues within the intracellular RTK domain. This autophosphorylation then phosphorylates a number of intracellular substrates, initiating several signal transduction cascades. The FGFR5 splice variants described herein each contain tyrosine residues in the intracellular domain demonstrating similarity to a SHP binding motif (residues 458–463 of SEQ ID NO: 31 and 367–377 of SEQ ID NO: 32). SHPs are protein tyrosine phosphatases that participate in cellular signalling and that have previously been identified in the cytoplasmic domains of many receptors eliciting a broad range of activities. The presence of such motifs in the cytoplasmic domain of FGFR5 is thus indicative of signalling, and modification of these motifs may be employed to modulate signal transduction initiated by binding of a ligand to FGFR5. These motifs are conserved between the mouse transcripts of FGFR5 and the human homolog described below.

EXAMPLE 4

Isolation of a Human FGF Receptor Homolog

The cDNA EST encoding the partial murine FGF receptor (SEQ ID NO: 21) was used to search the EMBL database (Release 58, March 1999) to identify human EST homologs. The identified EST (Accession Number AI245701) was obtained from Research Genetics, Inc (Huntsville Ala.) as I.M.A.G.E. Consortium clone ID 1870593. Sequence determination of the complete insert of clone 1870593 resulted in the identification of 520 additional nucleotides. The insert of this clone did not represent the full-length gene. The determined nucleotide sequence of the complete insert of clone 1870593 is given in SEQ ID NO: 24 and the corresponding polypeptide sequence in SEQ ID NO: 33.

EXAMPLE 5

Characterization of Murine FGF Receptor Homolog

Soluble forms of the murine FGF receptor homolog, muFGFR-β and splice variant FGFR-γ (SEQ ID NO: 22 and 23, respectively) were expressed in mammalian cells and the purified proteins used to determine the ligand binding specificity of the molecules as follows.

The extracellular domains of muFGFR-β and FGFR-γ were amplified by PCR using primers MS158 and MS 159 (SEQ ID NO: 55 and 56, respectively) and cloned into the expression vector pcDNA3 containing the Fc fragment from human IgG1. These soluble recombinant proteins, referred to as FGFRβFc and FGFRγFc, were expressed in HEK293 cells (ATCC No. CRL-1573, American Type Culture Collection, Manassas, Va.) and purified using an Affiprep protein A column (Biorad, Hercules Calif.).

FGF-2 (basic fibroblast growth factor) has previously been demonstrated to bind all FGF receptors but with a range of different affinities. Binding of muFGFR-β to FGF-2 was demonstrated by co-incubating the purified protein and FFGF-2 in the presence of protein G Sepharose (Amersham Pharmacia, Uppsala, Sweden) and resolving complexes formed on denaturing polyacrylamide gels. FGF-2 (2 μg) was incubated with 5 μg FGFRβPFc, FGF Receptor 2 (FGFR2Fc) or unrelated protein (MLSA8790Fc) in 5 μl protein G fast flow beads (Pharmacia, Uppsala, Sweden), PBS and 0.1% Triton X-100 for 60 min at 4° C. The beads were washed three times in 0.1% TritonX-100/PBS and resuspended in 20 μl loading buffer (0.1 M DTT, 10% sucrose, 60 mM Tris.HCl pH 6.8, 5% SDS and 0.01% bromophenol blue). The samples were analysed on a 12% polyacrylamide gel. FGF-2, FGFR2Fc, FGFRβPFc and MLSA8790Fc (1 μg of each) were loaded on the gel for comparison. After staining of the gel with Coomassie blue, a doublet of bands were visible in the lane containing FGFRβFc, indicating that a complex formed between the FGF-2 and the murine FGF receptor homolog FGFRβFc, and that FGF-2 is a ligand for the novel FGF receptor homolog. A doublet was also observed in the lane containing the FGFR2Fc, which was the positive control. No doublet was observed in the negative control lane containing the MLSA8790Fc protein.

The binding specificity of the murine FGF receptor homolog FGFRβPFc was further examined by repeating the experiment described above, replacing the FGF-2 with another known growth factor, epidermal growth factor (EGF). In this experiment, EGF did not bind to FGFR2Fc, FGFRβFc or MLSA8790Fc, indicating that binding of FGF-2 to the murine FGF receptor homolog FGFRβFc was specific. Similarly, in subsequent experiments employing FGF-7, no binding of FGFR2Fc, FGFRβFc or MLSA8790Fc was observed.

Figure 2B:
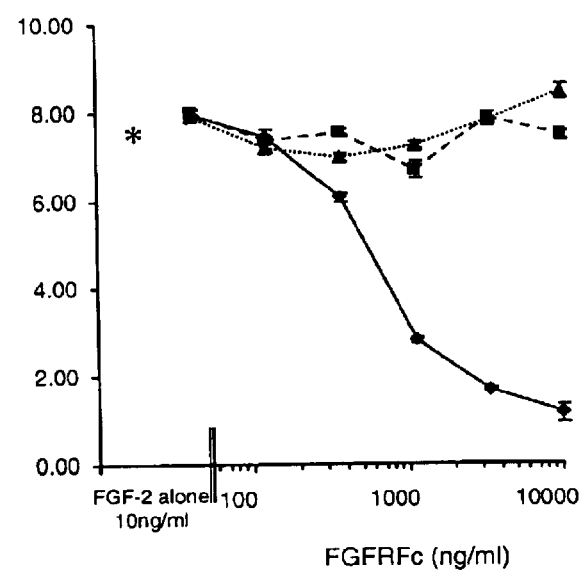

To determine the difference in binding affinity between FGFR5 and FGFR2, the ability of FGFRβFc and FGFRγFc to inhibit FGF signalling in FGF-responsive NIH-3T3 SRE reporter cells was examined. Fibroblast growth factors typically signal via phosphorylation of the receptor tyrosine kinase domain stimulating the MAP kinase pathway. This eventually leads to activation of genes under the control of the serum response element (SRE). Reporter constructs containing concatamerised SRE sequences upstream of a luciferase reporter gene were stably transfected into NIH-3T3 cells. Reporter activity was measured by measuring luciferase levels. As shown in FIG. 2A, a dose dependent response of NIH-3T3 SRE cells to FGF-2 was seen in the presence of heparin. Using a standard dose of FGF-2 in the presence of heparin, an increasing concentration of FGFR2Fc, FGFRβFc or FGFRγFc was titrated onto the NIH-3T3 SRE cells and luciferase activity was measured. Increasing concentrations of FGFR2Fc, the positive control, reduced the luciferase signal in FGF-2 stimulated cells (FIG. 2B). However, titrating FGFRβFc and FGFRγFc did not inhibit FGF-mediated luciferase signal from the NIH-3T3 SRE cells. These results show that FGF-2 has lower affinity for either FGFRβ or FGFRγ than for FGFR2, and indicate that the ligand specificity of FGFR5 is different to those of the other members of the FGF receptor family.

EXAMPLE 6

Sequence Determination of a Polynucleotide Fragment Containing Genomic Murine FGFRβ

As noted above, the two splice variants muFGFR-β and FGFR-γ do not contain the classical receptor tyrosine kinase domain present in other known FGF receptors. In order to investigate whether FGFR5 contains a splice variant with a classical receptor tyrosine kinase (RTK) domain, the genomic DNA of FGFR5 was sequenced as follows.

Mouse genomic DNA was isolated from L929 cells using standard techniques. A genomic polynucleotide fragment containing murine FGFRβ was PCR amplified using primers MS157 and MS166 (SEQ ID NO: 56 and 57, respectively). The 1.4 kb polynucleotide fragment was cloned into a T-tailed pBluescript SK$^{2+}$ vector. The sequence of the insert of this plasmid was determined using standard primer walking sequencing techniques. The sequence of the genomic fragment containing murine FGFRβ is given in SEQ ID NO: 46. This sequence extends from the 3' untranslated region to the end of the mature FGFR5 receptor minus the signal sequence. No alternative exons containing an RTK domain were identified.

EXAMPLE 7

Stimulation of Cell Growth by Murine FGFR5β and FGFR5γ

The stimulation of RAW264.10 cells (Hamilton et al., *J. Exp. Med.* 148:811–816, 1978) and peripheral blood mononuclear cells (PBMC) in the presence of the murine FGFRβ and FGFRγ (also referred to herein as FGFR5β and FGFR5γ, respectively) was demonstrated as follows. RAW264.10 cells are derived from a murine macrophage cell line generated from BALB/c mice, and are macrophage and osteoblast precursors.

Figure 3:
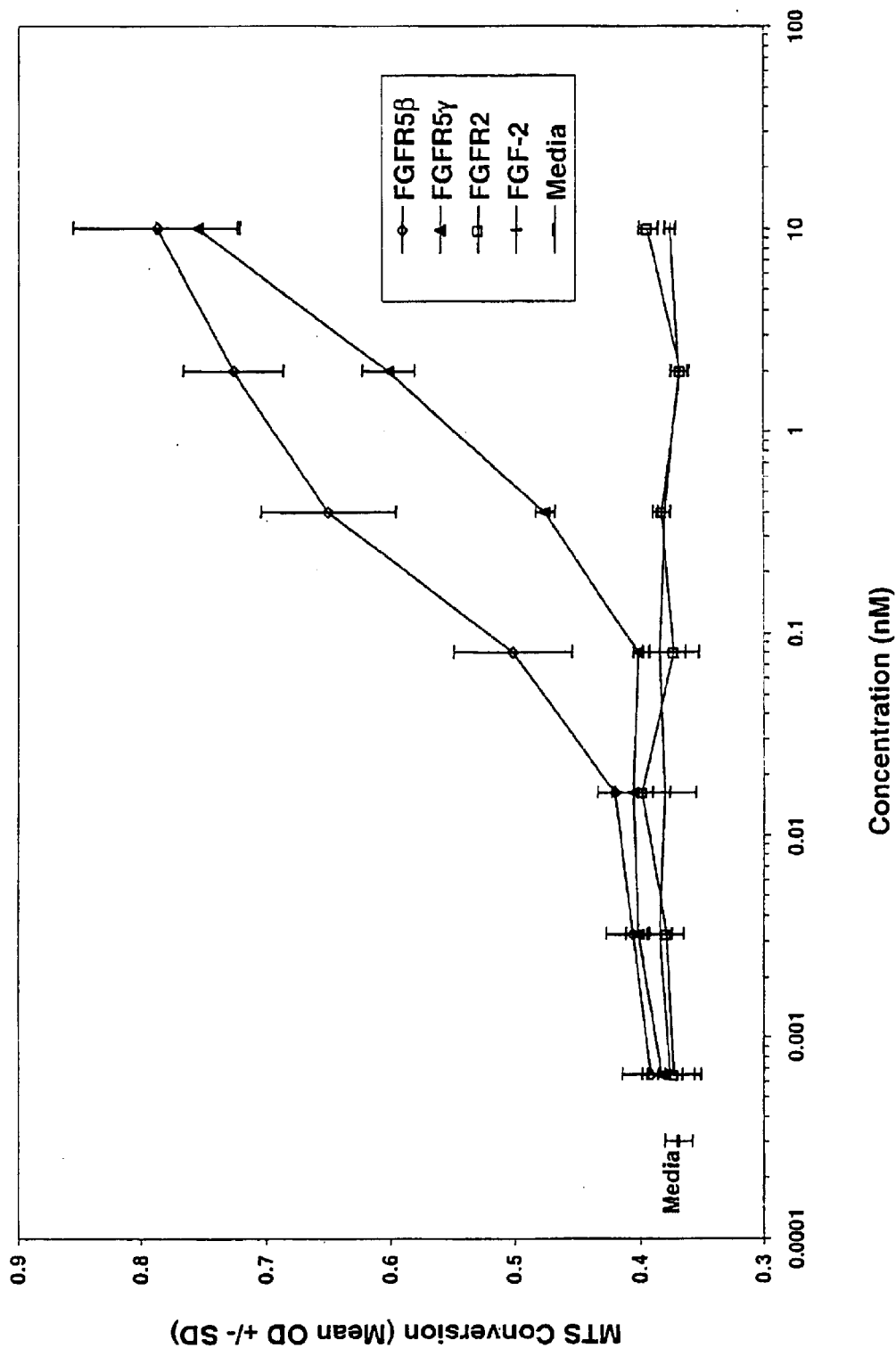
FIG. 3 illustrates the stimulation of growth of RAW264.10 cells by FGFR5β and FGFR5γ. This stimulation was not observed when FGF-2 and FGFR2 were used as controls. This stimulation was also not induced by the growth medium.

The murine FGF receptor homolog, muFGFRβ, and splice variant FGFRγ (SEQ ID NO: 22 and 23, respectively) were expressed in mammalian cells and purified as murine FGFR5β Fc fusion protein and FGFR5γ Fc fusion protein as described above. The FGFR5β and FGFR5γ Fc fusion proteins were titrated from 10 nM in 0.05 ml media (DMEM supplemented with 5%FBS, 2 mM L-glutamine (Sigma, St Louis Mo.), 1 mM sodium pyruvate (Life Technologies, Gibco BRL, Gaithersburg Md.), 0.77 mM L-asparagine (Sigma), 0.2 mM arginine (Sigma), 160 mM penicillin G (Sigma), 70 mM dihydrostreptomycin sulfate (Boehringer Mannheim, Roche Molecular Biochemicals, Basel, Switzerland) in a 96 well flat-bottomed microtitre plate. Purified human FGFR2 Fc fusion protein was used as control and titrated from 10 nM. RAW264.10 cells were added to each well in 0.05 ml media at a concentration of 2×10$^4$ cells/ml. The plate was incubated at 37° C. in a humidified atmosphere containing 10% $CO_2$ for 4 days. Cell growth was determined by MTS dye conversion and quantified using an ELISA reader. As shown in FIG. 3, both murine FGFR5β and FGFR5γ Pc fusion proteins stimulated the growth of RAW264.10 cells at concentrations of 100 pM and greater.

Figure 4:
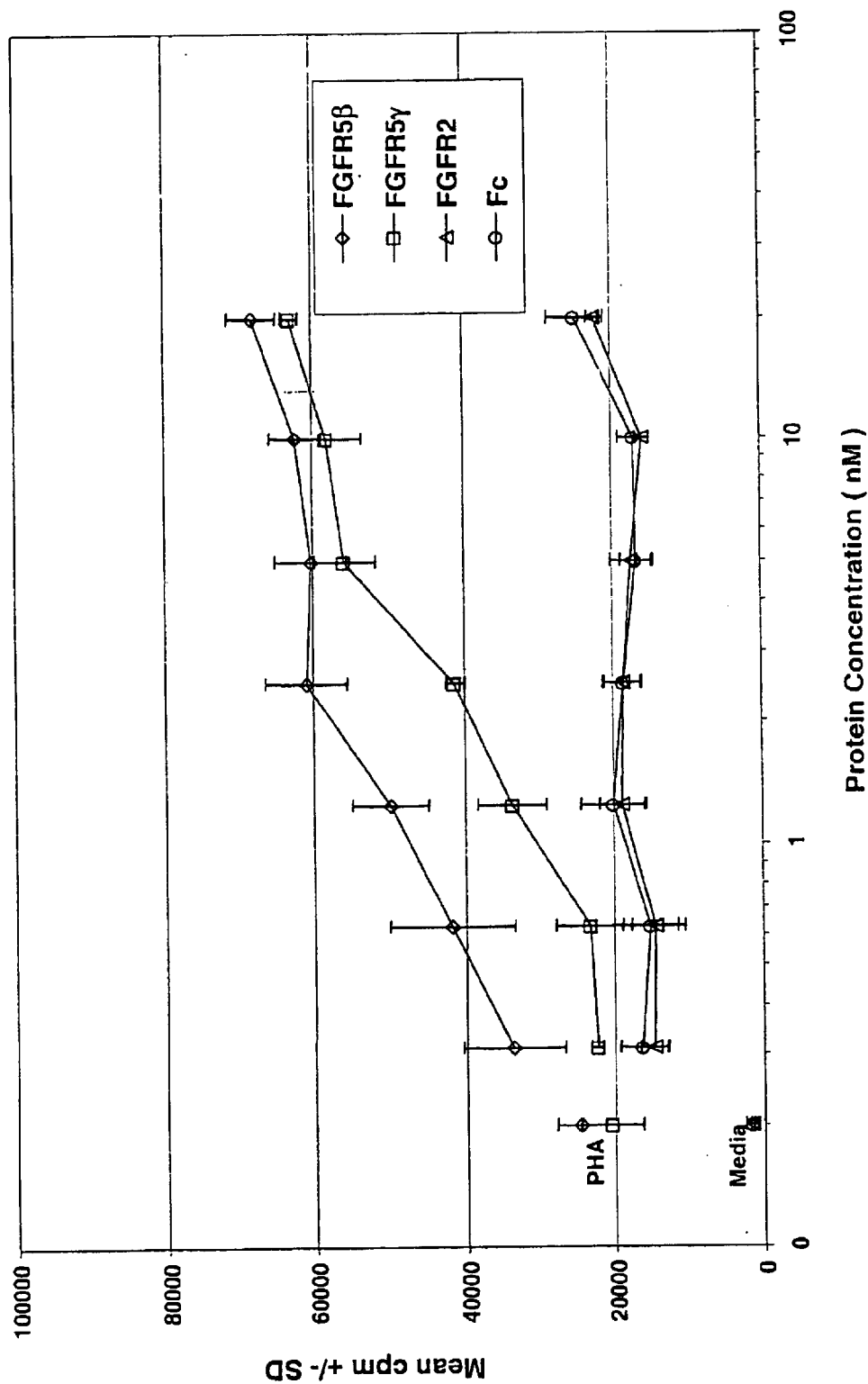
FIG. 4 illustrates the enhancing proliferative effect of FGFR5β and FGFR5γ on PHA-induced PBMC. The enhanced proliferation was not observed when FGFR2 or purified IgG Fc was used.
Figure 5:
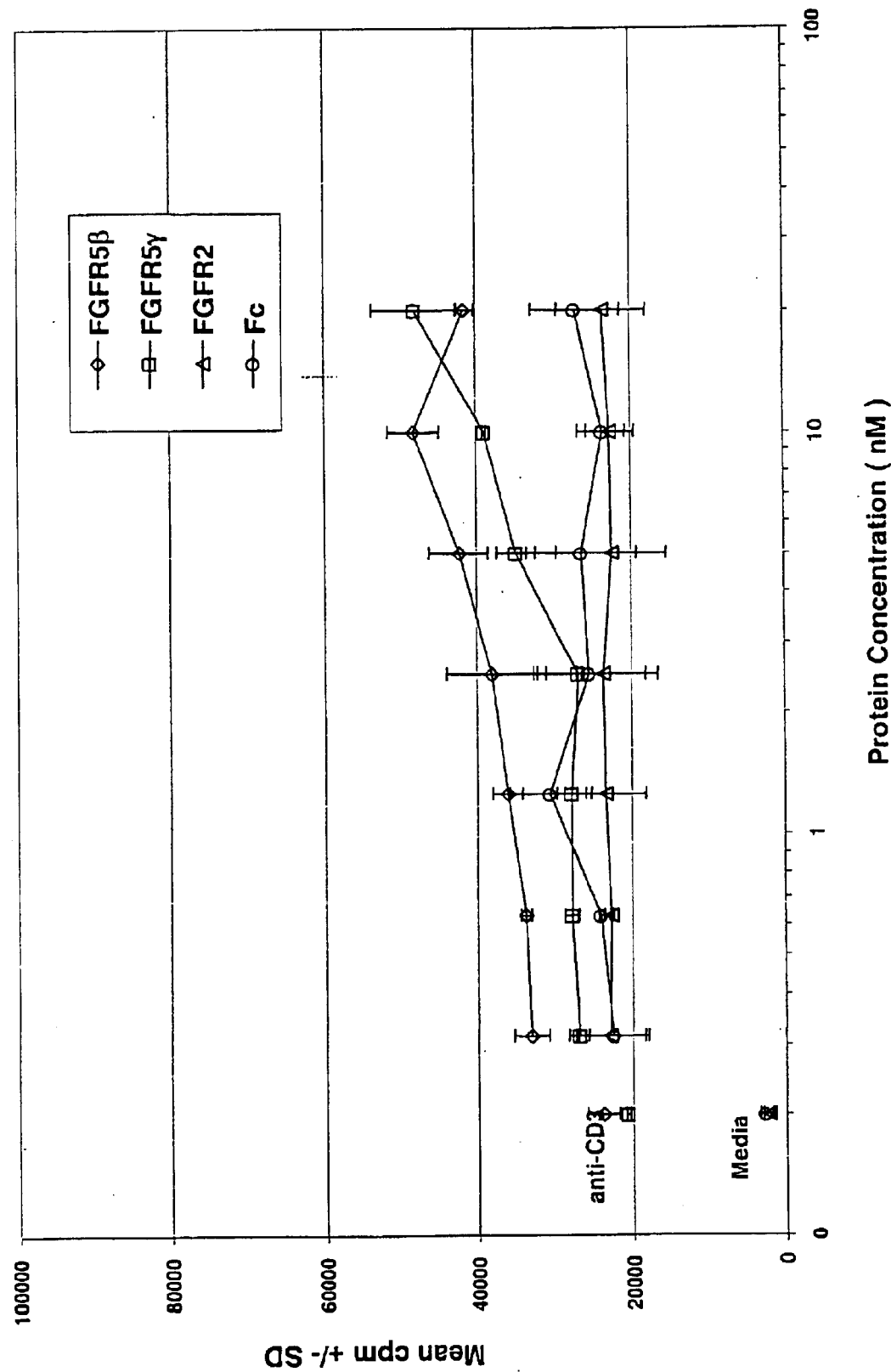
FIG. 5 shows the enhanced proliferation of anti-CD3 stimulated PBMC by FGFR5β and FGFR5γ. The enhanced proliferation was not observed when FGFR2 or purified FC was used as stimulants.
Figure 6:
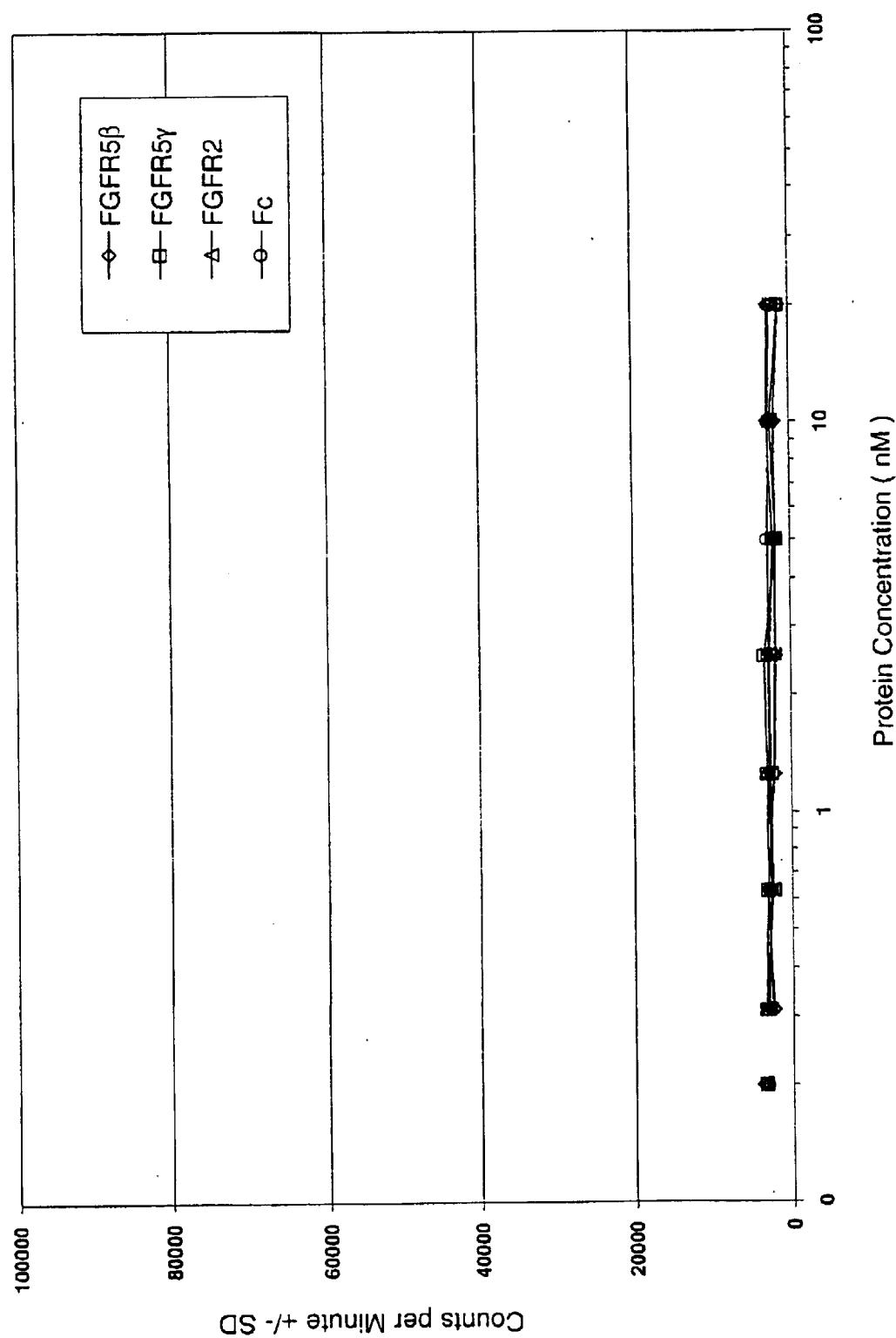
FIG. 6 demonstrates that FGFR5β and FGFR5γ, or the controls FGFR2 or IgG Fc did not stimulate proliferation of PBMC in the absence of PHA.

Purified FGFR5β and FGFR5γ Fc fusion proteins were titrated from 20 nM into 0.1 ml media per well of 96 well microtiter plates. Purified human FGFR2 Fc fusion protein and human IgG Fc were used as controls. PBMC were harvested from blood by density gradient centrifugation and resuspended in media to a concentration of 2×10$^6$ cells/ml. Phytokemagglutinin (PHA), Pokeweed mitogen (PWM), anti-CD3 antibody or media was added to the PBMC and 0.1 ml of cells dispensed to each well. The plates were incubated for 3 days at 37° C. in a humidified atmosphere containing 5% $CO_2$ in air. Cell proliferation was quantified by pulsing the plates with tritiated thymidine for the final 16 hours of culture. The cells were then harvested and tritiated thymidine incorporation enumerated by standard liquid scintillation counting. FIGS. 4–6 show that murine FGFR5β and FGFR5γ fusion proteins enhanced the proliferation of PBMC activated with either PHA or anti-CD3 but did not induce the proliferation of PBMC on their own. Stimulation of proliferation was not observed with human FGFR2 Fc fusion protein or human IgG Fc.

These results demonstrate that FGFR5β and FGFR5γ are immunostimulatory molecules that directly activate a macrophage cell line. The macrophage cell line used in these assays (RAW264.10) has previously been shown to differentiate into osteoblasts when stimulated with a variety of known bone morphogenic agents. The effects of FGFR5β and FGFR5γ on these cells suggest that these molecules may also stimulate the differentiation and activation of osteoblasts. Weidemann and Trueb (*Genomics* 69:275–279, 2000), have shown that FGFR5 is expressed in cartilaginous tissues. When combined with the data provided above, this suggests that FGFR5 may play a role in bone formation and may therefore have applications in fracture repair and bone diseases, such as osteoporosis and osteopetrosis.

EXAMPLE 8

Stimulation of Proliferation of Adherent Peripheral Blood Mononuclear Cells (Pbmc) by Murine FGFR5β and FGFR5γ

Stimulation of PBMC to adhere to plastic by murine FGFR5β and FGFR5γ Fc fusion proteins was demonstrated as follows.

Figure 7:
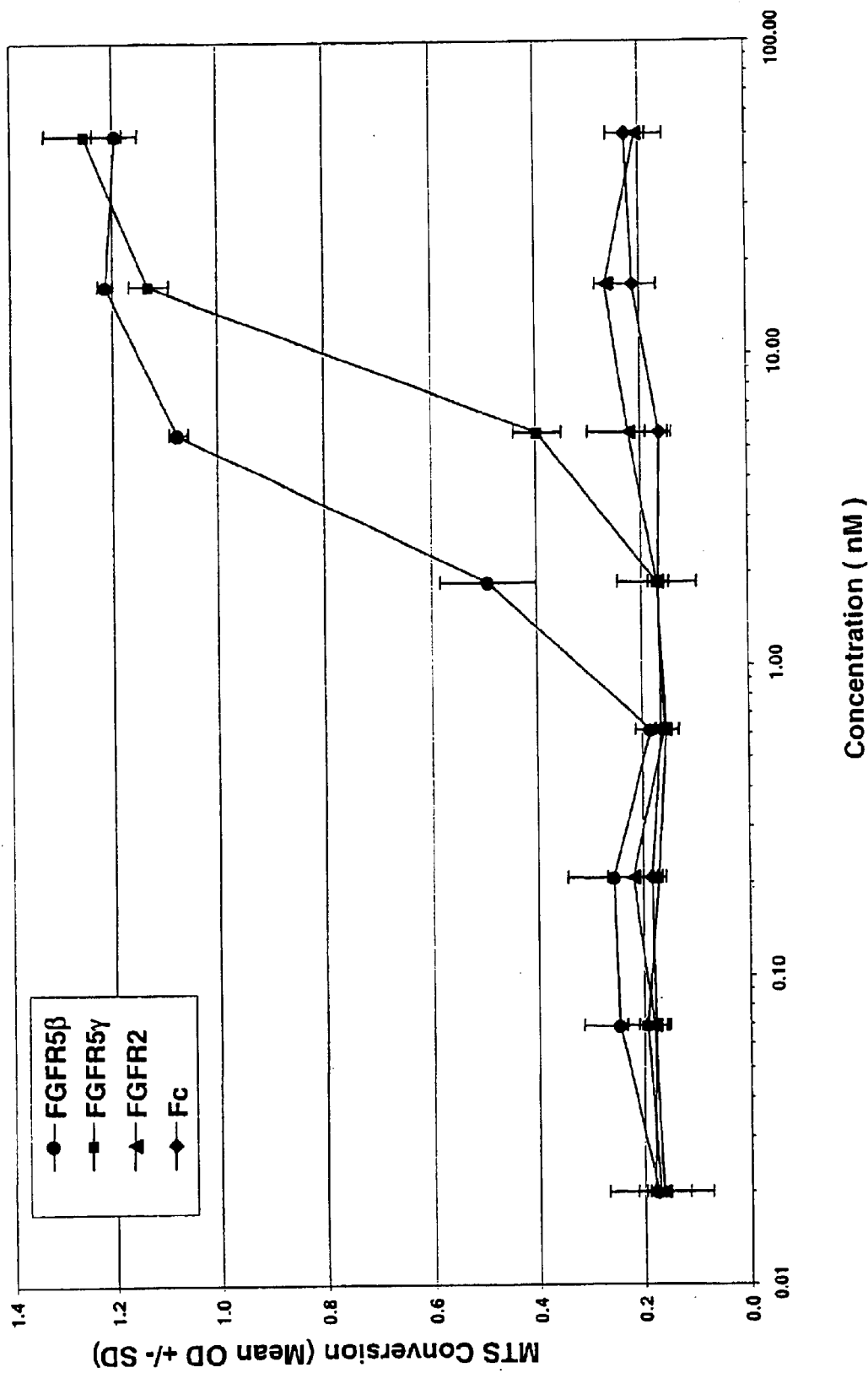
FIG. 7 illustrates the stimulation of PBMC adherence by FGFR5β and FGFR5γ but not by FGFR2 or purified IgG Fc.
Figure 8:
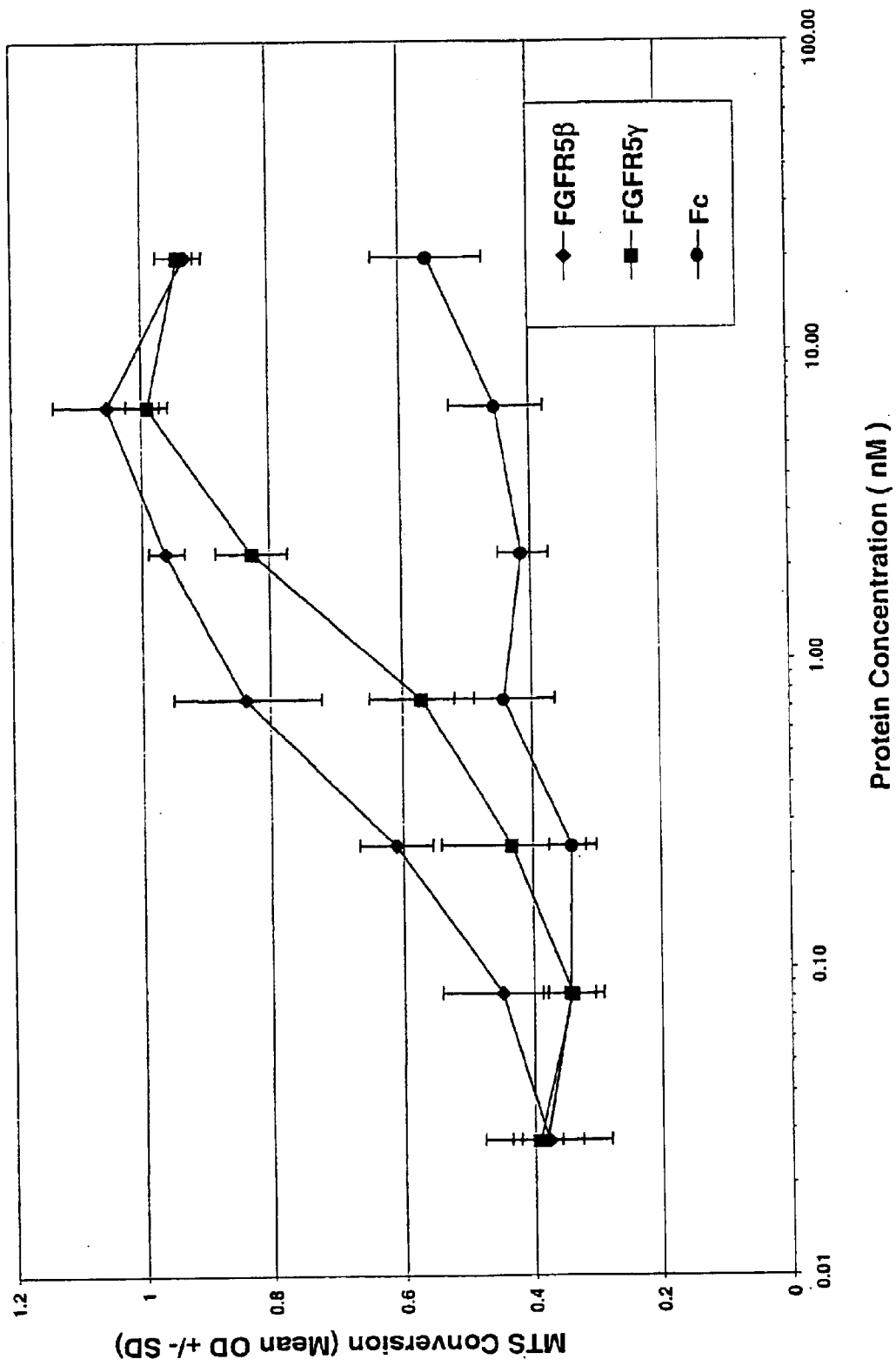
FIG. 8 shows the stimulation of adherent PHA-stimulated PBMC by FGFR5β and FGFR5γ but not by purified IgG Fc.

MuFGFR5β and muFGFR5γ (SEQ ID NO: 22 and 23, respectively) were expressed in mammalian cells and purified as Fc fusion proteins as described above. The muFGFR5β and muFGFR5γ Fc fusion proteins were titrated from 10 mM into 0.1 ml media per well of 96 well microtitre plates. Peripheral blood mononuclear cells (PBMC) were harvested from blood by density gradient centrifugation and resuspended in media to a concentration of 2×10$^6$ cells/ml. PHA or media (RPMI 1640 supplemented with 5% FBS, 2 mM L-glutamine (Sigma), 160 mM penicillin G (Sigma), and 70 mM dihydrostreptomycin sulfate (Boehringer Mannheim) was added to the PBMC and 0.1 ml of cells dispensed to each well. The plates were incubated for 3 days at 37° C. in a humidified atmosphere containing 5% $CO_2$ in air. The non-adherent cells were removed with three media washes. Media (0.05 ml) containing MTS/PES solution (CellTiter96 Aqueous One Solution Cell Proliferation Assay, Promega, Madison, Wis.) was dispensed to each well and the plate incubated for 4 hrs before the degree of dye conversion was quantified using a 96 well ELISA reader. FIGS. 7 and 8 show that muFGFR5β and muFGFR5γ Fc fusion proteins stimulated the adherence and proliferation of adherent PBMC in a dose dependent manner and that PHA stimulation augmented this effect. These results demonstrate that FGFR5β and FGFR5γ are able to enhance the proliferative effects of known immunostimulatory molecules on a mixed population of human haemopoietic cells, namely PBMC.

EXAMPLE 9

Activation of Natural Killer Cells by Murine FGFR5β and FGFR5γ

Activation of Natural Killer (NK) cells by muFGFR5β and muFGFR5γ Fc fusion proteins was demonstrated as follows.

Peripheral blood mononuclear cells (PBMC) were harvested from blood by density gradient centrifugation and resuspended in media (RPMI 1640 supplemented with 5% FBS, 2 mM L-glutamine (Sigma), 160 mM penicillin G (Sigma), 70 mM dihydrostreptomycin sulfate (Boehringer Mannheim)) to a concentration of 2×10$^6$ cells/ml. Purified muFGFR5β and muFGFR5γ Pc fusion protein were added to the cells at a concentration of 10 nM and the cells were cultured in 6 well plates (3 ml/well) for 3 days at 37° C. in a humidified atmosphere containing 5% $CO_2$ in air. Purified human FGFR2 Fc fusion protein was used as control. The non-adherent cells were removed with three media washes. The adherent cells were collected by light trypsinization and scraping. The cells were washed into staining buffer and their phenotype determined by standard flow cytometric techniques using NK cell marker CD56 and a control isotype antibody.

As shown in FIG. 9, muFGFR5β and muFGFR5γ Fc fusion proteins stimulated the adherence and/or growth of adherent cells from human PBMC, with approximately 50% of these cells being NK cells. The filled histograms represent the adherent PBMC stained with the NK cell marker CD56 and the open histograms represent the same cells stained with the isotype-matched control antibody. FGFR2 did not stimulate the adherence of PBMC and therefore there were no cells to analyze from these cultures. These results demonstrate that FGFR5β and FGFR5γ are immunostimulatory molecules that directly activate NK cells. These results, plus those provided in Example 8, above, show that FGFR5 can enhance immune responses, and may thus be usefully employed to enhance vaccine responses and anti-cancer therapies.

EXAMPLE 10

Immunoprecipitation of a 20–30 KDA Surface Protein From RAW264.10 Cells by MuFGFR5β and MuFGFR5γ Fc Fusion Proteins Immunoprecipitation of a 20–30 kDa protein from the surface of RAW264.10 cells by murine FGFR5β and FGFR5γ Fc fusion proteins, but not FGFR2 or control (murine MALA13003) Fc fusion proteins was demonstrated as follows. Murine MALA13003 is a novel receptor of unknown function.

Preparation of Protein A beads bound with Murine FGFRβ and FGFR5γ Fc Fusion Proteins Two μl Protein A Beads (Protein A Ceramic HyperDF, Gibco BRL) were dispensed into 4 nicrofuge tubes. The beads were washed three times in IP wash buffer (50 mM Tris.HCl pH 7.5, 0.5 M NaCl, 1 mM $CaCl_2$, 1 mM $MgCl_2$, 0.1% Tween-20). The IP wash buffer was removed and 20 μg purified murine FGFR5β, FGFR5γ, FGFR2 or murine MALA 31003 Fc fusion proteins was added to each microfuge tube and incubated on a rocking platform for either 2–3 hours at room temperature or overnight at 4° C. The beads were washed three times with IP wash buffer and centrifuged at 3,000 rpm for 2 min.

Preparation of Cells

RAW264.10 cells were harvested when at 75% confluence by using single strength trypsin and washed in PBS. After counting, the cell concentration was adjusted to $5 \times 10^6$ cells/ml in 5 ml PBS.

Biotinylation

A stock solution of N-hydroxysuccinimido-biotin (NHS-Biotin, Sigma) at 10 mg/ml was prepared in PBS. An aliquot of this stock biotin solution was added immediately to the RAW264.10 cell suspension to a final concentration of 100 μg/ml biotin and mixed carefully. The cell suspension was incubated at room temperature for 60 min on a rocking platform to prevent the cells from settling. The cells were washed three times by centrifugation at 1,000 rpm for 7 min and resuspension in glycine buffer (PBS, 10 mM glycine, pH 7.5) to block all free NHS-Biotin sites. The glycine was removed by washing the cells twice in PBS. The cells were aliquoted into four 1 ml portions of $5 \times 10^6$ cells/ml each and pelleted by centrifugation.

Extraction of Soluble Proteins

One ml of extraction buffer (50 mM Tris. HCl pH 7.5, 0.15 M NaCl, 1 mM $CaCl_2$, 1 mM $MgCl_2$, 1% NP40) was added to each cell pellet. Cells were disrupted by using a syringe until the cell pellet was solubilized. The solubilized cells were centrifuged at 10,000 rpm for 10 min at 4° C. and the supernatant was collected.

Immunoprecipitation

The cell lysates were pre-cleared twice by adding 2 μl washed Protein A beads and incubating for 1 hour at room temperature. The cell suspension was centrifuged and the supernatant collected. One ml pre-cleared lysate was added to each of the microfuge tubes containing 2 μl protein A beads coated with FGFR5β, FGFR5γ, FGFR2 or MALA 31003 Fc fusion proteins and incubated overnight at 4° C. on a rocking platform. The beads were washed four times in IP wash buffer with a centrifugation step (4,000 rpm for 2 min). After the first wash, the bead suspension was transferred to a new tube so that the final sample was not contaminated with non-bound recombinant protein that may be stuck to the side of the tube. The supernatant was aspirated leaving approximately 20 μl of liquid on the beads. After the final wash, all the remaining 20 μl of supernatant on the beads was removed and the beads resuspended in 20 μl RSB (0.08 M Tris.HCl pH 6.8, 0.01 M DTT (Dithiothreitol), 2% SDS, 10% glycerol).

Polyacrylamide Gel Electrophoresis

The prepared beads were run on two resolving polyacrylamide gels following standard procedures. One gel was stained with Coomassie Blue and the second gel was blotted onto PVDF (polyvinylidene difluoride) membrane (Immobilon-P Transfer Membrane, Millipore, Bedford Mass.) by Western transfer following standard procedures. The blot was developed using ECL Western Blotting Detection Reagent (Amersham Pharmacia, Uppsala, Sweden) and exposed to Scientific Imaging film (Agfa Curix Blue HC-S Plus).

A protein of 20 to 30 kDa molecular weight was immunoprecipitated from the surface of RAW264.10 cells by the murine FGFR5β and FGFR5γ Fc fusion proteins, but not FGFR2 or MALA13003 Fc fusion proteins. This precipitated protein is likely to be the ligand or a component of the ligand complex recognized by FGFR5.

SEQ ID NOS: 1–61 are set out in the attached Sequence Listing. The codes for polynucleotide and polypeptide sequences used in the attached Sequence Listing conform to WIPO Standard ST.25 (1988), Appendix 2.

All references cited herein, including patent references and non-patent references, are hereby incorporated by reference in their entireties.

Although the present invention has been described in terms of specific embodiments, changes and modifications can be carried out without departing from the scope of the invention which is intended to be limited only by the scope of the appended claims.

What is claimed is:

1. A method for enhancing an immune response in a patient, comprising:
   (a) administering to the patient a composition comprising an isolated polypeptide, wherein the polypeptide comprises SEQ ID NO: 33; and
   (b) enhancing an immune response in the patient.

2. The method of claim 1, wherein the composition further comprises at least one component selected from the group consisting of: physiologically acceptable carriers and non-specific immune response enhancers.

3. The method of claim 1, wherein the composition is administered by injection.

4. The method of claim 2, wherein the physiologically acceptable carrier is selected from the group consisting of: water, saline, alcohol, lipids, waxes, buffers, mannitol, lactose, starch, magnesium stearate, sodium saccharine, talcum, cellulose, glucose, sucrose, magnesium carbonate and biodegradable microspheres.

5. The method of claim 2, wherein the non-specific immune response enhancer is an adjuvant.

6. A method for enhancing an immune response in a patient, comprising:
   (a) administering to the patient a composition comprising an isolated polypeptide, wherein the polypeptide comprises a sequence selected from the group consisting of sequences having at least 95% identity to SEQ ID NO: 33 and wherein the polypeptide has the same functional properties as SEQ ID NO: 33; and
   (b) enhancing an immune response in the patient.

7. The method of claim 6, wherein the composition further comprises at least one component selected from the group consisting of: physiologically acceptable carriers and non-specific immune response enhancers.

8. The method of claim 6, wherein the composition is administered by injection.

9. The method of claim 7, wherein the physiologically acceptable carrier is selected from the group consisting of: water, saline, alcohol, lipids, waxes, buffers, mannitol, lactose, starch, magnesium stearate, sodium saccharine, talcum, cellulose, glucose, sucrose, magnesium carbonate and biodegradable microspheres.

10. The method of claim 7, wherein the non-specific immune response enhancer is an adjuvant.

11. A method for enhancing an immune response in a patient, comprising:
    (a) administering to the patient a composition comprising an isolated polypeptide, wherein the polypeptide comprises a sequence selected from the group consisting of sequences having at least 95% identity to SEQ ID NO: 33 and is able to bind to fibroblast growth factor; and
    enhancing an immune response in the patient.

12. The method of claim 11, wherein the composition further comprises at least one component selected from the group consisting of: physiologically acceptable carriers and non-specific immune response enhancers.

13. The method of claim 11, wherein the composition is administered by injection.

14. The method of claim 12, wherein the physiologically acceptable carrier is selected from the group consisting of: water, saline, alcohol, lipids, waxes, buffers, mannitol, lactose, starch, magnesium stearate, sodium saccharine, talcum, cellulose, glucose, sucrose, magnesium carbonate and biodegradable microspheres.

15. The method of claim 12, wherein the non-specific immune response enhancer is an adjuvant.

* * * * *